(12) United States Patent
Yang et al.

(10) Patent No.: US 12,194,024 B2
(45) Date of Patent: Jan. 14, 2025

(54) PHARMACEUTICAL COMPOSITION OF MDM2 INHIBITOR AND USE THEREOF FOR PREVENTING AND/OR TREATING DISEASE

(71) Applicants: ASCENTAGE PHARMA (SUZHOU) CO., LTD., Suzhou (CN); ASCENTAGE PHARMA GROUP CORP LIMITED, Central (CN)

(72) Inventors: Dajun Yang, Suzhou (CN); Yifan Zhai, Suzhou (CN); Qiuqiong Tang, Suzhou (CN); Douglas Dong Fang, Suzhou (CN); Jing Deng, Suzhou (CN)

(73) Assignees: ASCENTAGE PHARMA (SUZHOU) CO., LTD. (CN); ASCENTAGE PHARMA GROUP CORP LIMITED (CN)

(*) Notice: Subject to any disclaimer, the term of this patent is extended or adjusted under 35 U.S.C. 154(b) by 247 days.

(21) Appl. No.: 17/277,562

(22) PCT Filed: Jul. 24, 2020

(86) PCT No.: PCT/CN2020/104088
§ 371 (c)(1),
(2) Date: Mar. 18, 2021

(87) PCT Pub. No.: WO2021/018032
PCT Pub. Date: Feb. 4, 2021

(65) Prior Publication Data
US 2022/0142979 A1 May 12, 2022

(30) Foreign Application Priority Data

Jul. 26, 2019 (WO) ............... PCT/CN2019/097916
Jan. 20, 2020 (WO) ............... PCT/CN2020/073124

(51) Int. Cl.
| | | |
|---|---|---|
| A61K 31/407 | (2006.01) | |
| A61K 31/4439 | (2006.01) | |
| A61K 31/506 | (2006.01) | |
| A61K 31/519 | (2006.01) | |
| A61K 31/55 | (2006.01) | |
| A61K 31/565 | (2006.01) | |
| A61K 31/7068 | (2006.01) | |
| A61P 35/00 | (2006.01) | |

(52) U.S. Cl.
CPC ........ *A61K 31/407* (2013.01); *A61K 31/4439* (2013.01); *A61K 31/506* (2013.01); *A61K 31/519* (2013.01); *A61K 31/55* (2013.01); *A61K 31/565* (2013.01); *A61K 31/7068* (2013.01); *A61P 35/00* (2018.01)

(58) Field of Classification Search
CPC ............. A61K 31/407; A61K 31/4439; A61K 31/506; A61K 31/519; A61K 31/55; A61K 31/565; A61K 31/7068; A61K 31/706; A61K 45/06; A61K 31/437; A61P 35/00; A61P 7/00; A61P 35/02; C07D 487/10
See application file for complete search history.

(56) References Cited

U.S. PATENT DOCUMENTS

| | | | | |
|---|---|---|---|---|
| 11,452,716 B2 * | 9/2022 | Yang | ................... | A61K 31/519 |
| 11,478,469 B2 * | 10/2022 | Yang | ..................... | A61P 35/02 |
| 11,787,814 B2 * | 10/2023 | Guo | ...................... | C07C 271/22 |
| | | | | 548/486 |
| 11,850,239 B2 * | 12/2023 | Zhai | ....................... | A61P 35/00 |
| 2016/0367662 A1 * | 12/2016 | Greshock | ............... | A61P 35/02 |

FOREIGN PATENT DOCUMENTS

| | | | |
|---|---|---|---|
| EP | 3527226 | | 8/2019 |
| WO | WO2012155066 A1 | | 11/2012 |
| WO | WO2015070224 A2 | | 5/2015 |
| WO | WO2015082384 A1 | | 6/2015 |
| WO | WO-2015161032 A1 * | 10/2015 | ........... A61K 31/407 |
| WO | WO2017037579 A1 | | 3/2017 |
| WO | WO2020024820 A1 | | 2/2020 |
| WO | WO2020030016 A1 | | 2/2020 |
| WO | WO2020103922 A1 | | 5/2020 |

OTHER PUBLICATIONS

A Phase Ib Study of APG-115 Single Agent or in Combination With Azacitidine or Cytarabine in Patients With AML and MDS; ClinicalTrials.gov Identifier: NCT04275518; Feb. 19, 2020 https://clinicaltrials.gov/ct2/show/NCT04275518.
A Phase Ib/II Study of APG-115 Alone or in Combination With Azacitidine in Patients With Relapse/Refractory AML; ClinicalTrials.gov Identifier: NCT04358393; Apr. 24, 2020 https://clinicaltrials.gov/ct2/show/NCT04358393.
International Search Report for PCT/CN2020/104088 dated Oct. 28, 2020.
Deng, Jing et al., Probing Distinct Oncogene Addiction By Novel BCL-2 Inhibitors, Blood, American Society of Hematology, US, vol. 132, Nov. 29, 2018, p. 2616, XP086590053, ISSN: 0006-4971, DOI: 10.1182/BLOOD-2018-99-119816.
Aguilar, Angelo et al., Discovery of 4-((3′R,4′S,5′R)-6″-Chloro-4′-(3-chloro-2-fluorophenyl)-1′-ethyl-2″-oxodispiro [cyclohexane-1,2′-pyrrolidine-3′,3″-indoline]-5′-carboxamido)bicyclo[2.2.2]octane-1-carboxylic Acid (AA-115/APG-115): A Potent and Orally Active Murine Double Minute 2 (MDM2) Inhibitor in Clinical Development, Journal of Medicinal Chemistry, vol. 60, No. 7, Mar. 24, 2017, pp. 2819-2839, XP055680933, ISSN: 0022-2623, DOI: 10.1021/acs.jmedchem.6b01665.

(Continued)

*Primary Examiner* — Matthew P Coughlin
*Assistant Examiner* — Meghan C Heasley
(74) *Attorney, Agent, or Firm* — Honigman LLP; Lucy X. Yang; Jonathan P. O'Brien

(57) ABSTRACT

Provided herein are pharmaceutical compositions comprising an MDM2 inhibitor and one or more anti-cancer agents for preventing and/or treating diseases, such as cancer. Methods for preventing and/or treating diseases, such as cancer, comprising administering to the patient in need thereof with the pharmaceutical compositions are also provided.

5 Claims, 17 Drawing Sheets

(56) References Cited

OTHER PUBLICATIONS

Fang, Douglas D. et al., Abstract 1253: MDM2 inhibitor APG-115 synergizes with CDK4/6 inhibitors in a patient-derived xenograft model of dedifferentiated liposarcoma, Jul. 1, 2019, pp. 1-2, XP093036333, Retrieved from the Internet: URL:https://aacjournals.org/cancerres/article/79/13_Supplement/1253/542206/Abstract-1253-MDM2-inhibitor-APG-115-synergizes[retrieved on Mar. 30, 2023].

* cited by examiner

MOLM-13 48 h

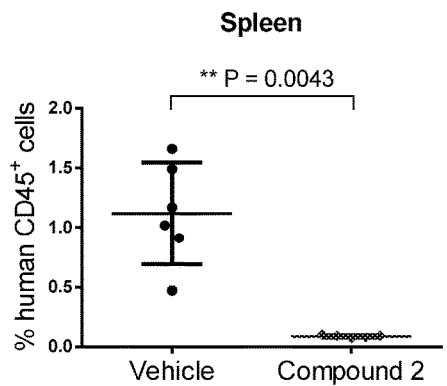
FIG. 9D
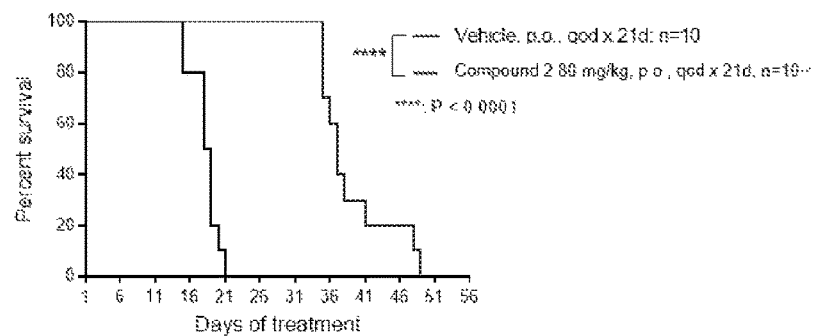
FIG. 10
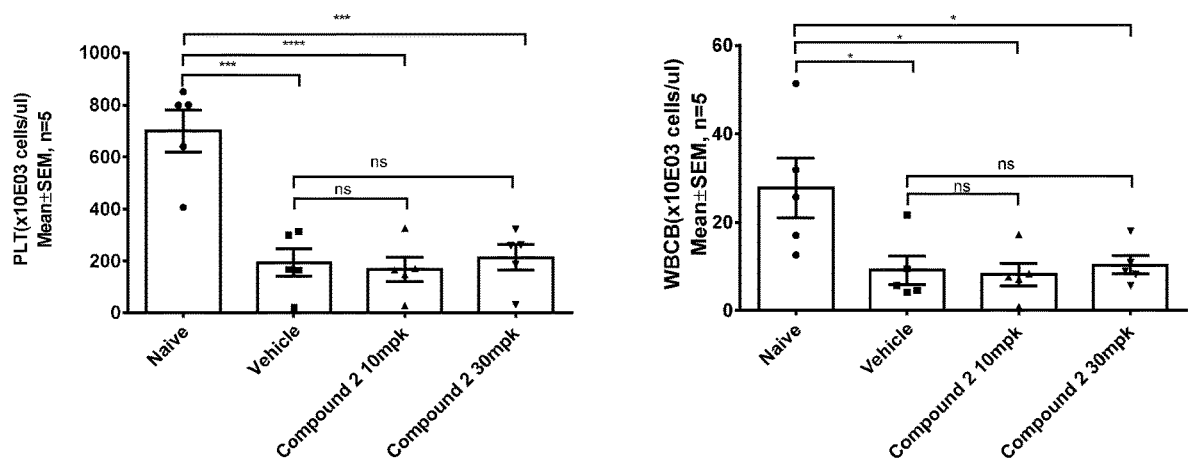

PHARMACEUTICAL COMPOSITION OF MDM2 INHIBITOR AND USE THEREOF FOR PREVENTING AND/OR TREATING DISEASE

CROSS-REFERENCE TO RELATED APPLICATIONS

This application is a 35 U.S.C. § 371 United States National Phase Application of, and claims priority to, PCT Application No. PCT/CN2020/104088, filed Jul. 24, 2020, which claims priority to PCT Application No. PCT/CN2020/073124, filed Jan. 20, 2020, and PCT Application No. PCT/CN2019/097916, filed Jul. 26, 2019. The entire contents of the aforementioned applications are incorporated herein by reference.

TECHNICAL FIELD

The present invention belongs to the technical field of medicine and in particular to a pharmaceutical composition comprising an MDM2 inhibitor and one or more anti-cancer agents, and the use of same for preventing and/or treating a disease (such as cancer).

BACKGROUND ART

An MDM2 inhibitor interferes with the binding of an MDM2 oncoprotein to a tumor suppressor p53 protein, thus serving as a drug of p53 activator. Emerging evidence implicates that p53 dysfunction may also exacerbate inflammation and support tumor immune escape, and thus the p53 dysfunction can act as an immune driving factor of tumorigenesis (Guo G, Cancer Research, 2017; 77(9):2292).

MDM2 and p53 are parts of a self-regulating feedback loop (Wu et al., Genes Dev. 7:1126 (1993)). The MDM2 transcription is activated by p53 and MDM2, and furthermore, the p53 activity is inhibited by at least three mechanisms (Wu et al., Genes Dev. 7:1126(1993)). Firstly, the MDM2 protein is directly bound to a p53 trans-activation domain, and thus inhibits the p53 mediated trans-activation. Secondly, the MDM2 protein contains a nuclear export signal sequence, and when bound to p53, it induces the nuclear export of p53, thus blocking the binding of p53 to the targeted DNA. Thirdly, the MDM2 protein is an E3 ubiquitin ligase, and when bound to p53, can promote p53 degradation.

With the research progress of molecular biology, the molecular targeting therapy has become a hotspot of medical research (especially tumor research), and the biological behaviors of most tumors are affected by multiple signaling pathways rather than dominated by a single signaling pathway. Therefore, there is a demand in the prior art for a combination administration regimen and a product for different target proteins and/or different signaling pathways, wherein the combination administration regimen and the product can reduce the dosage of a single drug, decrease the toxic and side effects of the single drug and/or take effect in a synergistic way, and realize the purpose of preventing and/or treating a disease.

SUMMARY OF THE INVENTION

Now the applicants of the present invention have found that an MDM2 inhibitor or an acceptable salt, carrier, diluent, or excipient thereof and an anti-cancer agent, especially in co-administration with Homoharringtonine, demethylation drugs and/or antimetabolites can synergistically treat cancer. In particular, as shown in embodiments 1-10 of the present invention, combining an MDM2 inhibitor (such as Compound 2) with an anti-cancer agent (such as Decitabine, Azacitidine, Cytarabine, Trametinib, combination of Dabrafenib and Trametinib, or combination of Fulvestrant and Alpelisib) can unexpectedly more significantly upregulate P21 protein, effectively induce P21 accumulation, or alleviate tumors and delay tumor growth or lead to tumor regression.

In one aspect of the present invention, provided is a pharmaceutical composition comprising an MDM2 inhibitor and one or more anti-cancer agents and optionally a pharmaceutically acceptable carrier, diluent or excipient.

In a preferred embodiment, said MDM2 inhibitor is a compound of following structural formula or a pharmaceutically acceptable salt or solvate thereof:

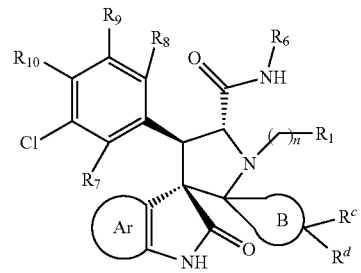

wherein:

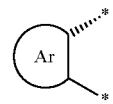

is selected from the group consisting of:

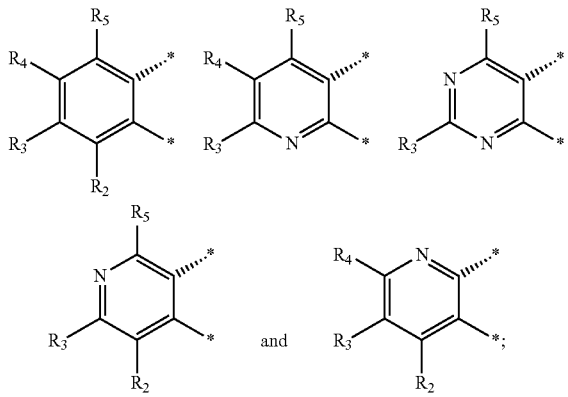

B is a $C_{4-7}$carbocyclic ring;

$R_1$ is H, substituted or unsubstituted $C_{1-4}$alkyl, substituted or unsubstituted $C_{3-8}$cycloalkyl, substituted or unsubstituted heterocycloalkyl, $OR^a$ or $NR^aR^b$;

n is 0, 1 or 2;

$R_2$, $R_3$, $R_4$, $R_5$, $R_7$, $R_8$, $R_9$, and $R_{10}$ are independently selected from the group consisting of H, F, Cl, $CH_3$, and $CF_3$;

$R_6$ is

$R^a$ is hydrogen or substituted or unsubstituted $C_{1-4}$alkyl;
$R^b$ is hydrogen or substituted or unsubstituted $C_{1-4}$alkyl;
$R^c$ and $R^d$ are substituents on one carbon atom of ring B, wherein
$R^c$ is H, $C_{1-3}$alkyl, $C_{1-3}$alkylene-$OR^a$, $OR^a$, or halo;
$R^d$ is H, $C_{1-3}$alkyl, $C_{1-3}$alkylene-$OR^a$, $OR^a$, or halo; or
$R^c$ and $R^d$ are taken together with the carbon to which they are attached to form a 4- to 6-membered spirocyclic substituent, which optionally contains an oxygen or nitrogen atom; and
$R^e$ is —C(=O)$OR^a$, —C(=O)$NR^aR^b$, or —C(=O)NHSO$_2$CH$_3$.

In a preferred embodiment,

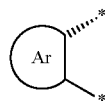

is

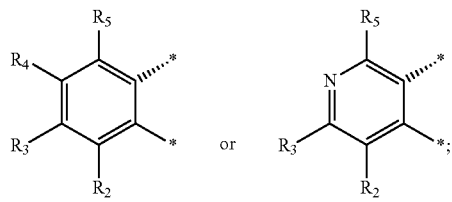

B is

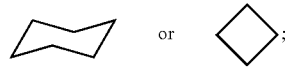

$R^c$ and $R^d$ are F and F, H and H, OH and CH$_3$, CH$_3$ and CH$_3$, CH$_3$ and OH, H and OH, CH$_2$CH$_3$ and CH$_2$CH$_3$, and CH$_2$OH and CH$_2$OH.

In a preferred embodiment, said pharmaceutical composition, wherein —(CH$_2$)$_n$R$_1$ is H, CH$_3$, or CH$_2$CH$_3$.

In a preferred embodiment, R$_2$ is H; R$_3$ is halo; and R$_4$ and R$_5$ are both H.

In a preferred embodiment, R$_7$ is halo; each of R$_8$, R$_9$, and R$_{10}$ is H; $R^e$ is —C(=O)OH, —C(=O)NH$_2$, or —C(=O)NHSO$_2$CH$_3$.

In a preferred embodiment, said MDM2 inhibitor is a compound 1 and a pharmaceutically acceptable salt or solvate thereof:

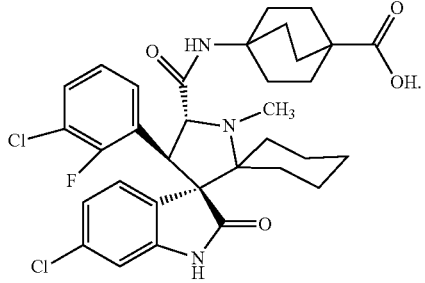

compound 1

In a preferred embodiment, said MDM2 inhibitor is the compound 2 and a pharmaceutically acceptable salt or solvate thereof:

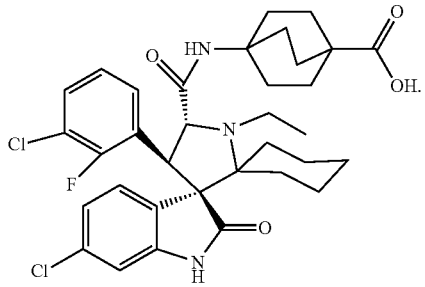

compound 2

In a preferred embodiment, the anti-cancer agent is selected from chemotherapeutic drugs, comprising Homoharringtonine, demethylation drugs and/or antimetabolites; preferably, said demethylation drugs comprising Azacitidine, Decitabine, Zebularine, Fazadinium or dihydro-5'-cytidine; and preferably, said antimetabolites comprising Cytarabine, ancitabine, Gemcitabine or Troxacitabine.

In a preferred embodiment, said anti-cancer agent is selected from MEK inhibitors.

Preferably, said MEK inhibitors comprising Pimasertib, PD184352, PD0325901, Selumetinib, PD98059, U0126-EtOH, TAK-733, Refametinib, GDC-0623, RO4987655, RO5126766 (CH5126766), SL-327, BI-847325 or Trametinib.

In a preferred embodiment, Said anti-cancer agents are one or more selected from the followings: BRAF inhibitor, MEK inhibitor, Estrogen Receptor inhibitor, PI3k inhibitor. Said BRAF inhibitor is selected from Sorafenib, PLX-4720, Regorafenib (BAY 73-4506), GDC-0879, RAF265, SB590885, AZ 628, ML 7866dihydrochloride, PF-04880594, TAK-632, CEP-32496, RO5126766 or Dabrafenib. Said MEK inhibitor is selected from Pimasertib, PD184352, PD0325901, Selumetinib, PD98059, U0126-EtOH, TAK-733, Refametinib, GDC-0623, RO4987655, RO5126766 (CH5126766), SL-327, BI-847325 or Trametinib. Said Estrogen Receptor inhibitor is selected from Toremifene, Toremifene Citrate, Estriol, Propyl pyrazole triol, AZD9496, LY88074, GDC-0924 Racemate, CMP8, OSpemifene D4, Bazedoxifene, Pipendoxifene hydrochloride, Lasofoxifene Tartrate, 4-Hydroxytamoxifen, Clomiphene citrate, Mestranol, Idoxifene, 4,4-iminodiphenol, H3B-6545, H3B-6545 Hydrochloride, Gypenoside SVII, DPN, Prinaberel, Way-200070, Nitromifene, ERB-196, Elacestrant, LSZ-102, (E/Z)-4-Hydroxytamoxifen, Elacestrant dihydrochloride, GDC-0927, AZD-9833, Endoxifen, LY117018, Estradiol, WAY-204688, Tamoxifen, Tamoxifen Citrate or Fulvestrant. Said PI3k inhibitor is selected from Idelalisib (CAL-101), Copanlisib (BAY80-6946), buparlisib, AZD6482, GSK1059615, GSK2126458, GSK2636771, PQR309, PF-04691502, AMG319, 3-Methyladenine, ly294002, Wortmannin, Quercetin, α-Linolenic acid, Zandelisib, Pictilisib, IPI549, Dactolisib, Fimepinostat, SAR405, Duvelisib, PI-103, GDC-0077 or Alpelisib.

Preferably, said anti-cancer agents are one or more selected from the followings: Dabrafenib, Trametinib, Fulvestrant, Alpelisib.

In a preferred embodiment, said anti-cancer agents are one or more selected from the followings: Dabrafenib, Trametinib, Fulvestrant, Alpelisib.

In a preferred embodiment, said MDM2 inhibitor is the compound 2 and a pharmaceutically acceptable salt or solvate thereof, which has the structure of following formula:

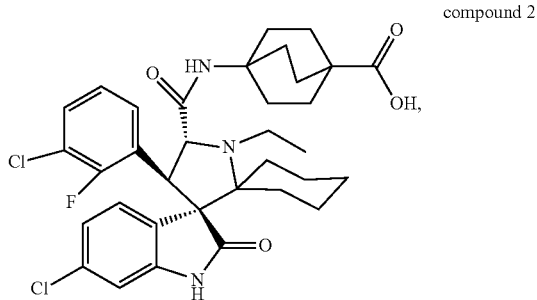 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]
compound 2 said anti-cancer agent is Azacitidine, Decitabine or Cytarabine.

In a preferred embodiment, said MDM2 inhibitor is the compound 2 and a pharmaceutically acceptable salt or solvate thereof, which has the structure of following formula:

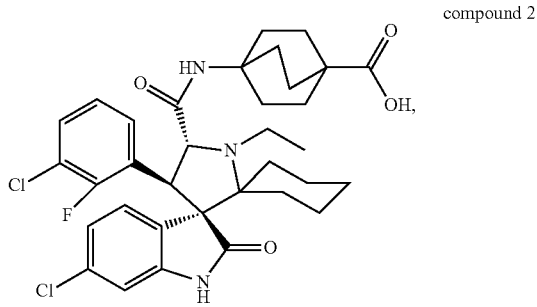 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]
compound 2 said anti-cancer agent is Homoharringtonine (HHT, Omacetaxine mepesuccinate).

In a preferred embodiment, said MDM2 inhibitor is the compound 2 and a pharmaceutically acceptable salt or solvate thereof, which has the structure of following formula:

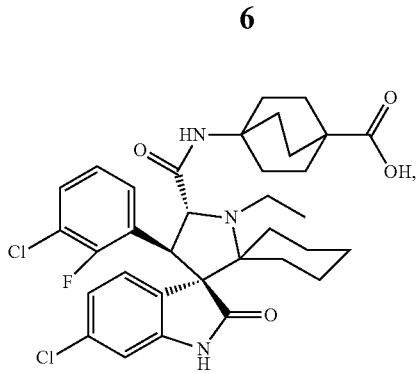
compound 2

In a preferred embodiment, Said anti-cancer agents are one or more selected from the followings: BRAF inhibitor, MEK inhibitor, Estrogen Receptor inhibitor, PI3k inhibitor. Said BRAF inhibitor is selected from Sorafenib, PLX-4720, Regorafenib (BAY 73-4506), GDC-0879, RAF265, SB590885, AZ 628, ML 7866dihydrochloride, PF-04880594, TAK-632, CEP-32496, RO5126766 or Dabrafenib. Said MEK inhibitor is selected from Pimasertib, PD184352, PD0325901, Selumetinib, PD98059, U0126-EtOH, TAK-733, Refametinib, GDC-0623, RO4987655, RO5126766 (CH5126766), SL-327, BI-847325 or Trametinib. Said Estrogen Receptor inhibitor is selected from Toremifene, Toremifene Citrate, Estriol, Propyl pyrazole triol, AZD9496, LY88074, GDC-0924 Racemate, CMP8, OSpemifene D4, Bazedoxifene, Pipendoxifene hydrochloride, Lasofoxifene Tartrate, 4-Hydroxytamoxifen, Clomiphene citrate, Mestranol, Idoxifene, 4,4-iminodiphenol, H3B-6545, H3B-6545 Hydrochloride, Gypenoside SVII, DPN, Prinaberel, Way-200070, Nitromifene, ERB-196, Elacestrant, LSZ-102, (E/Z)-4-Hydroxytamoxifen, Elacestrant dihydrochloride, GDC-0927, AZD-9833, Endoxifen, LY117018, Estradiol, WAY-204688, Tamoxifen, Tamoxifen Citrate or Fulvestrant. Said PI3k inhibitor is selected from Idelalisib (CAL-101), Copanlisib (BAY80-6946), buparlisib, AZD6482, GSK1059615, GSK2126458, GSK2636771, PQR309, PF-04691502, AMG319, 3-Methyladenine, ly294002, Wortmannin, Quercetin, α-Linolenic acid, Zandelisib, Pictilisib, IPI549, Dactolisib, Fimepinostat, SAR405, Duvelisib, PI-103, GDC-0077 or Alpelisib.

In a preferred embodiment, said MDM2 inhibitor is the compound 2 and a pharmaceutically acceptable salt or solvate thereof, which has the structure of following formula:

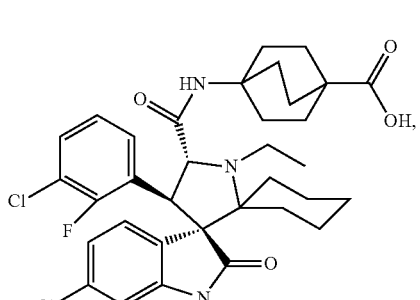
compound 2

In a preferred embodiment, said anti-cancer agents are one or more selected from the followings: Dabrafenib, Trametinib, Fulvestrant, Alpelisib.

Preferably, said anti-cancer agents are combination of Dabrafenib and Trametinib, combination of Fulvestrant and Alpelisib.

Preferably, the weight ratio of compound 2 and combination of anti-cancer agent Dabrafenib and Trametinib, or either of them is 100:1 to 1:100, comprising 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, 2:1, 0.8:1, 1:1, 1.6:1, 8:15, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95 or 1:100.

Or the weight ratio of compound 2 and combination of anti-cancer agent Fulvestrant and Alpelisib, or either of them is 100:1 to 1:100, comprising 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, 2:1, 0.8:1, 1:1, 1.6:1, 8:15, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95 or 1:100.

In a preferred embodiment, said pharmaceutical composition is in the forms of tablet, capsule, granule, syrup, powder, troche, sachet, cachet, elixir, suspension, emulsion, solution, syrup, aerosol, ointment, cream and injection.

In a preferred embodiment, the weight ratio (or mole ratio) of said MDM2 inhibitor or said anti-cancer agent is 100:1 to 1:100, comprising 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, 2:1, 0.8:1, 1:1, 1.6:1, 8:15, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95 or 1:100.

In another aspect of the present invention, provided is the use of said pharmaceutical composition in the preparation of a drug for preventing and/or treating a disease, wherein said disease is cancer.

In another aspect of the present invention, provided is a method for preventing and/or treating a disease, by administering said pharmaceutical composition to an individual in need thereof, comprising administering a prophylactically and/or therapeutically effective amount of said MDM2 inhibitor and an anti-cancer agent, wherein said disease is cancer.

In a preferred embodiment, said cancer is selected from adrenocortical carcinoma, advanced cancer, anal cancer, aplastic anemia, bile duct cancer, bladder cancer, bone cancer, bone metastasis, adult human brain/central nervous system tumors, childhood brain/central nervous system tumors, breast cancer, male breast cancer, childhood cancer, cancer of unknown primary, Castleman's disease, cervical cancer, colon/rectal cancer, endometrial cancer, esophageal cancer, Ewing's family of tumors, eye cancer, gallbladder cancer, gastrointestinal carcinoid, gastrointestinal stromal tumor (GIST), gestational trophoblastic disease, head and neck cancer, Hodgkin's disease, Kaposi's sarcoma, kidney cancer, laryngeal cancer and hypopharyngeal cancer, adult leukemia acute lymphoblastic leukemia (ALL), acute myeloid leukemia (AML), chronic lymphocytic leukemia (CLL), chronic myelocytic leukemia (CML), chronic myelomonocytic leukemia (CMML), childhood leukemia, liver cancer, non-small cell lung cancer, small cell lung cancer, lung cancer tumor, cutaneous lymphoma, malignant mesothelioma, multiple myeloma, myelodysplastic syndrome (MDS), cancer of the nasal cavity and nasal sinuses, nasopharyngeal cancer, neuroblastoma, non-Hodgkin's lymphoma, non-Hodgkin's lymphoma in children, oral and oropharyngeal cancer, osteosarcoma, ovarian cancer, pancreatic cancer, carcinoma of penis, pituitary tumor, prostate cancer, retinoblastoma, rhabdomyosarcoma, salivary gland cancer, adult soft tissue carcinoma, skin cancer, such as basal and squamous cell carcinomas, and melanoma, small intestine cancer, gastric cancer, testicular cancer, thymic cancer, thyroid cancer, uterine sarcoma, carcinoma of vagina, vulvar cancer, Waldenstrom macroglobulinemia and Wilms tumor.

In a preferred embodiment, the cancer is selected from acute myeloid leukemia (AML), acute lymphoblastic leukemia (ALL) myelodysplastic syndrome (MDS), melanoma and breast cancer.

In a preferred embodiment, said MDM2 inhibitor or a pharmaceutically acceptable salt or solvate thereof is administered at an amount of 0.0025-5000 mg/day. For example, it is administered at an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

In a preferred embodiment, said MDM2 inhibitor or a pharmaceutically acceptable salt or solvate thereof is administered at an amount of about 1 ng/kg to about 200 mg/kg, about 1 µg/kg to about 100 mg/kg or about 1 mg/kg to about 50 mg/kg per unit dosage, such as at an amount of about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg kg, about 225 µg/kg, about 250 µg kg, about 275 µg kg, about 300 µg/kg, about 325 µg kg, about 350 µg/kg, about 375 µg/kg, about 400 µg/kg, about 425 µg/kg, about 450 µg/kg, about 475 µg/kg, about 500 µg/kg, about 525 µg kg, about 550 µg/kg, about 575 µg kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg per unit dosage.

In a preferred embodiment, one or more of said anti-cancer agents or a pharmaceutically acceptable salt or solvate thereof are administered at an amount of about 0.0025-5000 mg/day, comprising at an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

In a preferred embodiment, one or more of said anti-cancer agents or a pharmaceutically acceptable salt or solvate thereof is administered at an amount of about 1 ng/kg to about 200 mg/kg, about 1 µg/kg to about 100 mg/kg or about 1 mg/kg to about 50 mg/kg per unit dosage, such as at an amount of about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg kg, about 225 µg/kg, about 250 µg kg, about 275 µg kg, about 300 µg/kg, about 325 µg kg, about 350 µg/kg, about 375 µg/kg, about 400 µg/kg, about 425 µg/kg, about 450 µg/kg, about 475 µg/kg, about 500 µg/kg, about 525 µg kg, about 550 µg/kg, about 575 µg kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg per unit dosage.

In a preferred embodiment, said MDM2 inhibitor and one or more of said anti-cancer agents are administered simultaneously, concurrently or in combination.

In a preferred embodiment, said MDM2 inhibitor and one or more of said anti-cancer agents are administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days.

In a preferred embodiment, said MDM2 inhibitor and one or more of said anti-cancer agents are administered continuously for one or more courses of treatment, comprising 1, 2, 3, 4, 5, 6, 7, 8, 9 or 10 courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and the interval between every two courses of treatment is 0, 1, 2, 3, 4, 5, 6, 7, 8, 9, 10 days, two weeks, three weeks or four weeks.

In a preferred embodiment, said MDM2 inhibitor and one or more of said anti-cancer agents are administered by an identical route (such as orally) or different routes (such as orally and parenterally (such as by injection) respectively), comprising orally, buccally, by inhalation of spray, sublingually, rectally, transdermally, via vaginal mucosa, transmucosally, by topical administration, by nasal or intestinal administration, by injection administration, such as intramuscular injection, subcutaneous injection, intramedullary injection, and intrathecally, by direct brain administration, by in situ administration, by subcutaneous, intraperitoneal, intravenous injection, intraarticular synovium, intrasternal, intrahepatic, intralesional, intracranial, abdominal cavity, nasal cavity, or intraocular injection or other drug delivery routes.

In another aspect of the present invention, provided is a kit comprising:
(a) a first component in a first container, wherein said first component comprises said MDM2 inhibitor and optionally a pharmaceutically acceptable carrier, diluent or excipient; and
(b) a second component in a second container, wherein said second component comprises one or more of said anti-cancer agents and optionally a pharmaceutically acceptable carrier, diluent or excipient.

BRIEF DESCRIPTION OF THE DRAWINGS

FIG. 9D. Summary analysis chart of the proportion of human CD45+ AML cells in spleen with compound 2.

FIG. 10. Analysis comparison chart of survival curve of compound 2 alone in two groups of animals.

(A) NOD SCID mice implanted with $1\times10^7$ MOLM-13 cells (n=15/group) three days after cell implantation are treated with a carrier, 50 mg/kg of compound 2 (each day PO for 7 days) and 2 mg/kg Aza (each day for 7 days) alone or in combination. The data are shown as the Kaplan-Meier curve depicting mouse survival. Logarithmic rank using Bonferroni multiple comparisons is used for survival comparison. *P<0.05.

(B) NOD SCID mice carrying a subcutaneous OCI-AML-3 tumor are treated with 50 mg/kg compound 2 (every other day PO for 15 days), 2 mg/kg Aza (each day IV for 7 days) and 1 mg/kg Dec (each day IV for 7 days) alone or in combination, and the tumor growth inhibition (TGI) is determined.

Figure 17:
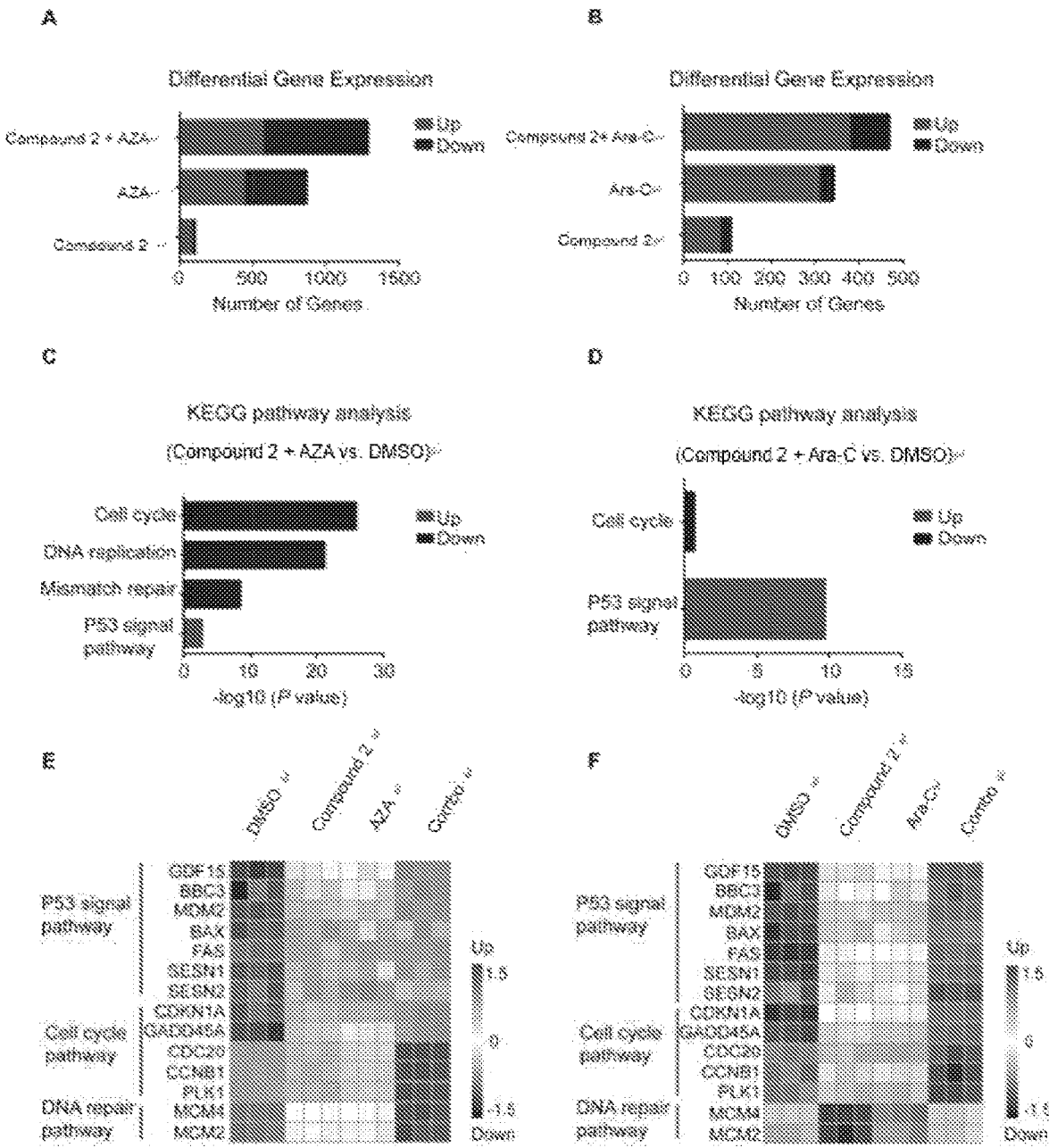

FIG. 17. RNA-Seq analysis of MOLM-13 cells treated with compound 2 and AZA or Ara-C alone or in combination. (A-B) Charts showing that after being affected by compound 2 and AZA or Ara-c alone or in combination for 24 hours, the number of differentially expressed genes is statistically significant. (C-D) After being treated with compound 2 and AZA or Ara-c in combination, the signaling pathway which is changed most significantly. (E-F) In MOLM-13 cells, with regard to compound 2 and AZA or Ara-C alone or in combination, the change of some p53 regulatory genes.

Figure 18:
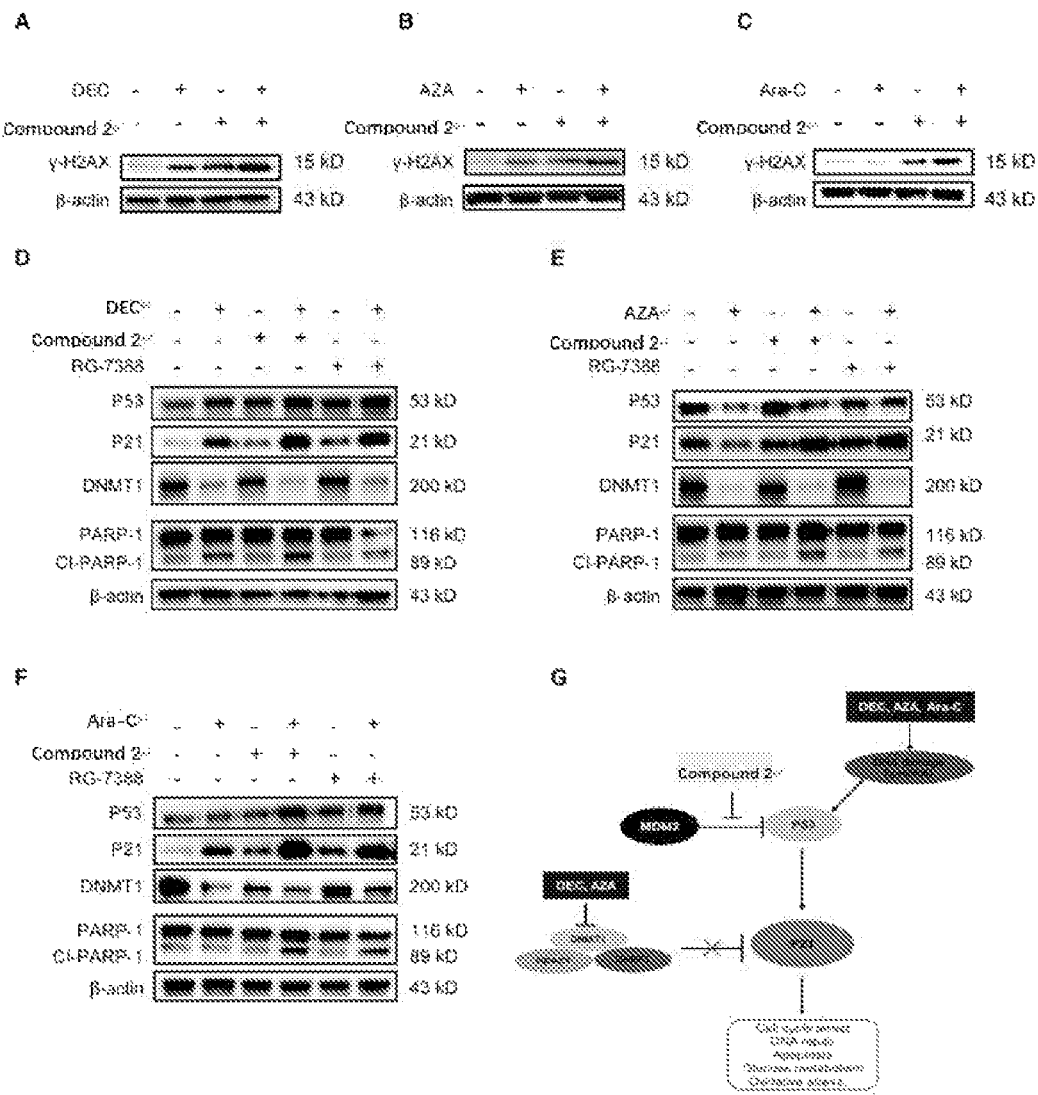

FIG. 18. AML cells are treated with compound 2 and DEC, AZA, and Ara-C in combination, DNA damage is induced synergistically, and P21 expression is up-regulated. (A-B) After being treated with DEC (100 nM) and AZA (0.33 µM) for 24 hours, then treated with new DEC (100 nM), AZA (0.33 µM) and compound 2 (40 nM) alone or in combination for another 24 hours, the expression of proteins in MOLM-13 cells. (C) After being treated with Ara-C (100 nM) or compound 2 (40 nM) alone or in combination for 48 hours, the expression of proteins in MOLM-13 cells. (D-F) As shown, after being treated with compound 2 (40 nM), RG-7388 (40 nM), DEC (100 nM), AZA (3 µM) and Ara-C alone or in combination for 48 hours, the expression of proteins in the MOLM-13 cells. B-actin is used for confirming that the loaded proteins are the same. (G) The mechanism of action of the proposed compound 2 and DEC, AZA or Ara-C in combination on AML cells. Its results represent three independent results. RG-7388 is used as the control, and B-actin is used for confirming that the loaded proteins are the same.

Figure 19A:
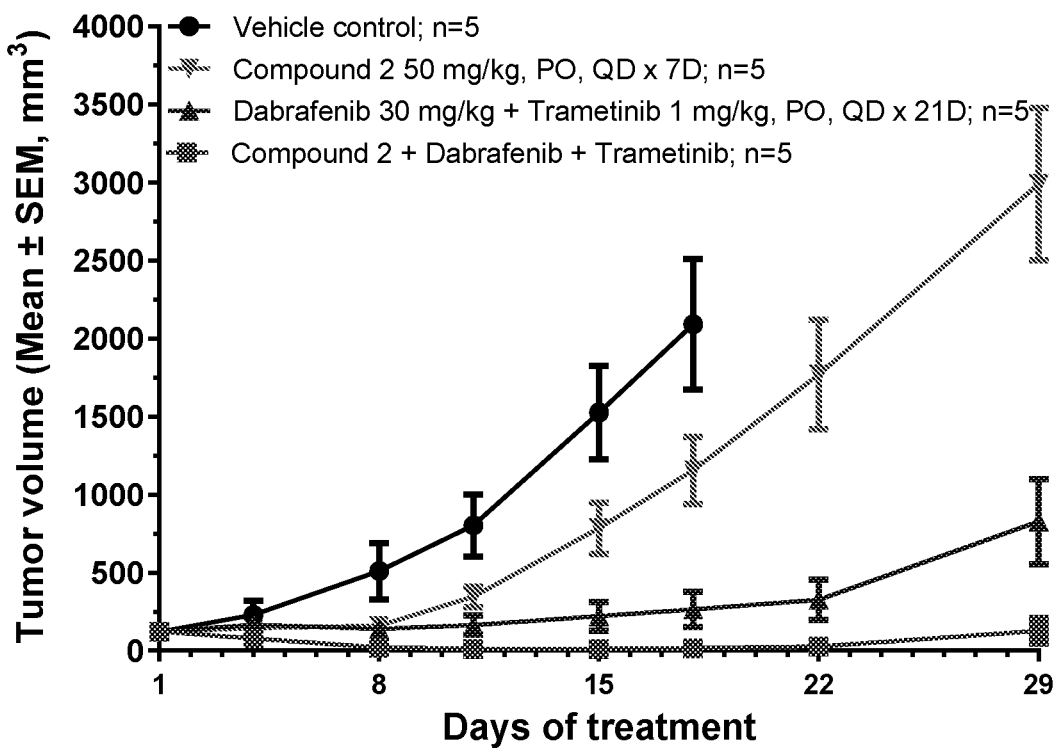
Figure 19B:
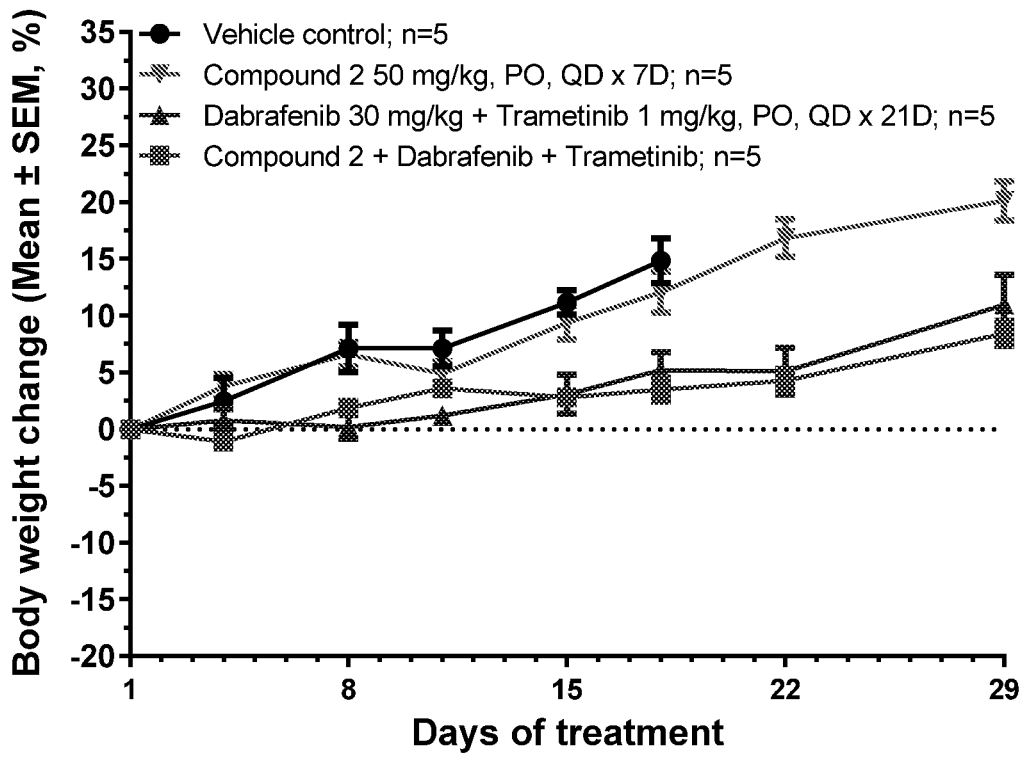

FIG. 19A-B. Tumor growth inhibiting curve chart and body weight change chart in mice (%) of compound 2 in combination with Dabrafenib and Trametinib to treat subcutaneous A375 cutaneous melanoma xenograft tumor in mice.

Figure 20A:
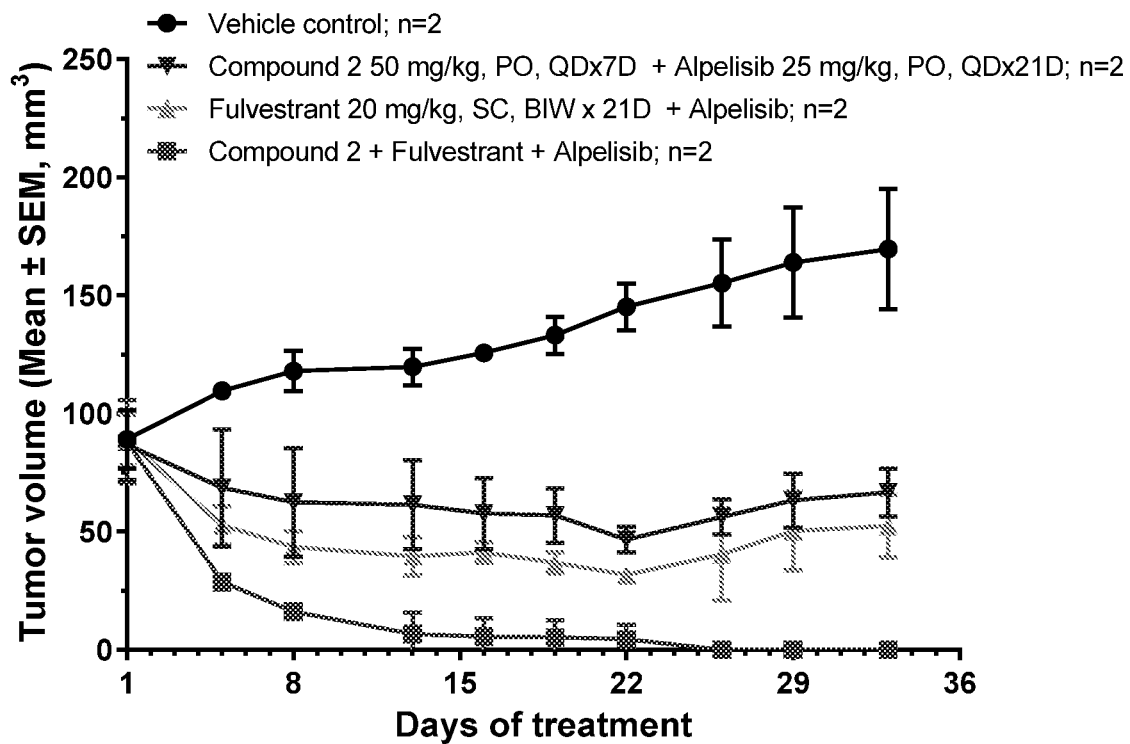
Figure 20B:
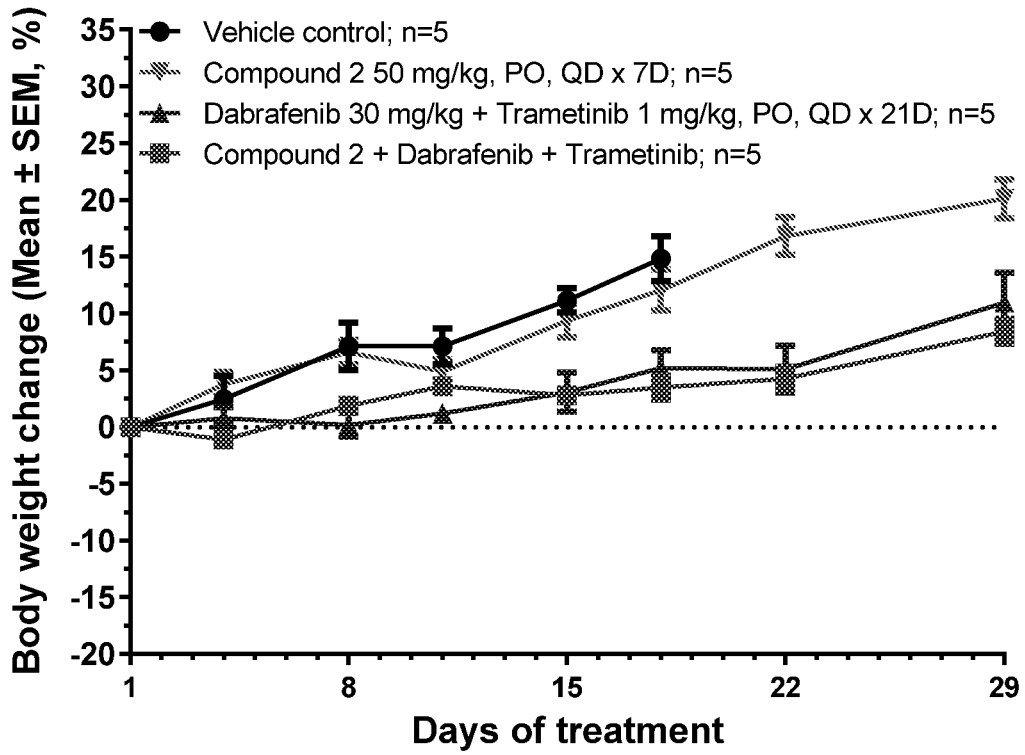

FIG. 20A-B. Tumor growth inhibiting curve chart and body weight change chart in mice (%) of compound 2 in combination with Fulvestrant and Alpelisib to treat subcutaneous MCF-7 ER$^+$ breast cancer xenograft tumor in mice.

DETAILED DESCRIPTION OF EMBODIMENTS

Unless defined otherwise, all technical and scientific terms used herein have the same meaning as commonly understood by a person skilled in the art. Referring to the technology used herein refers to the technology commonly understood in the art, including alterations of the technology or the equivalent replacements of the technology which are obvious to a person skilled in the art. Although it is believed that the following terms are well understood by a person skilled in the art, the following definitions are illustrated to better interpret the present invention.

The contents of all reference documents cited in the present application (including reference documents, authorized patents, published patent applications and unexamined patent applications), hereby incorporated by reference, are contained in the present invention explicitly. Unless specified otherwise, all technical and scientific terms used in the present invention is consistent with the meaning as well known by one of ordinary skill in the art.

Definitions

The terms "including", "comprising", "having", "containing" or "relating to" as used herein and other variant forms thereof herein are inclusive or open-ended, and do not exclude other elements or method steps not listed herein.

The term "MDM2 inhibitor" as used herein refers to a substance competing for the binding to MDM2, a substance affecting the binding of MDM2 to p53 protein, a substance inhibiting MDM2 activity, or a substance degrading MDM2 or a genetic tool lowering MDM2 level.

The term "MDM2 related protein" as used herein refers to a protein having at least 25% sequence homology with MDM2 and interacting with p53 or p53 related proteins and inhibiting p53 or p53 related proteins. The examples of MDM2 related proteins include, but are not limited to, MDMX.

The term "functional p53" as used herein refers to wild-type p53 or mutants or allelic variants of p53 expressed at a normal level, high level or low level, wherein these variants retain at least about 5% activity of the wild type p53, such as at least about 10%, about 20%, about 30%, about 40%, about 50%, or more activity of the wild type.

The term "p53-related protein" as used herein refers to a protein having at least 25% sequence homology with p53, said protein has the activity as a tumor suppressor, and will be inhibited by the interaction with MDM2 or MDM2-related proteins. The examples of the p53 related proteins include, but are not limited to, p63 and p73.

The term "pharmaceutically acceptable salt" as used herein refers to a salt of a free acid or free base, and is generally prepared by the reaction of a free base with a suitable organic or inorganic acid, or by the reaction of an acid with a suitable organic or inorganic base. The term can be used for any compound of the present invention. Representative salts include: acetate, benzene sulfonate, benzoate, bicarbonate, disulfate, bitartrate, borate, bromide, edetate calcium, camphor sulfonate, carbonate, chloride, clavulanate, citrate, dihydrochloride, edetate, ethanesulphonate, estolate, esylate, fumarate, gluceptate, gluconate, glutamate, glycol lylarsanilate, hexylresorcinate (hexylres or cinate), hydrabamine, hydrobromide, hydrochloride, hydroxynaphthoate, iodide, isethionate, lactate, lactobionate, laurate, malate, maleate, mandelate, mesylate, methobromide, methonitrate, methosulfate, monopotassium maleate salt, Mucate, naphthalenesulfonate, nitrate, N-methylglucamide, oxalate, pamoate (dihydroxynaphthalate), palmitate, pantothenate, phosphate/diphosphate, polygalacturonate, potassium salt, salicylate, sodium salt, stearate, subacetate, succinate, tannate, tartrate, teoclate, p-toluenesulphonate, triethiodide, trimethylamine salt and valerate. When an acidic substituent exists, such as —COOH, it can form an ammonium salt, morpholine salt, sodium salt, potassium salt, barium salt, calcium salt etc. for used in dosage forms. When a basic group exists (such as in limonoids or 1,1-dimethylbiguanide), such as amino or basic heteroaryl groups, such as pyridyl, it can form an acidic salt, such as hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, mesylate, esylate, picrate, etc. For the review of suitable salts, see Stahl and Wermuth, "Handbook of Pharmaceutical Salts: Properties, Selection, and Use" (Wiley-VCH, 2002).

The term "solvate" as used herein is the combination, physical binding, and/or solvation of the compounds related to the present invention and a solvent molecule, such as disolvate, monosolvate, and hemisolvate. The compounds involved in the present invention can form a solvate form with a pharmaceutically acceptable solvent, such as water, methanol, ethanol, etc., which does not significantly affect the pharmacological activity or toxicity of the compounds and can act as a pharmacologic equivalent.

One type of solvates is hydrate. "Hydrate" relates to a specific subset of the solvates, wherein the solvent molecule is water. Solvates generally can effect as a form of a pharmacologic equivalent. The preparation of the solvates are known in the art, see, e.g. M. Caira et al., J. Pharmaceut. Sci., 93(3):601-611(2004), which recorded a solvate of fluconazole prepared with ethyl acetate and water. The similar preparations of solvates, hemisolvates, hydrates, etc. are described in van Tonder et al., AAPS Pharm. Sci. Tech., 5(1): Article 12(2004) and A. L. Bingham et al., Chem. Commun. 603-604 (2001). The representative and non-limiting methods for preparing the solvates relate to dissolving the compounds of the present invention in a desired solvent (an organic solvent, and water or a mixture thereof) at a temperature above 20° C. to about 25° C., then cooling the solution at a rate which is sufficient to form a crystal, and separating the crystal by a known method (such as filtration). Analytical techniques (such as infrared spectroscopy) can be used to confirm that the solvent is present in the crystals of the solvate.

The "pharmaceutically acceptable carrier" as used herein refers to a diluent, auxiliary agent, excipient or vehicle which is administered with a therapeutic agent, and is suitable for contacting with tissue of human and/or other animals in a range of a reasonable medical judgment without excessive toxicity, stimulation, and allergic reaction or other problems or complications corresponding to a reasonable benefit/risk ratio.

Pharmaceutically acceptable carriers which can be used in the pharmaceutical composition or kit of the present invention include, but are not limited to, sterile liquids, such as water and oils, including oils derived from petroleum, animals, plants or synthetic sources, such as peanut oil, soybean oil, mineral oil, sesame oil, etc. When said pharmaceutical composition is administered intravenously, water is an exemplary carrier. Normal saline, and glucose and glycerol aqueous solution can also be used as a liquid carrier, especially for injection. Suitable drug excipients include starch, glucose, lactose, sucrose, gelatin, maltose, chalk, silica gel, sodium stearate, glyceryl monostearate, talc, sodium chloride, skim milk powder, glycerol, propanediol, water, ethanol, etc. Said pharmaceutical composition can also comprise a small amount of a wetting agent, emulsifier or pH buffer as desired. Oral preparation can comprise a standard carrier, such as pharmaceutical-grade mannitol, lactose, starch, magnesium stearate, sodium saccharin, cellulose, magnesium carbonate, etc. For example, examples of suitable pharmaceutically acceptable carriers are described in Remington's Pharmaceutical Sciences (1990).

The various components of the pharmaceutical composition and kit of the present invention can act systemically and/or locally. For this purpose, they can be administered by suitable routes, such as by injection (such as intravenous, intra-arterial, subcutaneous, intraperitoneal, intramuscular injection, comprising instillation) or transdermal administration; or administered orally, buccally, nasally, transmucosally, locally, and in the form of ophthalmic preparation, or administered by inhalation. For these administration routes, the various components of the pharmaceutical composition and kit of the present invention can be administered in suitable dosage forms.

The term "container" as used herein is a container for containing a pharmaceutical component. This container can be used for preparation, storage, transportation and/or independent/bulk sales, which are intended to encompass bottle, pot, vial, flask, syringe, and tube (such as for cream article), or any other container for preparing, containing, storing or distributing pharmaceutical products.

The term "prevention" as used herein refers to when being used for diseases or conditions (such as cancer), compared with the individuals without administration of a compound or drug (such as the claimed pharmaceutical composition of the present application), said compound or drug can reduce the frequency of medical condition symptoms or delay the onset thereof in the individuals.

The term "treatment" as used herein refers to alleviating, relieving or ameliorating the symptoms of diseases or conditions, ameliorating the symptoms caused by potential metabolisms, inhibiting diseases or symptoms, such as stopping the progress of diseases or conditions, relieving diseases or conditions, causing the fade out of diseases or conditions, relieving the state of illness caused by diseases or conditions, or stopping the symptoms of diseases or conditions. The term "treatment" also comprises relapse prevention or stage prevention, and treatment of acute or chronic signs, symptoms and/or dysfunctions. Treatment can be symptom oriented, such as to inhibit symptoms. It can be realized in a short time, is oriented during the mid-term, or can be a long-term treatment, such as in the context of maintenance treatment.

The term "cancer" as used herein refers to a neoplasm or tumor caused by abnormal and uncontrolled cell growth. Non-limiting examples comprise those exemplary cancer described in the detailed description of the invention. The term "cancer" comprises diseases simultaneously involving premalignant cancer cells and malignant cancer cells.

The term "individual" as used herein comprises human or non-human animals. Exemplary human individuals comprise human individuals with diseases (such as diseases described herein) (known as patients) or normal individuals. "Non-human animals" in the present invention comprise all vertebrates, such as non-mammals (such as birds, amphibians, and reptiles) and mammals, such as non-human primates, farm animals and/or domesticated animals (such as sheep, dogs, cats, cows, pigs, etc.). When the individual is a human patient (generally the weight is calculated as 60 kg), unless stated otherwise, the dosage described in the present invention can be obtained by the conversion using the conversion factors with experimental animals (for example, human dosage=mouse dosage/12.3) (reference can be made to Kin Tam. "Estimating the "First in human" dose-a revisit with particular emphasis on oncology drugs", ADMET & DMPK 1(4)(2013)63-75). A person skilled in the art can reasonably adjust said dosage according to general knowledge, specific individual weight, the type of diseases, severity degree and other factors, and all these adjusted technical solutions fall within the scopes of protection of the claimed technical solutions of the present invention.

The term "effective amount" or "prophylactically and/or therapeutically effective amount" as used herein refers to an amount (for example dosage) of the administered drug or compound sufficient to alleviate one or more symptoms of treated diseases or conditions to some extent. The result can be shrinking and/or alleviating the cause of diseases or conditions or any other desired change of the biological system. For example, the "effective amount" for therapeutic use is the amount of a drug or compound (such as the claimed pharmaceutical composition of the present application) providing the significant alleviation of the clinical symptoms of diseases or conditions without excessive toxic and side effects. The effective amount of said drug can reduce (i.e. delay to some extent and preferably stop) the proliferation of harmful cells; reduce the number of cancer cells; reduce tumor size; inhibit (i.e. delay to some extent and preferably stop) cancer cells infiltrating into a peripheral organ; inhibit (i.e. delay to some extent and preferably stop) tumor metastasis; inhibit tumor growth to some extent; reduce the interaction of MDM2 and MDM2 related proteins with p53 and p53 related proteins; and/or relieve one or more of the symptoms related to cancer to some extent by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. With respect to the administered compound or composition stopping growth and/or killing existing cancer cells, it can have cell inhibitive ability and/or cytotoxicity.

The terms "concurrent administration", "combination administration", "simultaneous administration" and similar phrases as used herein refer to the treated subject who is administered concurrently with two or more agents. The term "concurrently" refers to administering each agent simultaneously or in any sequence orderly at different time points. However, if they are not administered simultaneously, then it means that they are administered to an individual in a certain sequence and are close enough in time to provide a desired therapeutic effect and can has a synergistic effect. For example, the MDM2 inhibitor of the present invention (such as compound 1 and compound 2) can be administered with an anti-cancer agent simultaneously, or in any sequence orderly at different time points. The MDM2 inhibitor of the present invention and an anti-cancer agent can be administered separately in any suitable form and by any suitable routes. The MDM2 inhibitor of the present invention and an anti-cancer agent are not administered concurrently, and it should be understood that they can be administered to a subject in need thereof in any sequence. For example, the MDM2 inhibitor of the present invention can be administered to an individual in need thereof before (such as 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), simultaneously with or after (such as 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) administering the treatment mode (such as radiotherapy) of the anti-cancer agent. In various embodiments, the interval between the MDM2 inhibitor of the present invention (such as compound 1 and compound 2) and an anti-cancer agent which are administered is 1 minute, 10 minutes, 30 minutes, less than 1 hour, 1 hour, 1 hour to 2 hours, 2 hours to 3 hours, 3 hours to 4 hours, 4 hours to 5 hours, 5 hours to 6 hours, 6 hours to 7 hours, 7 hours to 8 hours, 8 hours to 9 hours, 9 hours to 10 hours, 10 hours to 11 hours, 11 hours to 12 hours, no more than 24 hours or no more than 48 hours. In one embodiment, the components of the combined treatment are administered with an interval of 1 minute to 24 hours.

The term "dosage" as used herein refers to the weight of an active substance (such as milligram (mg)) per kilogram (kg) of individual weight.

The term "$IC_{50}$" as used herein refers to the 50% inhibition of the maximum effect obtained in the experiment for measuring such effect, such as the amount, concentration or dosage of specific test compound or drug of BCL-2 or MDM2 inhibition.

The term "room temperature" as used herein refers to 25° C.±1° C. At the same time, if it does not specifically indicate the experimental temperature, it is all room temperature.

The term "about" as used herein refers to ±10%, more preferably ±5% and most preferably ±2% of the numerical value modified by the term, and therefore, a person skilled in the art can clearly determine the range of term "about" according to the modified numerical value.

The term "$C_{1-4}$alkyl" refers to any linear or branched group containing 1-4 carbon atoms, such as methyl, ethyl, n-propyl, isopropyl, n-butyl, isobutyl, tert-butyl, sec-butyl, etc.

The term "$C_{1-3}$alkyl" refers to any linear or branched group containing 1-3 carbon atoms, such as methyl, ethyl, n-propyl, isopropyl, etc.

The term "$C_{1-3}$alkene" refers to a group obtained by removing one hydrogen atom from the above-mentioned "$C_{1-3}$alkyl".

The term "heterocyclic ring" as used herein refers to a heteroaryl ring system and heterocycloalkyl ring. The term "$C_{3-8}$cycloalkyl" refers to a monocyclic or bicyclic, saturated or partially unsaturated ring system which contains three to eight carbon atoms, comprising cyclopropyl, cyclobutyl, cyclopentyl, cyclohexyl, cycloheptyl, and cyclooctyl, for example, said ring system is optionally substituted by one or more, and generally one to three of independently selected halo, trifluoromethyl, trifluoromethoxy, hydroxy, alkoxy, nitro, cyano, alkylamino, or amino. The term "heterocycloalkyl" refers to a monocyclic or bicyclic, saturated or partially unsaturated ring system which contains 4 to 12 atoms in total, wherein one to five of said atoms are independently selected from nitrogen, oxygen, and sulfur, and the remaining atoms are carbon. The non-limiting examples of heterocycloalkyl are azetidinyl, pyrrolidinyl, piperidinyl, piperazinyl, dihydropyrrolyl, morpholinyl, thiomorpholinyl, dihydropyridinyl, oxepanyl, dioxepinyl, thiepanyl, and diazepanyl, each of which is optionally substituted by one or more, and generally one to three of independently selected halo, C1-6 alkyl, C1-6 alkoxy, cyano, amino, carbamoyl, nitro, carboxyl, C2-7 alkenyl, C2-7 alkynyl and the like on atoms of the ring. The term "halogen" or "halo" refers to VIIA group elements and atoms in the periodic system, comprising fluorine (F), chlorine (Cl), bromine (Br), iodine (I), astatine (At), and tennessine (Ts).

Similar terms "heterocyclic ring", "heterocycloalkyl", "$C_{3-8}$cycloalkyl" and "halogen" and the like as used herein have the general meaning in the art, and one of ordinary skill in the art can know their meanings by general knowledge or making reference to the prior art (such as WO 2015/161032, which is incorporated in the present invention by reference in its entirety).

Pharmaceutical Composition and Kit

A first aspect of the present invention relates to a pharmaceutical composition comprising an MDM2 inhibitor and an anti-cancer agent and optionally a pharmaceutically acceptable carrier, diluent or excipient. The disclosed MDM2 inhibitor inhibits the interaction of p53 or p53 related proteins with MDM2 or MDM2 related proteins. The MDM2 inhibitor of the present invention sensitizes cells to induce apoptosis and/or cell cycle arrest by inhibiting the negative effects of MDM2 or MDM2 related proteins on p53 or p53 related proteins.

In a preferred embodiment, said MDM2 inhibitor is the compound of following structural formula or a pharmaceutically acceptable salt or solvate thereof:

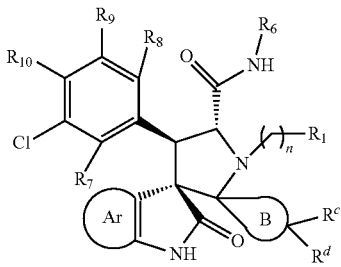

wherein:

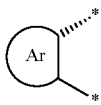

is selected from the group consisting of:

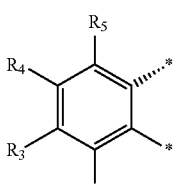 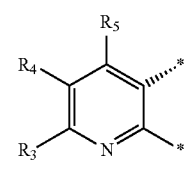

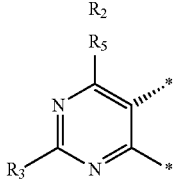 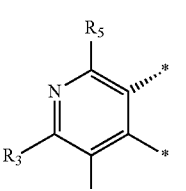 and

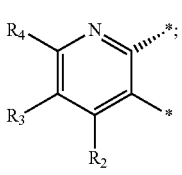

B is a $C_{4-7}$ carbocyclic ring;

$R_1$ is H, substituted or unsubstituted $C_{1-4}$alkyl, substituted or unsubstituted $C_{3-8}$cycloalkyl, substituted or unsubstituted heterocycloalkyl, $OR^a$ or $NR^aR^b$;

n is 0, 1 or 2;

$R_2$, $R_3$, $R_4$, $R_5$, $R_7$, $R_8$, $R_9$, and $R_{10}$ are independently selected from the group consisting of H, F, Cl, $CH_3$, and $CF_3$;

$R_6$ is

$R^a$ is hydrogen or substituted or unsubstituted $C_{1-4}$alkyl;

$R^b$ is hydrogen or substituted or unsubstituted $C_{1-4}$alkyl;

$R^c$ and $R^d$ are substituents on one carbon atom of ring B, wherein $R^c$ is H, $C_{1-3}$alkyl, $C_{1-3}$alkylene-$OR^a$, $OR^a$, or halo;

$R^d$ is H, $C_{1-3}$alkyl, $C_{1-3}$alkylene-$OR^a$, $OR^a$, or halo; or $R^c$ and $R^d$ are taken together with the carbon to which they are attached to form a 4- to 6-membered spirocyclic substituent, which optionally contains an oxygen or nitrogen atom; and $R^e$ is —C(=O)$OR^a$, —C(=O)$NR^aR^b$, or —C(=O)NHSO$_2$CH$_3$.

In a preferred embodiment, wherein

is

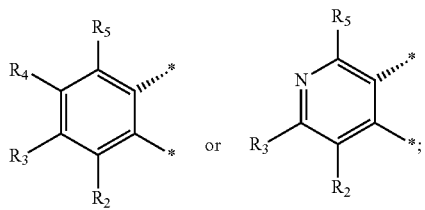

B is

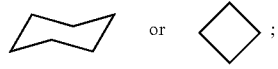

$R^c$ and $R^d$ are F and F, H and H, OH and $CH_3$, $CH_3$ and $CH_3$, $CH_3$ and OH, H and OH, $CH_2CH_3$ and $CH_2CH_3$, and $CH_2OH$ and $CH_2OH$.

In a preferred embodiment, —(CH$_2$)$_n$R$_1$ is H, CH$_3$, or CH$_2$CH$_3$.

In a preferred embodiment, $R_2$ is H.

In a preferred embodiment, $R_3$ is halo.

In a preferred embodiment, $R_4$ and $R_5$ are both H.

In a preferred embodiment, $R_7$ is halo.

In a preferred embodiment, each of $R_8$, $R_9$, and $R_{10}$ is H.

In a preferred embodiment, $R^e$ is —C(=O)OH, —C(=O)NH$_2$ or —C(=O)NHSO$_2$CH$_3$.

In a preferred embodiment, $R_c$ and $R_d$ are taken together with ring B form

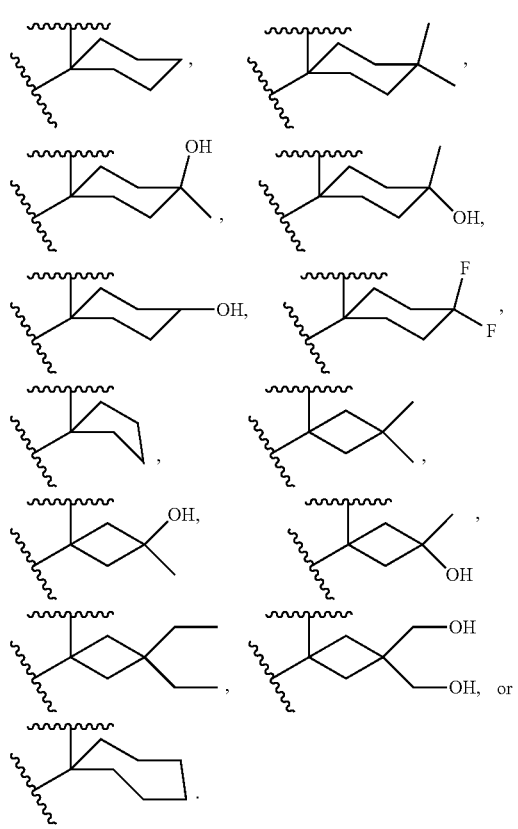
In a preferred embodiment, $R_6$ is:
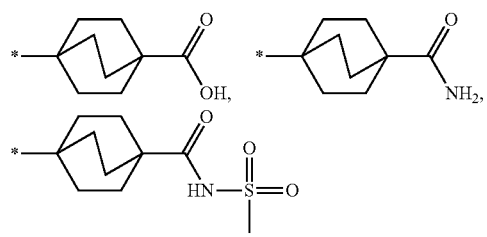
In a preferred embodiment, the MDM2 inhibitor is selected from:
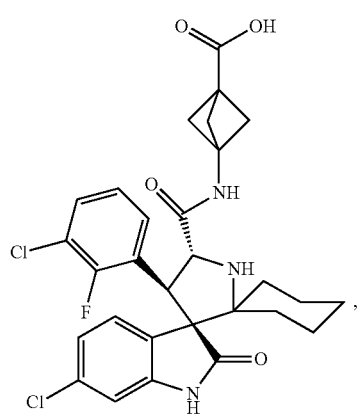
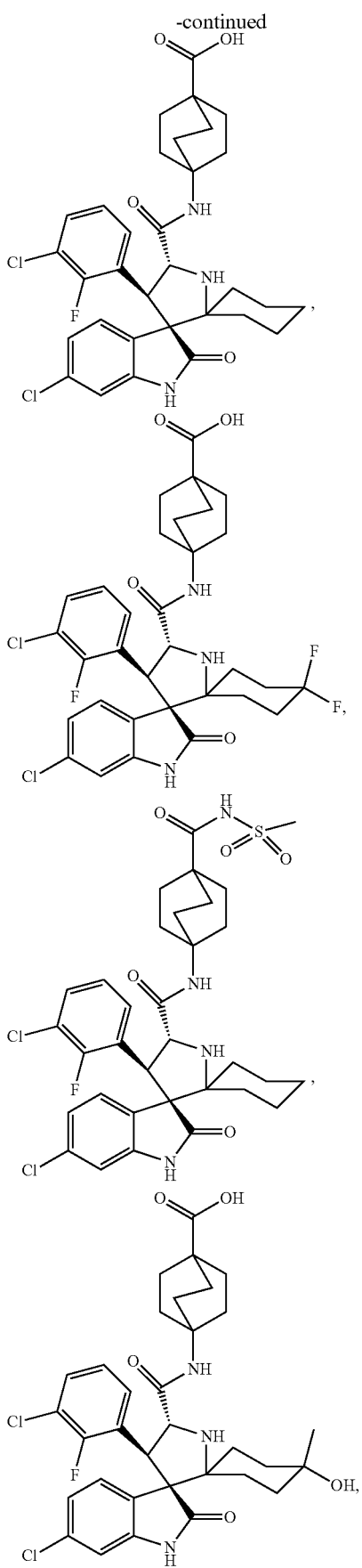

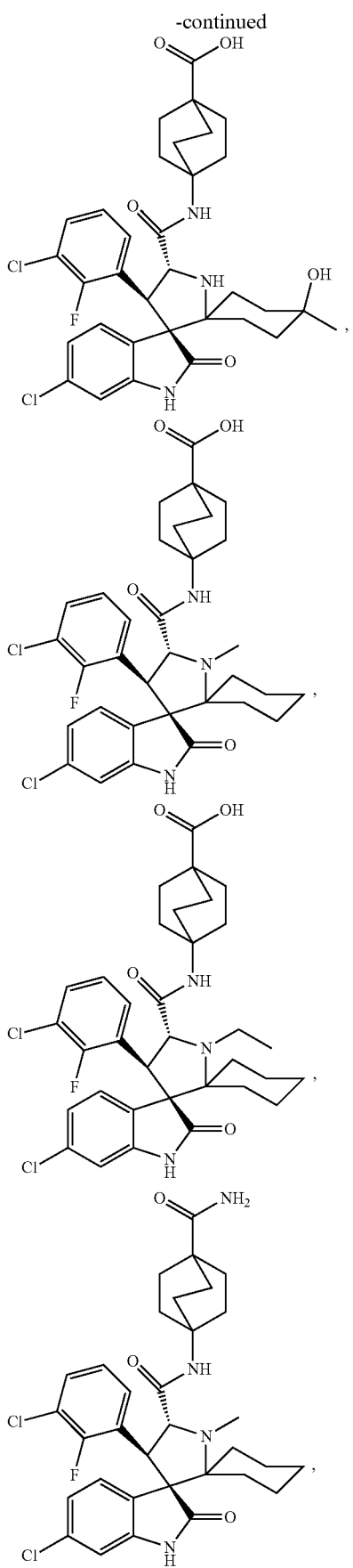

-continued

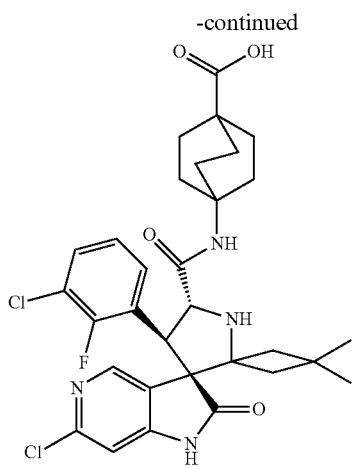

and

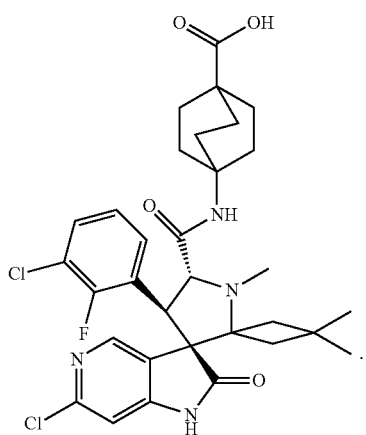

In a preferred embodiment, the MDM2 inhibitor is the compound 1 and a pharmaceutically acceptable salt or solvate thereof:

compound 1

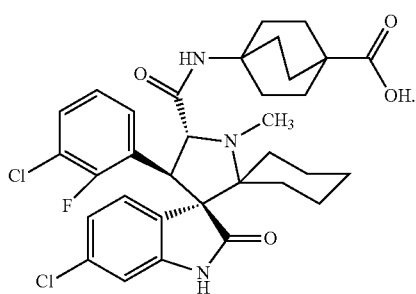

In a preferred embodiment, the MDM2 inhibitor is the compound 2 and a pharmaceutically acceptable salt or solvate thereof:

compound 2

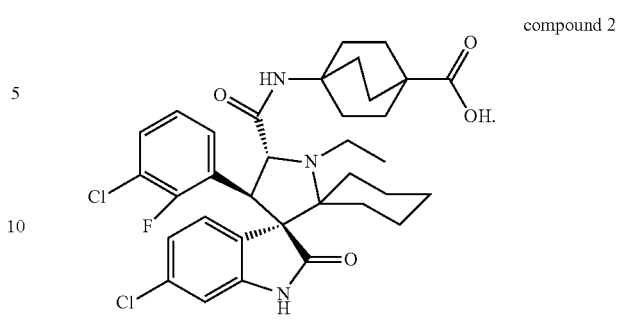

In a preferred embodiment, the anti-cancer agent is selected from chemotherapeutic drugs, comprising Homoharringtonine, demethylation drugs and/or antimetabolites; preferably, said demethylation drugs comprising Azacitidine, Decitabine, Zebularine, Fazadinium or dihydro-5'-cytidine; and preferably, said antimetabolites comprising Cytarabine, ancitabine, Gemcitabine or Troxacitabine.

In a preferred embodiment, said MDM2 inhibitor is the compound 2 and a pharmaceutically acceptable salt or solvate thereof, which has the structure of following formula:

compound 2

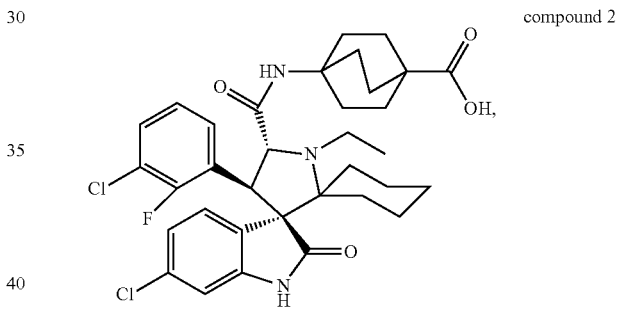

said anti-cancer agent is Azacitidine, Decitabine and/or Cytarabine, and has following structures:

Azacitidine, CAS number: 320-67-2,

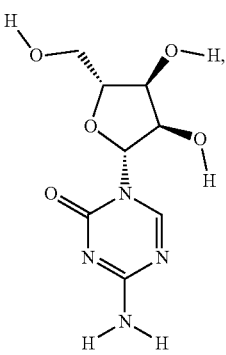

Azacitidine

Decitabine, CAS number: 2353-33-5,

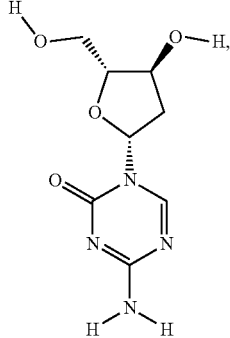

Decitabine

Cytarabine, CAS number: 147-94-4,

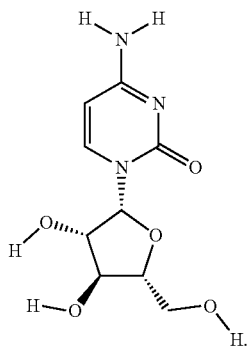

Cytarabine

Dabrafenib, Trametinib, fulvestrant and alpelisib.

In a preferred embodiment, said MDM2 inhibitor is the compound 2 and a pharmaceutically acceptable salt or solvate thereof, which has the structure of following formula:

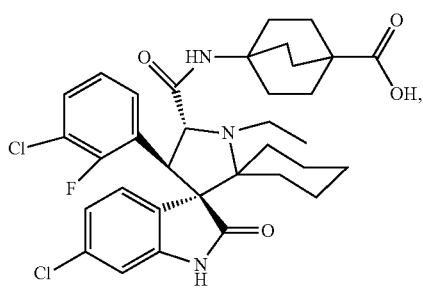

compound 2 said anti-cancer agent is Homoharringtonine (HHT, Omacetaxine mepesuccinate, HHRT), CAS number: 26833-87-4, and has following structures:

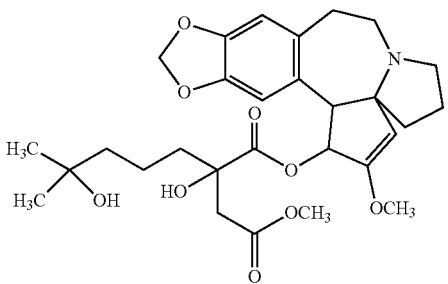

Homoharringtonine, Azacitidine, Decitabine, and/or Cytarabine used in the present invention are all commercially available, and can be purchased from Selleck official website.

In a preferred embodiment, the pharmaceutical composition or said MDM2 inhibitor or said anti-cancer agent is in the forms of tablet, capsule, granule, syrup, powder, troche, sachet, cachet, elixir, suspension, emulsion, solution, syrup, aerosol, ointment, cream and injection.

In a preferred embodiment, said MDM2 inhibitor and anti-cancer agent are each in the form of individual preparations.

Provided in the present invention is a kit comprising:
(a) a first component in a first container, wherein said first component comprises said MDM2 inhibitor and optionally a pharmaceutically acceptable carrier, diluent or excipient, said MDM2 inhibitor preferably is the compound specifically described in the first aspect of the present invention and a pharmaceutically acceptable salt or solvate thereof, such as compound 1 and compound 2; and
(b) a second component in a second container, wherein said second component comprises one or more of said anti-cancer agents and optionally a pharmaceutically acceptable carrier, diluent or excipient, said anti-cancer agents preferably are Homoharringtonine, demethylation drugs and/or antimetabolites specifically described in the first aspect of the present invention, such as Azacitidine, Decitabine, and/or Cytarabine.

Use and Treatment Methods

A second aspect of the present invention relates to the use of said pharmaceutical composition in the preparation of a drug for preventing and/or treating a disease, wherein said disease is cancer.

In a preferred embodiment, said pharmaceutical composition comprises an MDM2 inhibitor and an anti-cancer agent and optionally a pharmaceutically acceptable carrier, diluent or excipient. The MDM2 inhibitor preferably is the compound specifically described in the first aspect of the present invention and a pharmaceutically acceptable salt or solvate thereof, such as compound 1 and compound 2. The anti-cancer agents preferably are Homoharringtonine, demethylation drugs and/or antimetabolites specifically described in the first aspect of the present invention, such as Azacitidine, Decitabine, and/or Cytarabine.

In a preferred embodiment, said cancer is selected from adrenocortical carcinoma, advanced cancer, anal cancer, aplastic anemia, bile duct cancer, bladder cancer, bone cancer, bone metastasis, adult human brain/central nervous system tumors, childhood brain/central nervous system tumors, breast cancer, male breast cancer, childhood cancer, cancer of unknown primary, Castleman's disease, cervical cancer, colon/rectal cancer, endometrial cancer, esophageal cancer, Ewing's family of tumors, eye cancer, gallbladder cancer, gastrointestinal carcinoid, gastrointestinal stromal tumor (GIST), gestational trophoblastic disease, head and neck cancer, Hodgkin's disease, Kaposi's sarcoma, kidney cancer, laryngeal cancer and hypopharyngeal cancer, adult leukemia acute lymphoblastic leukemia (ALL), acute myeloid leukemia (AML), chronic lymphocytic leukemia (CLL), chronic myelocytic leukemia (CML), chronic myelomonocytic leukemia (CMML), childhood leukemia, liver cancer, non-small cell lung cancer, small cell lung cancer, lung cancer tumor, cutaneous lymphoma, malignant mesothelioma, multiple myeloma, myelodysplastic syndrome (MDS), cancer of the nasal cavity and nasal sinuses, nasopharyngeal cancer, neuroblastoma, non-Hodgkin's lymphoma, non-Hodgkin's lymphoma in children, oral and oropharyngeal cancer, osteosarcoma, ovarian cancer, pancreatic cancer, carcinoma of penis, pituitary tumor, prostate cancer, retinoblastoma, rhabdomyosarcoma, salivary gland cancer, adult soft tissue carcinoma, skin cancer, such as basal and squamous cell carcinomas, and melanoma, small intestine cancer, gastric cancer, testicular cancer, thymic cancer, thyroid cancer, uterine sarcoma, carcinoma of vagina, vulvar cancer, Waldenstrom macroglobulinemia and Wilms tumor.

In a more preferred embodiment, the cancer is selected from acute myeloid leukemia (AML), acute lymphoblastic leukemia (ALL) and myelodysplastic syndrome (MDS), melanoma and breast cancer.

In addition, the present invention relates to use of compound 2 alone and in combination with Azacitidine or Cytarabine in the preparation of a drug for treating adult relapsed or refractory acute myeloid leukemia and relapsed or refractory high risk/extremely high risk myelodysplastic syndrome.

Another, the present invention relates to use of compound 2 in the preparation of a drug for treating myelodysplastic syndrome (MDS).

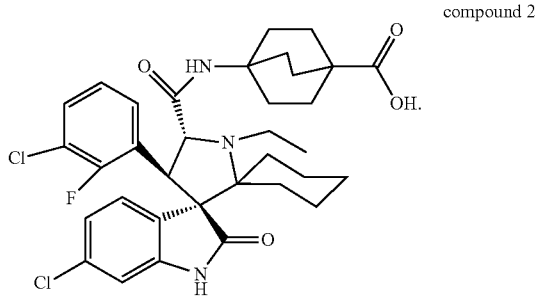 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

compound 2

Or, the present invention relates to use of compound 2 alone and in combination with Dabrafenib and Trametinib in the preparation of a drug for treating melanoma. Preferably, The weight ratio of compound 2 and combination of Dabrafenib and Trametinib is 50:30:1.

Or, the present invention relates to use of compound 2 alone and in combination with Fulvestrant and Alpelisib in the preparation of a drug for treating breast cancer. Preferably, The weight ratio of compound 2 and combination of Fulvestrant and Alpelisib is 50:20:25.

A third aspect of the present invention relates to a method for preventing and/or treating a disease, by administering said pharmaceutical composition to an individual in need thereof, comprising administering a prophylactically and/or therapeutically effective amount of said MDM2 inhibitor and an anti-cancer agent, wherein said disease is cancer.

In a preferred embodiment, said pharmaceutical composition comprises an MDM2 inhibitor and an anti-cancer agent and optionally a pharmaceutically acceptable carrier, diluent or excipient. The MDM2 inhibitor preferably is the compound specifically described in the first aspect of the present invention and a pharmaceutically acceptable salt or solvate thereof, such as compound 2. The anti-cancer agents preferably are Homoharringtonine, demethylation drugs and/or antimetabolites specifically described in the first aspect of the present invention, such as Azacitidine, Decitabine, and/or Cytarabine. For example, compound 2 and Azacitidine, compound 2 and Decitabine, and compound 2 and Cytarabine are administered.

In a preferred embodiment, said cancer is selected from adrenocortical carcinoma, advanced cancer, anal cancer, aplastic anemia, bile duct cancer, bladder cancer, bone cancer, bone metastasis, adult human brain/central nervous system tumors, childhood brain/central nervous system tumors, breast cancer, male breast cancer, childhood cancer, cancer of unknown primary, Castleman's disease, cervical cancer, colon/rectal cancer, endometrial cancer, esophageal cancer, Ewing's family of tumors, eye cancer, gallbladder cancer, gastrointestinal carcinoid, gastrointestinal stromal tumor (GIST), gestational trophoblastic disease, head and neck cancer, Hodgkin's disease, Kaposi's sarcoma, kidney cancer, laryngeal cancer and hypopharyngeal cancer, adult leukemia acute lymphoblastic leukemia (ALL), leukemia-acute myeloid leukemia (AML), chronic lymphocytic leukemia (CLL), leukemia-chronic myelocytic leukemia (CML), leukemia-chronic myelomonocytic leukemia (CMML), childhood leukemia, liver cancer, lung cancer-non-small cell cancer, lung cancer-small cell lung cancer, lung cancer tumor, cutaneous lymphoma, malignant mesothelioma, multiple myeloma, myelodysplastic syndrome (MDS), cancer of the nasal cavity and nasal sinuses, nasopharyngeal cancer, neuroblastoma, non-Hodgkin's lymphoma, non-Hodgkin's lymphoma in children, oral and oropharyngeal cancer, osteosarcoma, ovarian cancer, pancreatic cancer, carcinoma of penis, pituitary tumor, prostate cancer, retinoblastoma, rhabdomyosarcoma, salivary gland cancer, adult soft tissue carcinoma, skin cancer, such as basal and squamous cell carcinomas, and melanoma, small intestine cancer, gastric cancer, testicular cancer, thymic cancer, thyroid cancer, uterine sarcoma, carcinoma of vagina, vulvar cancer, Waldenstrom macroglobulinemia and Wilms tumor.

In a more preferred embodiment, the cancer is selected from acute myeloid leukemia (AML), acute lymphoblastic leukemia (ALL) and myelodysplastic syndrome (MDS), melanoma and breast cancer.

In a preferred embodiment, said MDM2 inhibitor or a pharmaceutically acceptable salt or solvate thereof is administered at an amount of 0.0025-5000 mg/day. For example, it is administered at an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day, and a range between each amount, such as 1 mg-2000 mg, 1 mg-1000 mg, 30 mg-900 mg, 30 mg-800 mg, 30 mg-900 mg, 30 mg-800 mg, 30 mg-700 mg, 30 mg-600 mg, 30 mg-500 mg, 30 mg-490 mg, 30 mg-487 mg, etc.

In a preferred embodiment, said MDM2 inhibitor or a pharmaceutically acceptable salt or solvate thereof is administered at an amount of about 1 ng/kg to about 200 mg/kg, about 1 µg/kg to about 100 mg/kg or about 1 mg/kg to about 50 mg/kg per unit dosage, such as at an amount of about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg kg, about 225 µg/kg, about 250 µg kg, about 275 µg kg, about 300 µg/kg, about 325 µg kg, about 350 µg/kg, about 375 µg/kg, about 400 µg/kg, about 425 µg/kg, about 450 µg/kg, about 475 µg/kg, about 500 µg/kg, about 525 µg kg, about 550 µg/kg, about 575 µg kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg per unit dosage. For example, compound 2 or a pharmaceutically acceptable salt or solvate thereof at an amount of about 20 mg/kg, 30 mg/kg, 50 mg/kg, and 80 mg/kg per unit dosage is administered to an individual.

In a preferred embodiment, one or more of said anti-cancer agents or a pharmaceutically acceptable salt or solvate thereof are administered at an amount of about 0.0025-5000 mg/day, comprising at an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day, and a range between each amount, such as 1 mg-2000 mg, 1 mg-1000 mg, 30 mg-900 mg, 30 mg-800 mg, 30 mg-900 mg, 30 mg-800 mg, 30 mg-700 mg, 30 mg-600 mg, 30 mg-500 mg, 30 mg-490 mg, 30 mg-487 mg, etc.

In a preferred embodiment, one or more of said anti-cancer agents or a pharmaceutically acceptable salt or solvate thereof is administered at an amount of about 1 ng/kg to about 200 mg/kg, about 1 µg/kg to about 100 mg/kg or about 1 mg/kg to about 50 mg/kg per unit dosage, such as at an amount of about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg kg, about 225 µg/kg, about 250 µg kg, about 275 µg kg, about 300 µg/kg, about 325 µg kg, about 350 µg/kg, about 375 µg/kg, about 400 µg/kg, about 425 µg/kg, about 450 µg/kg, about 475 µg/kg, about 500 µg/kg, about 525 µg kg, about 550 µg/kg, about 575 µg kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg per unit dosage. For example, Azacitidine or a pharmaceutically acceptable salt or solvate thereof is administered at about 1.5 mg/kg, 2 mg/kg, and 5 mg/kg per unit dosage. For example, Decitabine or a pharmaceutically acceptable salt or solvate thereof is administered at about 1 mg/kg and 2 mg/kg per unit dosage.

In a preferred embodiment, said MDM2 inhibitor (such as compound 2) and one or more of said anti-cancer agents are administered simultaneously, concurrently or in combination.

In a more preferred embodiment, the time interval between the administrations of said MDM2 inhibitor and said anti-cancer agent successively can be about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In a preferred embodiment, a pharmaceutical composition comprising said MDM2 inhibitor (such as compound 2) and one or more of said anti-cancer agents (such as Azacitidine, Decitabine, and Cytarabine) is administered as a whole dosage unit, and the times of administration at each day include, but are not limited to: once, twice, 3 times, 4 times, 5 times or 6 times.

In a preferred embodiment, said MDM2 inhibitor (such as compound 2) and one or more of said anti-cancer agents (such as Azacitidine, Decitabine, and Cytarabine) are administered as a separated dosage unit respectively, and the times of administration at each day include, but are not limited to: once, twice, 3 times, 4 times, 5 times or 6 times.

In a preferred embodiment, said MDM2 inhibitor (such as compound 2) and one or more of said anti-cancer agents (such as Azacitidine, Decitabine, and Cytarabine) are administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days.

In a preferred embodiment, said MDM2 inhibitor (such as compound 2) and one or more of said anti-cancer agents (such as Azacitidine, Decitabine, and Cytarabine) are administered continuously for one or more courses of treatment, comprising 1, 2, 3, 4, 5, 6, 7, 8, 9 or 10 courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and the interval between every two courses of treatment is 0, 1, 2, 3, 4, 5, 6, 7, 8, 9, 10 days, two weeks, three weeks or four weeks.

In a preferred embodiment, said MDM2 inhibitor (such as compound 2) and one or more of said anti-cancer agents (such as Azacitidine, Decitabine, and Cytarabine) are administered by an identical route (such as orally) or different routes (such as orally and parenterally (such as by injection) respectively), comprising orally, buccally, inhalation of spray, sublingually, rectally, transdermally, via vaginal mucosa, transmucosally, by topical administration, by nasal or intestinal administration, by injection administration, such as intramuscular injection, subcutaneous injection, intramedullary injection, and intrathecally, by direct brain administration, by in situ administration, by subcutaneous, intraperitoneal, intravenous injection, intraarticular synovium, intrasternal, intrahepatic, intralesional, intracranial, abdominal cavity, nasal cavity, or intraocular injection or other drug delivery routes.

In addition, the present invention relates to a method for treating adult relapsed or refractory acute myeloid leukemia and relapsed or refractory high risk/extremely high risk myelodysplastic syndrome, comprising administering compound 2 alone and in combination with Azacitidine or Cytarabine.

In a preferred embodiment, the administration method is:
the dosage of compound 2 is escalated following the standard 3+3 regimen, wherein the initial dosage is 150 mg, and is escalated orderly to 200 mg, 250 mg, and 300 mg, is taken orally once a day, is brought into use at the first day in each cycle, is continuously taken for 7 days, then is discontinued for 21 days, and every 28 days is an administration cycle;

when the first stage of dose escalation of compound 2 alone is completed, a second stage, i.e. the combination administration with dose escalation of compound 2, can be entered; in the combination administration regimen, the dosage of compound 2 is started at 100 mg, and is escalated orderly to 150 mg and 200 mg; Azacitidine is at a fixed dosage, 75 mg/m$^2$, via subcutaneous injection, once a day, is brought into use at the first day in each cycle, is continuously taken for 7 days, then is discontinued for 21 days, and every 28 days is an administration cycle; and Cytarabine is at a fixed dosage, 1 g/m$^2$, via subcutaneous injection, with the intravenous infusion time period of not less than 4 hours, once a day, is brought into use at the third day in each cycle, is continuously taken for 5 days, then is discontinued for 21 days, and every 28 days is an administration cycle.

In a preferred embodiment, Azacitidine or Cytarabine is administered 4 hours after the oral administration of compound 2; and after the combined treatment of two drugs, a rest period is entered.

Another, the present invention relates to use of compound 2 in the preparation of a drug for treating myelodysplastic syndrome (MDS).

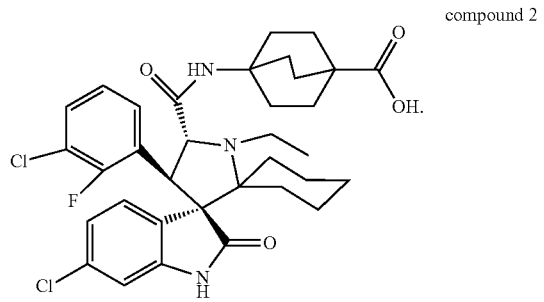 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

compound 2

Or, the present invention relates to use of compound 2 alone and in combination with Dabrafenib and Trametinib in the preparation of a drug for treating melanoma. Preferably, The weight ratio of compound 2 and combination of Dabrafenib and Trametinib is 50:30:1.

Or, the present invention relates to use of compound 2 alone and in combination with Fulvestrant and Alpelisib in the preparation of a drug for treating breast cancer. Preferably, The weight ratio of compound 2 and combination of Fulvestrant and Alpelisib is 50:20:25.

EMBODIMENTS

In order to make the objects and technical solutions of the present invention clearer, the present invention is further illustrated in conjunction with particular embodiments below. It should be understood that these embodiments are only used to describe the present invention but not to limit the scope of the present invention. Furthermore, all the specific experimental methods which are not mentioned in the following embodiments are carried out according to the conventional methods.

Data Analysis

The tumor growth curve is depicted, wherein X axis shows the observation time, and Y axis shows the corresponding tumor volume (geometric mean). The comparison among three or more groups uses one-way ANOVA. If the F value has a significant difference, multiple comparisons should be carried out after the ANOVA analysis. All data analysis uses SPSS 18.0. Prism (the sixth version) is used for graphing. Attune N×T flow cytometer (Thermo Fisher Scientific Inc.) is used for analyzing tumor infiltrating lymphocytes. Data acquisition and analysis use Analyst Software 1.6.3 work station (AB sciex, Ontario, Canada). For MOLM-13 systemic model, the death date of the last mouse is used for analyzing the median total survival and generating the Kaplan-Meier curve. Logarithmic rank test and Bonferroni multiple test are used for comparing the survival curves of different treatment groups.

CellTiter-Glo® (CTG) Cell Proliferation Experiment

The anti-proliferative effect is detected by the CellTiter-Glo® (CTG) experiment. Cells are inoculated into a 96-well plate, and are treated with different concentrations of test substances for 24-72 hours. Generally, 9 series of doses of test substance are selected, and are added into the 96-well plate at 5 µl/well. For the combined experiment, the final volume of 2 test substances is 5 µl/well. Each test dose is subjected to 3 repeated wells. 100 µl diluent is added to 3-6 selected wells on the same culture plate as the control group, and another 3-6 wells are set as the blank control. In addition to the blank control, 95 µl cell suspension (containing a suitable cell number for ensuring that the cells of the cell control group are just confluent on the bottom of the well when it needs to be tested) is added into each well of the same 96-well plate. The culture plate is cultured in a $CO_2$ incubator at 37° C. for 24-72 hours. When the culture is completed, the 96-well plate and CellTiter-Glo reagent are equilibrated for 30 minutes under room temperature, and then 100 µL CellTiter-Glo reagent is added into each well. The culture plate is mixed homogeneously on a shaker for 2 minutes, then is left to stand under room temperature for 10 minutes, after which the fluorescence value is read using a Biotek synergy HIMF microplate reader. The average fluorescence value of the 3 repeated wells is used, and the cell survival rate percentage is calculated by following formula:

Cell survival rate (%)=(the fluorescence value of test wells−the fluorescence value of the negative control wells)/(the fluorescence value of the solvent control group−the fluorescence value of the negative control group)×100%

The nonlinear regression data analysis method of Graphpad Prism 6.0 software (Golden software, Golden, ColOrado, USA) is used for calculating $IC_{50}$.

For the combined experiment, the average fluorescence value of the 3 repeated wells of the single drug control is normalized for calculating cell survival rate. The IC50s of the combined curve and single drug curve are compared to determine the synergistic effect of the 2 compounds by observing whether the curve of the combined drug group is moved left. For the combined administration experiment at cell level, the combination index (CI) is calculated using a CalcuSyn program, and the result is further analyzed (Chou, T. C. (2010). Drug combination studies and their synergy quantification using the Chou-Talalay method. Cancer research 70, 440-446). The CI value of the two-drug combination <0.9 indicates the two-drug combination has a synergistic effect; the CI value=0.9 indicates the two-drug combination has an additive effect; and the CI value>0.9 indicates the two-drug combination has an antagonistic effect.

Evaluation Method for In Vivo Efficacy Experiment

After the animals are inoculated with tumor cells, the health and death situation of the animals are monitored each day, the routine check comprises observing the tumor growth and the effects of drug treatment on the daily behaviors of the animals, such as action and activity, the amount of food and water intakes, the body weight change (the body weight is measured twice each week), the appearance and signs or other abnormal circumstances. The animal death count and side effects in the groups are recorded based on the number of animals in each group. All processes comprising administration, and measurement of tumor and body weight are performed in a laminar flow cabinet.

The subcutaneous xenograft tumor model of human tumor immuno-deficient mice is established by the cell inoculation method (reference can be made to Gould S E et al., Translational value of mouse models in oncology drug development, Nature medicine, 2015 21, 431-439, and Souers A J et al., ABT-199, a potent and selective BCL-2 inhibitor, achieves antitumor activity while sparing platelets, Nature medicine, 2012 19.202-208): tumor cells at logarithmic phase are collected, then are resuspended in 1×PBS after being counted, the concentration of the cell suspension is adjusted to $2.5-5 \times 10^7$/mL. Tumor cells are subcutaneously inoculated to right-side back of the immuno-deficient mice using a 1 mL syringe (4th needle) at $5-10 \times 10^6$/0.2 mL/mouse (experimental animals are purchased from Beijing Vital River Laboratory Animal Technology Co., Ltd. SCXK (Beijing) 2016-0006). All the experimental operations of animals strictly abide by the usage and management standard of experimental animals of GenePharma Co., Ltd. and Suzhou Yasheng Pharmaceutical Co., Ltd. The calculations of related parameters make reference to "Technical guidelines for non-clinical research of cytotoxic anti-tumor drugs" of China CFDA.

Systemic and subcutaneous AML xenograft models are generated in female NOD SCID mice. All animal experiments are performed in the animal facility of GenePharma (Suzhou, China).

For systemic AML model, six- to eight-week-old female NOD SCID mice are pretreated with cyclophosphamide (150 mg/kg, intraperitoneally) continuously for two days. Then the MOLM-13 systemic AML xenograft model is established by inoculating $1 \times 10^7$ cells into the caudal vein intravenously.

For subcutaneous model, OCI-AML-3 cells ($1 \times 10^6$) are injected subcutaneously into the right side of the abdomen of 6- to 8-week-old mice. About 10 days after the cell inoculation, the mice are randomly divided into groups based on the primary tumor size achieving about 100-150 mm³ of average tumor volume.

The body weight and the tumor size of the animals are determined twice each week during the experiments. The animal status and the conditions such as whether death exists etc. are observed each day. Routine monitoring comprises the tumor growth and the effects of treatment on normal animal behaviors, of which the specific content includes the activity, food and water intakes, the increase or decrease of body weight, eyes, hair and other abnormal conditions of experimental animals. All the death and clinical symptoms observed during the experiment are recorded in the original data. All the whole operations of administration and the measurement of mouse weight and tumor volume are performed in a laminar flow cabinet. According to the requirements of experimental protocols, after the last administration, plasma and tumor tissues are collected, the body weight is weighed, a photograph is taken, and data is recorded. The plasma and tumor samples are cryopreserved at −80° C. for further use.

The tumor diameter is measured twice using a vernier caliper each week. The computational formula of the tumor volume (TV) is: $TV=a \times b^2/2$. In the computational formula, a and b represent the length and width of the tumor measurement respectively. The computational formula of the relative tumor volume (RTV) is: $RTV=V_t/N_1$. In the computational formula, $V_1$ is the tumor volume when being grouped and administered, and $V_t$ is the tumor volume when being measured at a certain day after the administration.

The evaluation index of the anti-tumor activity is the relative tumor proliferation rate T/C (%), and the computational formulae respectively are: the relative tumor proliferation rate T/C (%)=$(T_{RTV}/C_{RTV}) \times 100\%$, $T_{RTV}$ is the RTV of the treatment groups, and $C_{RTV}$ is the RTV of the vehicle control groups. The tumor remission rate (%) is derived by dividing the number of SD (Stable Disease), PR (Partial response) and CR (Complete response) appearing in the tumor bearing mice after treatment by the total number of mice in the group×100%.

Change of body weight of animals, %=(Measured body weight−body weight when being grouped)/body weight when being grouped×100%.

Efficacy evaluation criteria: According to "Technical guidelines for non-clinical research of cytotoxic anti-tumor drugs" of China CFDA (November, 2006), T/C (%) value≤40%, and p<0.05 by statistical analysis is effective. If the body weight loss of mice is more than 20% or the drug-related death count is more than 20%, it is considered that the drug dosage has a severe toxicity, and is represented as an excessive toxic dosage. T/C percentage is the indicator of the anti-tumor efficacy: NCI considers that T/C values<42% have a significant anti-tumor activity. T/C values<10% are considered as having a highly significant anti-tumor activity, and if they meet the toxic and some other requirements (known as DN-2 level of activity), then NCI uses them as the rationality demonstration of the clinic trials.

The synergistic analysis uses the following formula (reference can be made to Gould S E et al., Translational value of mouse models in oncology drug development, Nature medicine, 2015 21, 431-439): synergistic factor=((A/C)×(B/C))/(AB/C); A=RTV value of the A drug alone group; B=RTV value of the B drug alone group; C=RTV value of the vehicle control group, AB=RTV value of the AB combined group (Clarke R., Issues in experimental design and endpoint analysis in the study of experimental cytotoxic agents in vivo in breast cancer and other models[J], Breast Cancer Research & Treatment, 1997, 46 (2-3):255-278). If the synergistic factor>1, then they have a synergistic effect; if the synergistic factor=1, then they have an additive effect; and if the synergistic factor<1, then they have an antagonistic effect.

Embodiment 1. Preparation of Compound 2

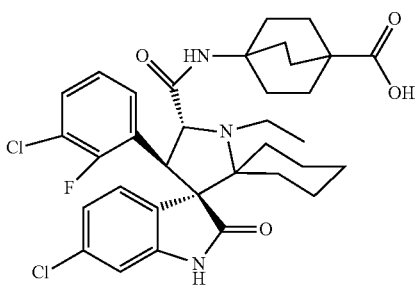

compound 2

The MDM2 inhibitor, compound 2, is prepared according to the one-step method or multi-step method disclosed in U.S. Pat. No. 9,745,314, WO 2015/161032, and in Aguilar et al., J. Med. Chem., 2017(60)2819-2839.

Embodiment 2. Anti-Proliferative Effect of Compound 2 Alone or in Combination on Human-Derived AML Carcinoma Cell Line

Figure 1:
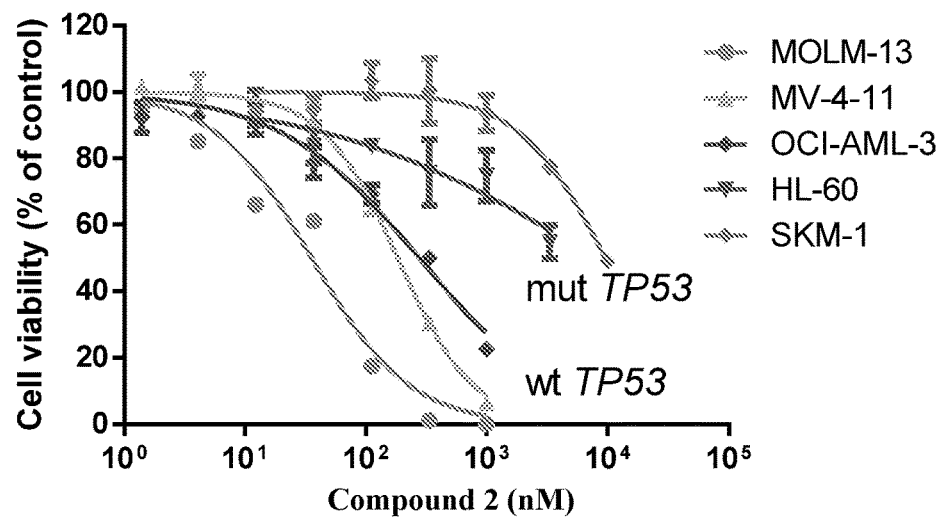
FIG. 1. Figure of the proliferation inhibition effect of compound 2 alone in vitro on TP53 wild type and mutant type AML cell line.

2.1. Anti-Proliferative Effect of Compound 2 Alone on Human-Derived AML Carcinoma Cell Line Reference is made to above "CellTiter-Glo® (CTG) cell proliferation experiment". In the CTG experiment, the in vitro proliferation inhibition effect of compound 2 alone on three TP53 wild types of AML (acute myeloid leukemia) cells MOLM-13, MV-4-11 and OCI-AML-3, and two TP53 mutant types of AML cell lines HL-60 and SKM-1. In the experiment, both MOLM-13 and MV-4-11 cell lines are TP53 wild type and FLT3-ITD mutant type of AML cell lines, and OCI-AML-3 cell line is TP53 wild type AML cell line without FLT3-ITD mutation. MV-4-11 cell line is from ATCC® CRL-9591™, biphenotypic B myelomonocytic leukemia, HL-60 cell line is from ATCC® CCL-240™, acute promyelocytic leukemia, and MOLM-13 cell line is from Bena Culture collection resource number: BNCC340568, human acute myeloid leukemia cells. OCI-AML-3 cell line is purchased from Cobioer (Nanjing, China). SKM-1 is purchased from Japanese Collection of Research Bioresources Cell Bank (JCRB). Acute myeloid leukemia cell line is cultured in RPMI 1640 medium (Gibco, Cat #C11875500BT) containing 10% fetal calf serum (AUS-GENEX, Cat #FBSSA500-S), except for MV-4-11, which is cultured in IMDM medium (Gibco, Cat #C12440500BT). All the cell lines are subjected to genetic identification and free of microbial contamination. Unless otherwise specified, in the CTG experiment, cells are treated with a drug for 72 hours. As shown in FIG. 1, in order to study the in vitro proliferation inhibition effect of compound 2 alone on TP53 wild type and mutant type AML cell lines, MOLM-13, MV-4-11, OCI-AML-3, HL-60 and SKM-1 cells are treated with increasing doses of compound 2 alone. After 72 hours, the cell survival is measured by the CTG method, and the growth inhibition curve is depicted using GraphPad Prism 6. The cell survival percentage is represented as Mean±SEM, and n=2 or 3.

The results of studies indicate that in the above-mentioned five tested AML cell lines, TP53 wild type cell lines are sensitive to the drug effect of compound 2, and TP53 mutant type cell lines are not sensitive to the effect of compound 2.

Specifically, as shown in table 1, the IC50 values of compound 2 in TP53 wild type MOML-13, MV-4-11 and OCI-AML-3 cell lines are 26.8±4.9 nM, 165.9±42.4 nM and 315.6±97 nM respectively. In the cell lines, the cell lines which are most sensitive to compound 2 alone are TP53 wild type and FLT3-ITD mutant type of AML cell lines MOLM-13 and MV-4-11. Secondly, the cell lines which are relatively sensitive to compound 2 alone are TP53 wild type OCI-AML-3 cell line without FLT3-ITD mutation. In comparison, the anti-proliferative effect of compound 2 in TP53 mutant type cell lines is weak, and the IC50 values in HL-60 and SKM-1 cell lines are 2558.3±581.5 nM and 8947.3±569.6 nM respectively.

TABLE 1

IC50 values of compound 2 in AML cell lines carrying different genetic mutations (nM)

| Cell lines | TP53 | FLT3 | NPM1 | RAS | $IC_{50}$ values, nM (Mean ± SD, n = 2 or 3) Compound 2 |
|---|---|---|---|---|---|
| MOLM-13 | Wt | ITD | wt | wt | 26.8 ± 4.9 |
| MV-4-11 | Wt | ITD | wt | wt | 165.9 ± 42.4 |
| OCI-AML-3 | Wt | Wt | mut | mut | 315.6 ± 97 |
| HL-60 | Del | Wt | wt | wt | 2558.3 ± 581.5 |
| SKM-1 | mut | Wt | wt | wt | 8947.3 ± 569.6 |

Note:
wt, wild-type;
mut, mutant;
Del, deletion

Figure 2A:
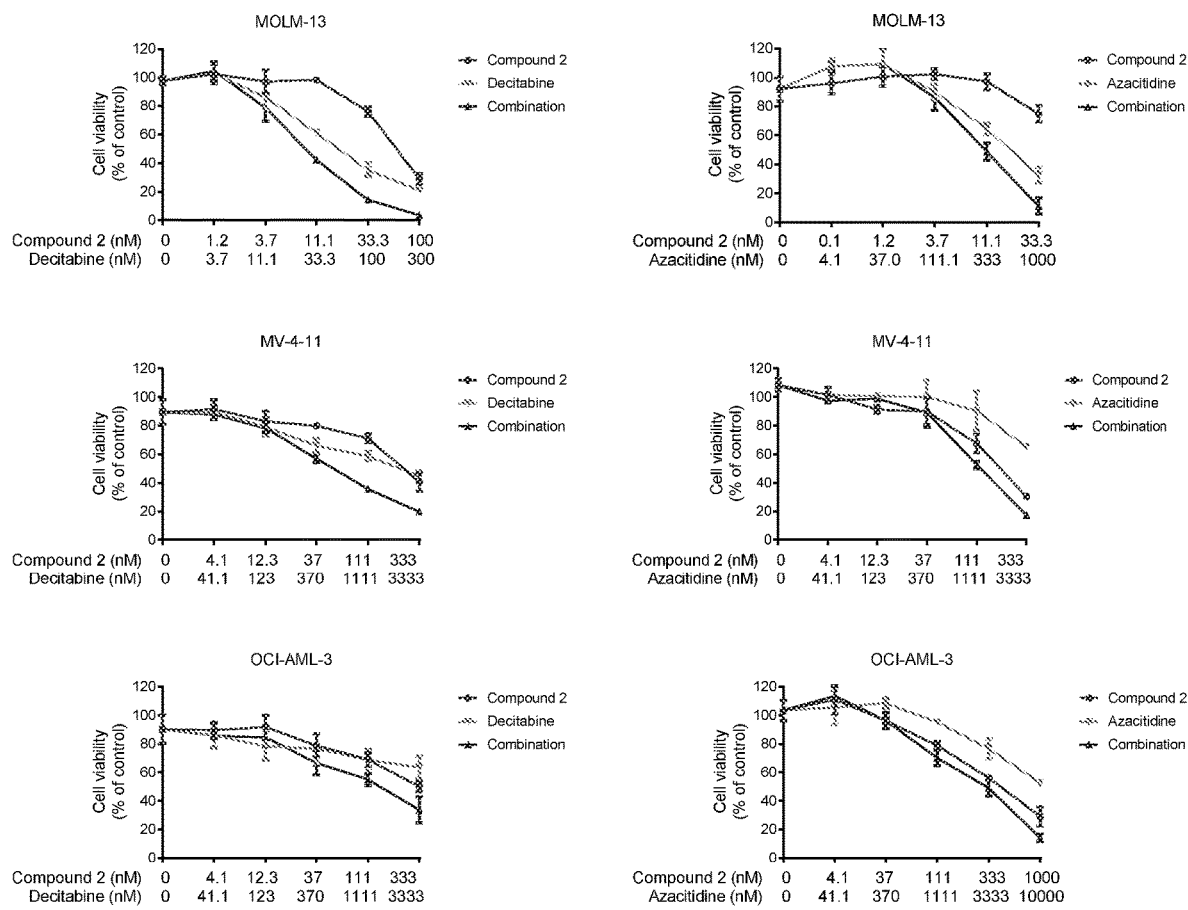
FIG. 2A. Figure of the growth inhibition effect of compound 2 in combination with Decitabine or Azacitidine on TP53 wild type AML cell line.
Figure 2B:
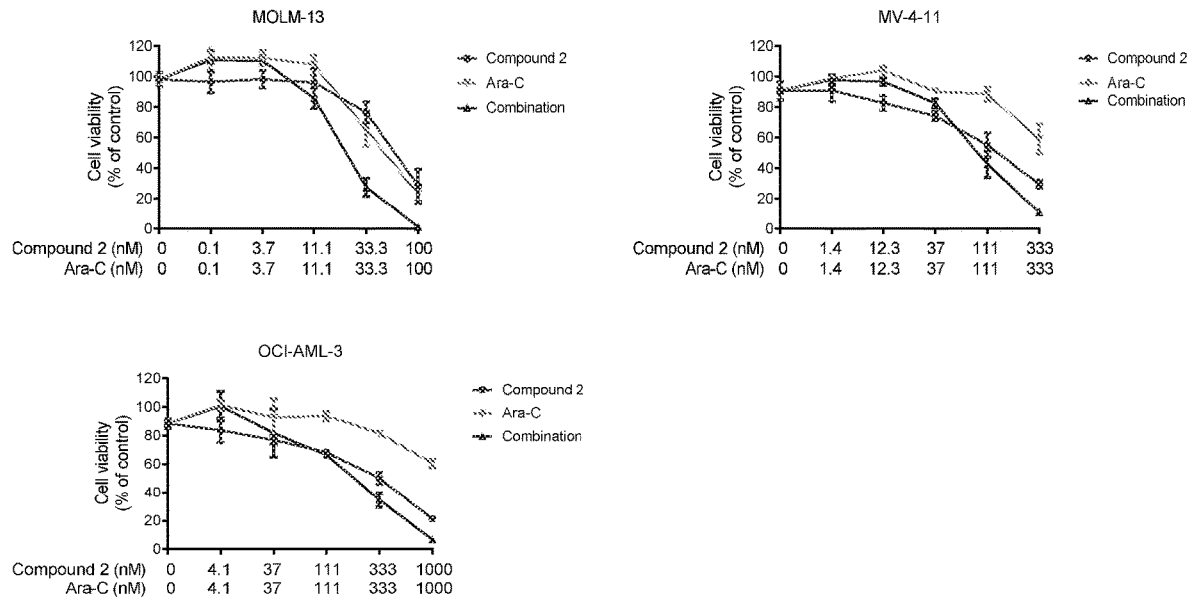
FIG. 2B. Figure of the growth inhibition effect of compound 2 in combination with Cytarabine on TP53 wild type AML cell line.

2.2. Anti-Proliferative Effect of Compound 2 in Combination on Human-Derived AML Carcinoma Cell Line The growth inhibition effects of compound 2 in combination with Decitabine, Azacitidine, or Cytarabine (Ara-C) on TP53 wild type AML cell line are shown in FIGS. 2A and 2B. AML cells are treated with a gradient concentration of compound 2, Decitabine, Azacitidine, and Cytarabine alone or in combination for 3 days, and the cell growth inhibiting activity is detected by CellTiter-Glo luminescence method. The cell survival percentage is represented as Mean±SEM, n=3.

The results show that when compound 2 is administered in combination with demethylation drugs comprising Decitabine (Dec), Azacitidine (Aza) and Cytarabine (Ara-C), the above-mentioned combined administrations are all found to have an enhanced anti-proliferative effect.

It can be seen from FIG. 2A that the specific CI value and the original dosage-effect growth inhibition curve of compound 2 in combination with demethylation drugs Decitabine and Azacitidine. It can be seen from FIG. 2B that the specific CI value and the original dosage-effect growth inhibition curve of compound 2 in combination with Cytarabine. The combination administration response curve of compound 2 in combination with Decitabine is moved left, and the combination index (CI) is less than 0.9, which shows that the two-drug combination of Decitabine has a synergistic effect.

It can be seen that in the in vitro experiment, compound 2 not only has a significant anti-proliferative effect on AML cells in TP53 wild type AML cell lines, especially in TP53 wild type and FLT3-ITD mutant type of AML cell lines when being used alone, but also is outstanding that compound 2 in combination with other therapeutic drugs comprising demethylation drugs (Decitabine and Azacitidine), and traditional chemotherapeutic drug Cytarabine, exhibiting as after the combined administration, the IC50 value is reduced, and be compared by the IC50s of the combined administration curve and single drug curve, it is observed that the combined administration group curve is moved left. Therefore, when compound 2 is used in combination with other therapeutic drugs comprising demethylation drugs (Decitabine and Azacitidine), and traditional chemotherapeutic drug Cytarabine, it has a synergistic effect, and its anti-proliferative effect is enhanced significantly.

Embodiment 3. Anti-Proliferation Activity of Compound 2 Single Agent or in Combination with Other Therapeutic Drugs in Non-Small Cell Lung Cancer (NSCLC) Cell Lines

3.1 Anti-Proliferative Activity of Compound 2 Single Agent in KRAS and STK11 Co-Mutated Non-Small Cell Lung Cancer (NSCLC) Cell Lines A549, NCI-H460, and NCI-H2122

Refer to the aforementioned "CellTiter-Glo® (CTG) Cell Proliferation Experiment". In the CTG experiment, the antiproliferative activity of compound 2 as a single agent was tested in three non-small cell lung cancer (NSCLC) cells A549, NCI-H460, and NCI-H2122 with co-mutations of STK11 and KRAS. Among them, A549 cell line, NCI-H460 cell line, and NCI-H2122 cell line were all purchased from Nanjing Cobioer Biosciences Co., Ltd. All cell lines have been genetically authenticated and are free of microbial contamination. Unless otherwise specified, the cells are treated with drugs for 72 hours in CTG experiments.

Figure 3A:
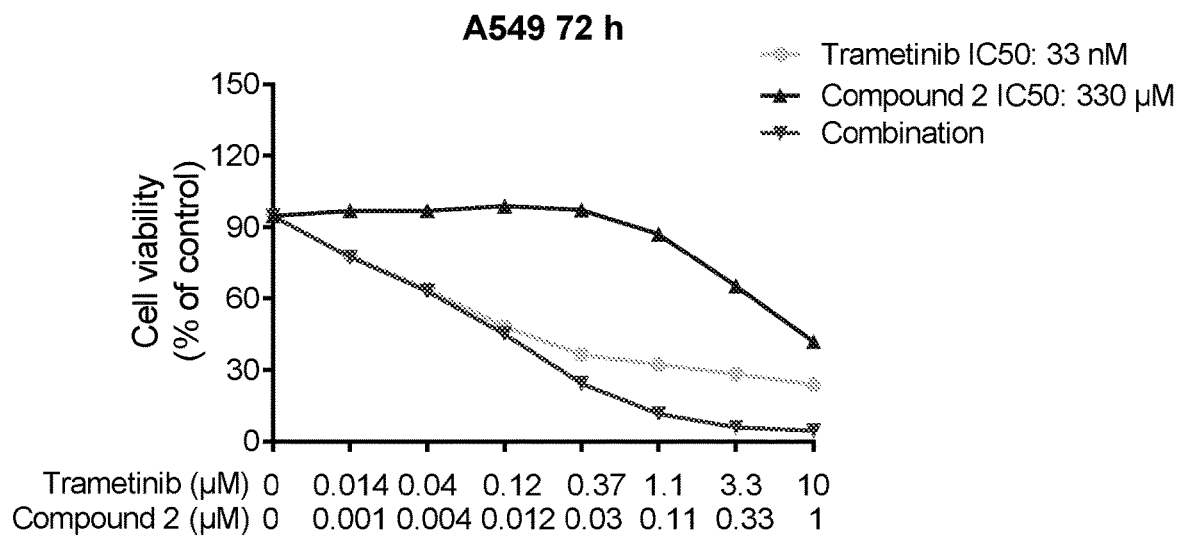
FIG. 3A-3C. Figure of the antiproliferative effect of compound 2 in combination with trametinib on STK11 and KRAS co-mutated non-small cell lung cancer (NSCLC) cell line.
Figure 3B:
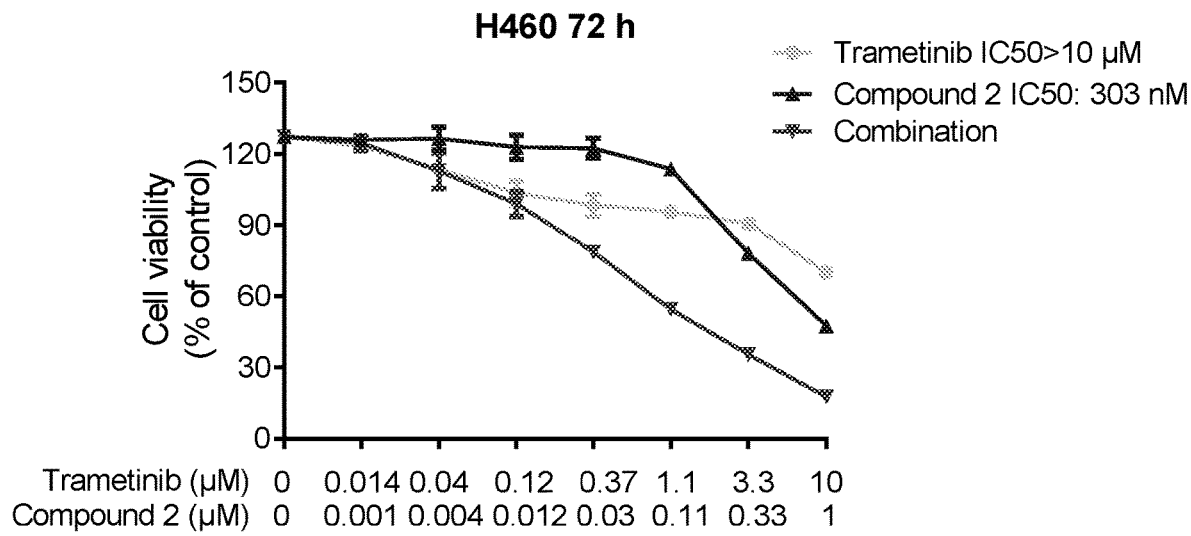
Figure 3C:
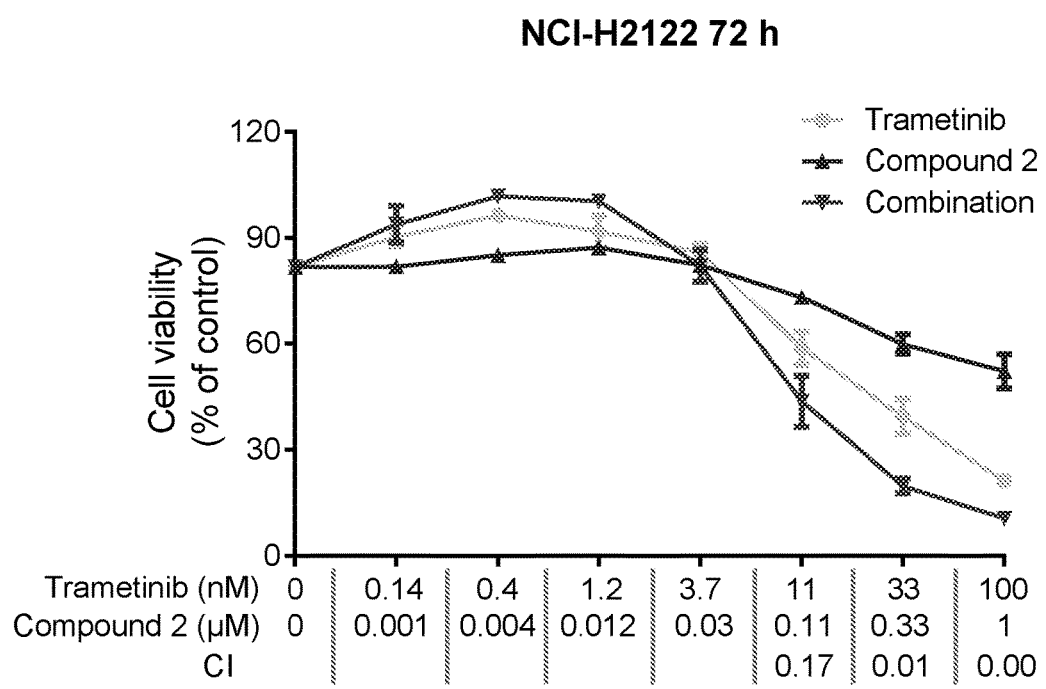

As shown in FIG. 3A-3C, the IC50 values of compound 2 in non-small cell lung cancer (NSCLC) A549, NCI-H460, and NCI-H2122 cell lines are 33 nM, 330 µM and 79 nM, respectively.

3.2 Anti-Proliferative Activity of Combination Treatment with Compound 2 and Trametinib in STK11 and KRAS Co-Mutated Non-Small Cell Lung Cancer (NSCLC) Cell Lines A549, NCI-H460, and NCI-H2122

Refer to the aforementioned "CellTiter-Glo® (CTG) Cell Proliferation Experiment". In the CTG experiment, the antiproliferative activity of the combination of compound 2 and trametinib was tested in three STK11 and KRAS co-mutated non-small cell lung cancer (NSCLC) cells A549, NCI-H460, and NCI-H2122. Unless otherwise specified, the cells are treated with drugs for 72 hours in CTG experiments.

As shown in FIG. 3A-3D, the combination of compound 2 and trametinib inhibited the growth of non-small cell lung cancer (NSCLC) cell lines A549, NCI-H460, and NCI-H2122 with co-mutations of STK11 and KRAS. The above three cell lines were treated with gradient concentrations of compound 2, trametinib alone or in combination for 3 days, and the cell growth inhibitory activity was detected by the CellTiter-Glo luminescence method. The percentage of cell survival is expressed by Mean±SEM, n=3.

The results showed that when compound 2 was used in combination with trametinib, the anti-proliferative activity was enhanced.

The specific CI values and the original dose-effect growth inhibition curves of compound 2 and trametinib were shown in FIGS. 3A, 3B, and 3C. The combined drug response curves of compound 2 in combined with trametinib shifted to the left, and the combination index (CI value) were less than 0.9, indicating that there were synergistic effects when compound 2 was used in combined with trametinib.

In summary, compound 2 single agent has potent anti-proliferative activity in non-small cell lung cancer (NSCLC) cell lines A549, NCI-H460, and NCI-H2122 with STK11 and KRAS co-mutations. Importantly, the combination of compound 2 and trametinib showed synergistic antiproliferative activity.

3.3 Anti-Proliferative Activity of Compound 2 and Trametinib in KRAS Wild-Type and STK11 Wild-Type Non-Small Cell Lung Cancer (NSCLC) Cell Lines NCI-H226 and NCI-H292

Refer to the aforementioned "CellTiter-Glo® (CTG) Cell Proliferation Experiment". In the CTG experiment, the antiproliferative activity of the combination of compound 2 and trametinib was tested in KRAS wild-type and STK11 wild-type non-small cell lung cancer (NSCLC) cell lines NCI-H226 and NCI-H292.

Among them, the NCI-H226 cell line was purchased from Nanjing Cobioer Biosciences Co., Ltd., and the NCI-H292 cell line was purchased from the Institute of Biochemistry and Cell Biology, Chinese Academy of Sciences. All cell lines have been genetically authenticated and are free of microbial contamination. Unless otherwise specified, the cells are treated with drugs for 72 hours in CTG experiments.

Figure 4A:
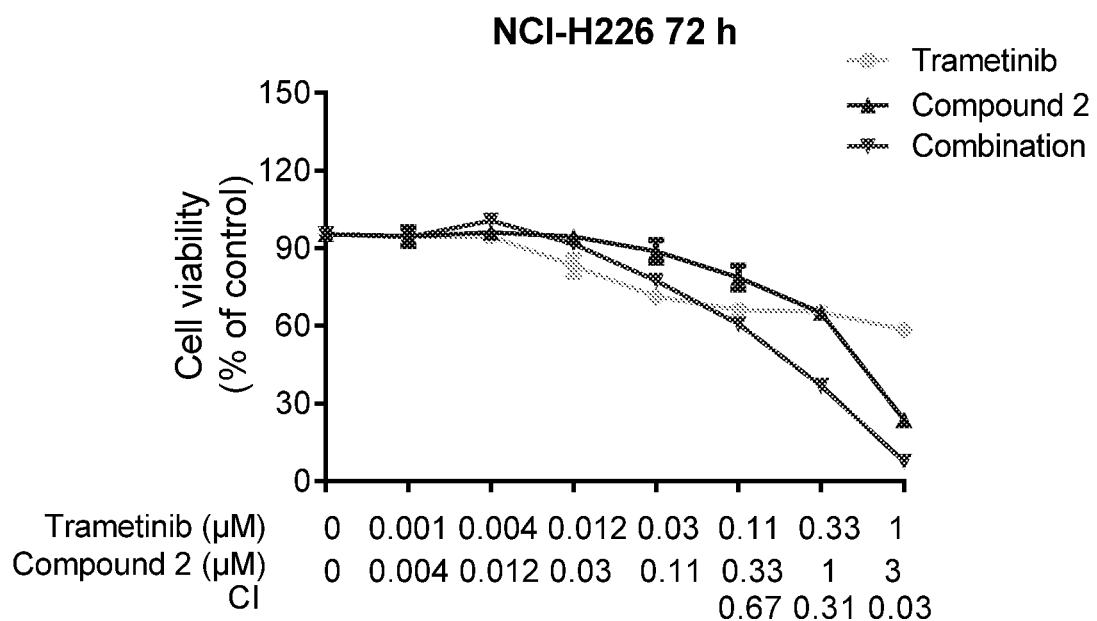
FIG. 4A-4B. Figure of the antiproliferative effect of compound 2 in combination with trametinib on KRAS wild-type and STK11 wild-type non-small cell lung cancer (NSCLC) cell line NCI-H226 and NCI-H292.
Figure 4B:
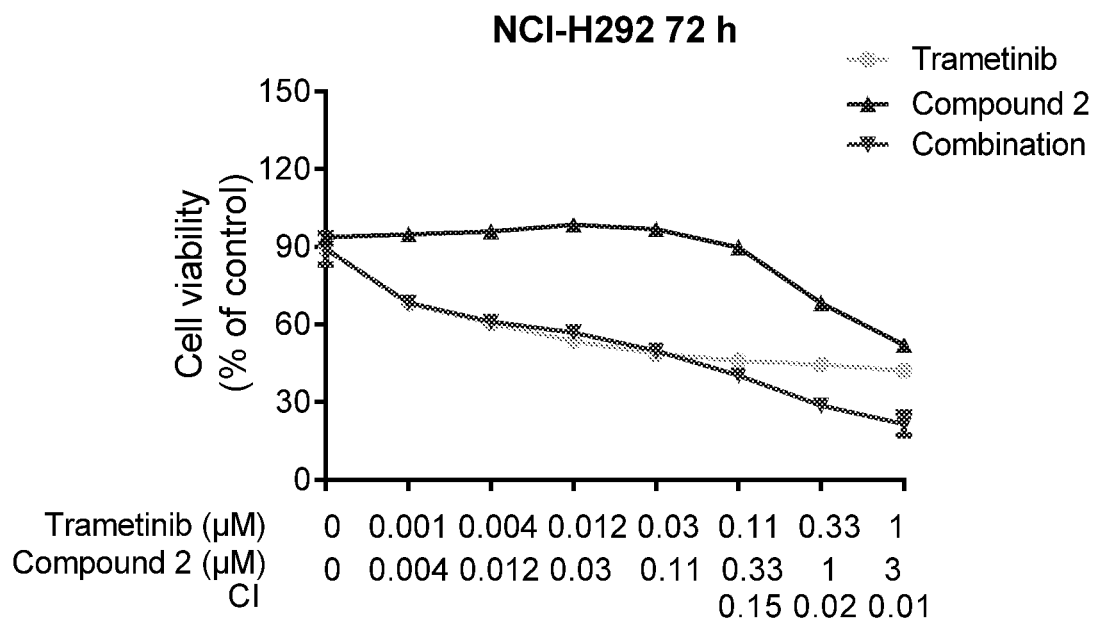

As shown in FIGS. 4A-4B, the combination of compound 2 and trametinib inhibited the growth of KRAS wild-type and STK11 wild-type non-small cell lung cancer (NSCLC) cell lines NCI-H226 and NCI-H292. The above two cell lines were treated with gradient concentrations of compound 2, trametinib alone or in combination for 3 days, and the cell growth inhibitory activity was detected by the CellTiter-Glo luminescence method. The percentage of cell survival is expressed by Mean±SEM, n=3.

The results showed that when compound 2 was used in combination with trametinib, anti-proliferative activity was enhanced.

The specific CI value and the original dose-effect growth inhibition curves of compound 2 and Trametinib were shown in FIGS. 4A and 4B. When cells were treated with the combination of trametinib and compound 2 with a molar concentration ratio of approximately 1:3 (especially when the molar concentration ratio of the two is 0.33 µM:1 µM to 1 µM:3 µM), the response curves shifted to the left, and the combination index (CI Value) were less than 0.9, indicating that there were synergistic effects when compound 2 was used in combined with trametinib.

In summary, compound 2 single agent has potent anti-proliferative activity in KRAS wild-type and STK11 wild-type non-small cell lung cancer (NSCLC) cell lines NCI-H226 and NCI-H292. Importantly, the combination of compound 2 and trametinib showed synergistic antiproliferative activity.

Embodiment 4. Administration of Compound 2 Alone or in Combination In Vitro Induces Apoptosis and Cycle Arrest of Cancer Cells

4.1. Compound 2 Alone Induces MOLM-13 AML Apoptosis

The activation of P53 signaling pathway can induce apoptosis, cycle arrest, or senility of cells. In all tested AML cell lines, the MOLM-13 cell lines carrying wild type TP53 and FLT3-ITD mutation exhibits a higher sensibility to the drug effect of compound 2 than that of OCI-AML-3 and MV-4-11. Therefore, Annexin V-PI fluorescence probe and flow cytometer are used for analyzing the apoptosis of MOML-13 cells after being treated with compound 2 alone or in combination with Decitabine, Azacitidine or Cytarabine (Ara-C).

Figure 5A:
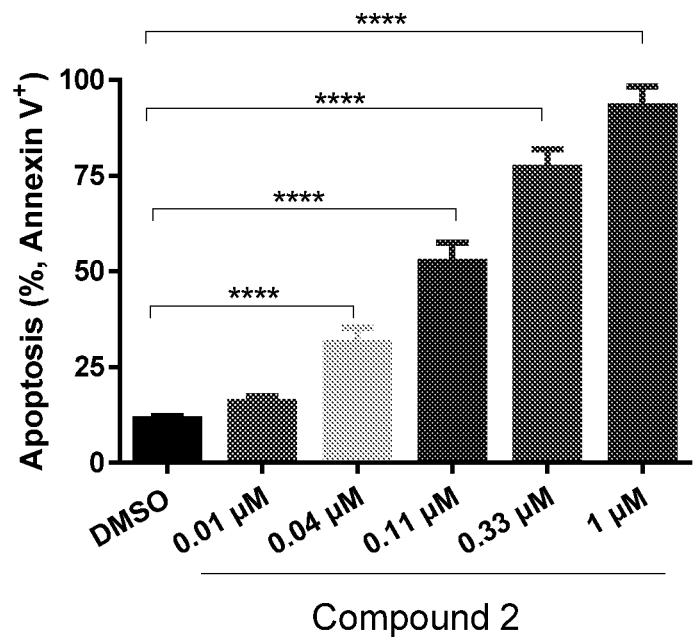
FIG. 5A. Schematic diagram of MOLM-13 cell apoptosis after being treated with compound 2 alone at different concentrations.
Figure 5B:
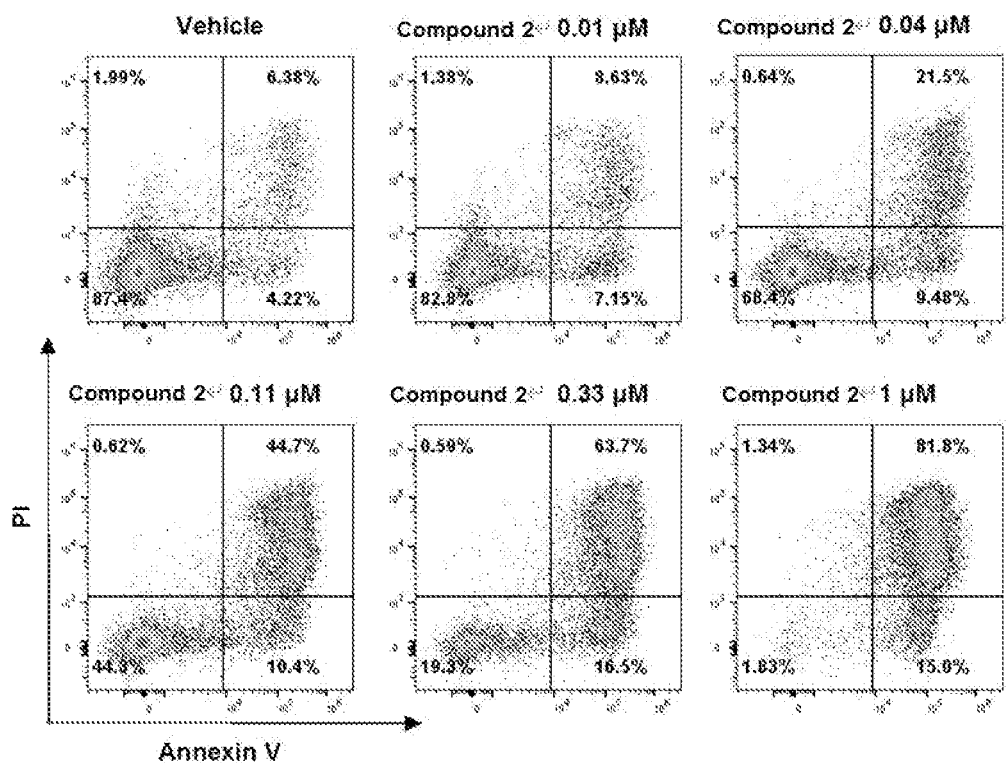
FIG. 5B. is the representative drawing of flow analysis of compound 2 induced apoptosis in FIG. 5A.

As shown in FIGS. 5A and 5B, in FIG. 5A, MOLM-13 cells are treated in vitro with compound 2 at doses of 0.01 μM, 0.04 μM, 0.11 μM, 0.33 μM or 1 μM, 48 hours later, cells are collected and stained using Annenix V-FITC/PI, and the apoptosis is detected by a flow cytometer. The apoptosis percentage is represented as Mean±SEM, n=3. FIG. 5B is the representative drawing of flow analysis of compound 2 induced apoptosis in FIG. 5A. Being compared with the negative control group, P<0.0001.

The results show that compound 2 can significantly induce apoptosis (P<0.0001), and its effect is dose-dependent. Compound 2 alone induces the apoptosis of MOLM-13 cells in a dose-dependent way. For example, after being treated with 40 nM, 110 nM and 1000 nM of compound 2 for 48 hours, the MOLM-13 cells being apoptotic (Annexin V+ cells) is about 31.0%, 55.1% and 96.8% respectively. These data indicate that the growth inhibition effect of compound 2 on AML cells is related to the fact that it induces the programmed cell death of the cells.

4.2. Compound 2 in Combination with Decitabine, Azacitidine or Cytarabine Synergistically Induce MOLM-13 AML Apoptosis Studies report that all Decitabine, Azacitidine or Cytarabine can induce the apoptosis of AML cells (Hollenbach et al., 2010; Ossenkoppele and Lowenberg, 2015; Ram et al., 2017). The present invention further evaluates the effect of compound 2 in combination with demethylation drugs (such as Decitabine and Azacitidine) or Cytarabine on apoptosis in MOLM-13 cells.

Figure 6:
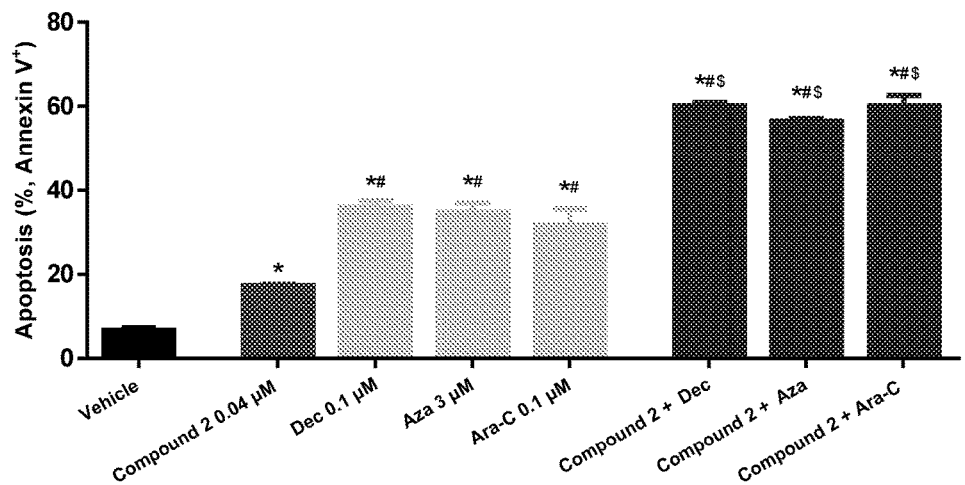
FIG. 6. Schematic diagram of cell apoptosis after treating MOLM-13 cells with compound 2 in combination with Decitabine, Azacitidine or Cytarabine.

MOLM-13 cells are treated with 0.04 μM compound 2 (the study of compound 2 alone in AML cells shows that the concentration is the minimum effective concentration) and suitable concentrations of Decitabine, Azacitidine or Cytarabine for 48 hours. As shown in FIG. 6, MOLM-13 cells are treated in vitro with 0.04 μM compound 2 in combination with 0.1 μM Decitabine (Dec), 3 μM Azacitidine (Aza) or 0.1 μM Cytarabine (Ara-C), 48 hours later, cells are collected and stained using Annenix V-FITC/PI, and the apoptosis is detected by a flow cytometer. Being compared with the blank group, P<0.05; being compared with the compound 2 alone group, P<0.05; being compared with chemotherapeutic drugs (Decitabine, Azacitidine or Cytarabine) alone group, P<0.05; Apoptotic cells (Annexin V+ cells) percentage is represented as Mean±SEM, n=3. The results show that being compared with control or single drug treatment, compound 2 in combination with Azacitidine, Decitabine or Cytarabine (Ara-C) can significantly increase the apoptosis ratio, and synergistically induce apoptosis.

4.3. Effect of Compound 2 Alone on AML Cell Cycle Progression

MOML-13, OCI-AML-3 and MV-4-11 cells (TP53 wild type AML cell lines) are treated with different concentrations of compound 2 for 48 hours, then the cells are stained using Propidium Iodide (PI), the percentage of cells at G0/G1, S and G2/M phases in total cells is determined by the analytical method of flow cytometry to study the effect of compound 2 on the cell cycle progression of AML cells.

Figure 7:
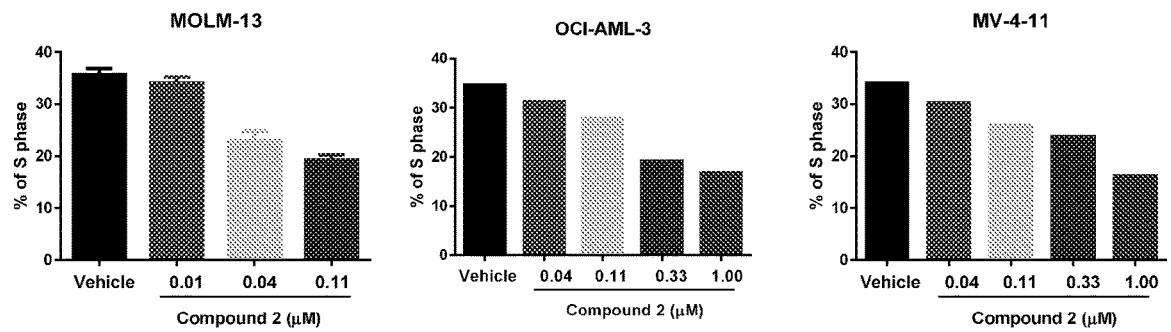
FIG. 7. Schematic diagram of compound 2 alone reducing the proportion of S phase cells in TP53 wild type AML cells in a dose-dependent manner.

As shown in FIG. 7, compound 2 alone reduces the proportion of S phase cells in TP53 wild type AML cells in a dose-dependent manner. MOLM-13 (A), OCI-AML-3 (B) and MV-4-11 (C) are treated in vitro with 0.01 μM, 0.04 μM, 0.11 μM, 0.33 μM or 1 μM of compound 2, 48 hours later, cells are collected and stained using PI, and the cell cycle arrest is detected by a flow cytometer. The result in the figure is the representative result, wherein in MOLM-13 cells, the result represents Mean±SEM, n=2; in OCI-AML-3 and MV-4-11 cells, the numerical value is the experimental result of a single well. In the three types of tested AML cell lines, the group treated with compound 2 is compared with the control group, compound 2 reduces the percentage of S phase cells in a dose-dependent manner.

The result shows that the growth inhibition effect of compound 2 on AML cells may be related to cell cycle arrest. Compound 2 alone can obviously reduce the percentage of S phase cells in MOML-13, OCI-AML-3 and MV-4-11 cell lines.

4.4. Effect of Administering Compound 2 in Combination with Decitabine, Azacitidine or Cytarabine on the Cell Cycle Progression of AML Cells MOML-13, OCI-AML-3 and MV-4-11 cells are treated with compound 2 (0.01 μM or 0.33 μM) in combination with suitable concentrations of Decitabine, Azacitidine or Cytarabine, 48 hours later, the cycle distribution of cells also is detected by a flow cytometer.

Figure 8:
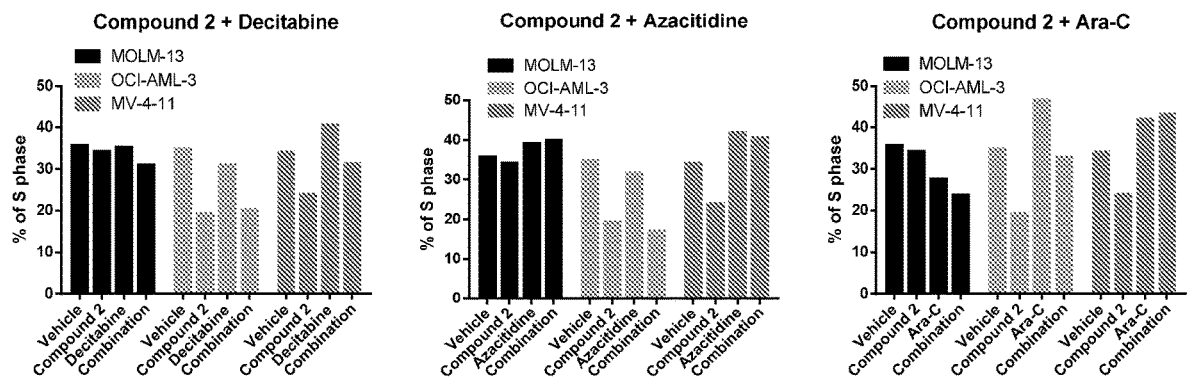
FIG. 8. Figure of the combinatorial effect of cycle arrest of MOLM-13, OCI-AML-3 and MV-4-11 cells which are treated with compound 2 in combination with Decitabine, Azacitidine and Cytarabine.

FIG. 8 shows that MOLM-13, OCI-AML-3 and MV-4-11 cells are treated with compound 2 in combination with Decitabine, Azacitidine, or Cytarabine (Ara-C), and the synergetic effect of cell cycle arrest is not found. MOLM-13 cells are treated with 0.01 μM compound 2 in combination with 0.05 μM Decitabine, 1 μM Azacitidine and 0.05 μM Cytarabine; OCI-AML-3 cells are treated with 0.33 μM compound 2 in combination with 1 μM Decitabine, 3 μM Azacitidine and 0.33 μM Cytarabine; MV-4-11 cells are treated with 0.33 μM compound 2 in combination with 0.33 μM Decitabine, 3 μM Azacitidine and 0.33 μM Cytarabine. After being treated with drugs for 48 hours, cells are collected and stained using PI. The samples are detected by a flow cytometer, then the data analysis is performed using the cell cycle program of FlowJo software. The result in the figure is the experimental result of a single well.

The results show that MOML-13, OCI-AML-3 and MV-4-11 cells are treated with compound 2 in combination with Decitabine, Azacitidine or Cytarabine, and the synergistically enhanced effect is not generated on cell cycle arrest. It indicates that the synergetic anti-proliferative activity of compound 2 in combination with Decitabine, Azacitidine or Cytarabine may not be related to cell cycle arrest.

Embodiment 5. In Vivo Drug Efficacy Evaluation

For systemic AML model, the six- to eight-week-old female NOD SCID mice are pretreated with cyclophosphamide (150 mg/kg, intraperitoneally) continuously for two days. Then the MOLM-13 systemic AML xenograft model is established by inoculating $1 \times 10^7$ cells into the caudal vein intravenously. Cells grow 3 days, then are randomly divided into groups for treatment of a single drug or drugs in combination using a carrier, compound 2 (50 mg/kg, is taken orally each day for 7 days), and Aza (1.5 mg/kg, intravenous injection each day for 7 days). In the treatment process and after the treatment is completed, the mice are monitored for the occurrence of hind leg paresis (HLP) or the abdominal swelling caused by disease progression, and a body weight loss >20%.

For subcutaneous model, OCI-AML-3 cells ($1\times10^6$) are injected subcutaneously into the right side of the abdomen of 6- to 8-week-old mice. About 10 days after the cell inoculation, the mice are randomly divided into groups based on the primary tumor size achieving about 100-150 mm³ of average tumor volume. Compound 2 is administered alone or in combination (50 mg/kg, is taken orally, every other day for 15 days) and Aza (2 mg/kg, intravenous injection each day for 7 days) or Dec (1 mg/kg, intravenous injection each day for 7 days). The tumor volume is measured twice using a vernier caliper each week and is represented by following formula in mm³: $V=0.5a\times b^2$; in the formula, a and b are the long diameter and short diameter of the tumor respectively. As the measure of potency, T/C (%) value is calculated according to the following formula: T/C (%)=($T_{RTV}/C_{RTV}$)×100%; wherein $T_{RTV}$ is the relative tumor volume (RTV) of the treatment groups, and $C_{RTV}$ is the RTV of the control group. RTV=$V_t/V_1$; wherein $V_1$ and $V_t$ are the average tumor volume on the first day (day 1) in the treatment, and the average tumor volume of a certain time point (day t) respectively. The tumor growth inhibition (TGI) is calculated according to the following formula: TGI (%)=100−T/C (%).

5.1. Anti-Tumor Effect of Compound 2 Alone in Mouse Xenograft Tumor Model of Human MOLM-13 AML Cells In the in vitro cell experiment, MOLM-13 is one of human AML cell lines which are sensitive to compound 2, and the IC50 value is 26.8±4.9 nM. A systemic MOLM-13 mouse xenograft model is established, and the anti-leukemia effect of compound 2 following the administration regimen of 80 mg/kg dosage, orally (po), and once every two days (q2d) is evaluated in the model (corresponding to the number 57 regimen in table 7). The experiment has two groups, and 15 animals in each group, in one group, 5 animals are used for the analysis of the proportion of CD45+ AML cells, and the remaining 10 animals are used for recording the living condition of the mice. 18 days after the cell inoculation, according to the experimental regimen, 5 animals are selected randomly from each group, bone marrow and spleen are collected, the proportion of human CD45+ AML cells in bone marrow and spleen is analyzed using flow cytometry to evaluate the disease burden of animals.

Figure 9A:
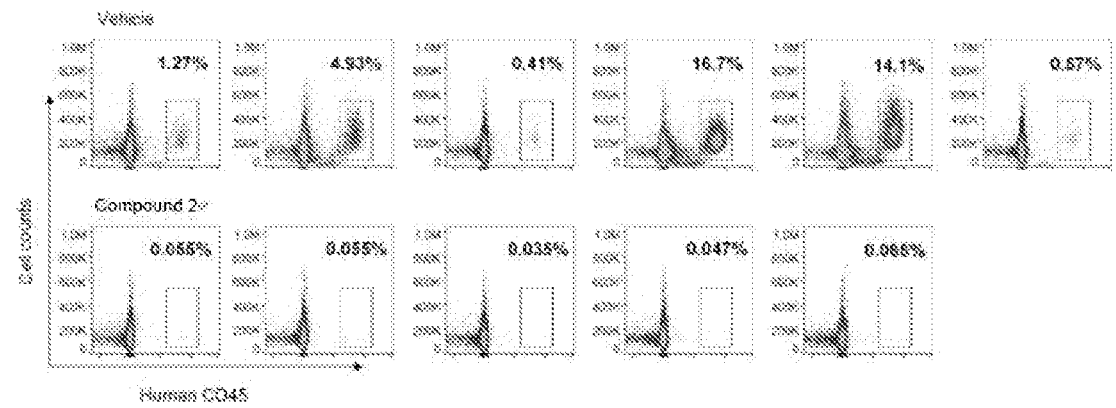
FIG. 9A. Flow analysis chart of human CD45+ AML cells in bone marrow with compound 2.
Figure 9B:
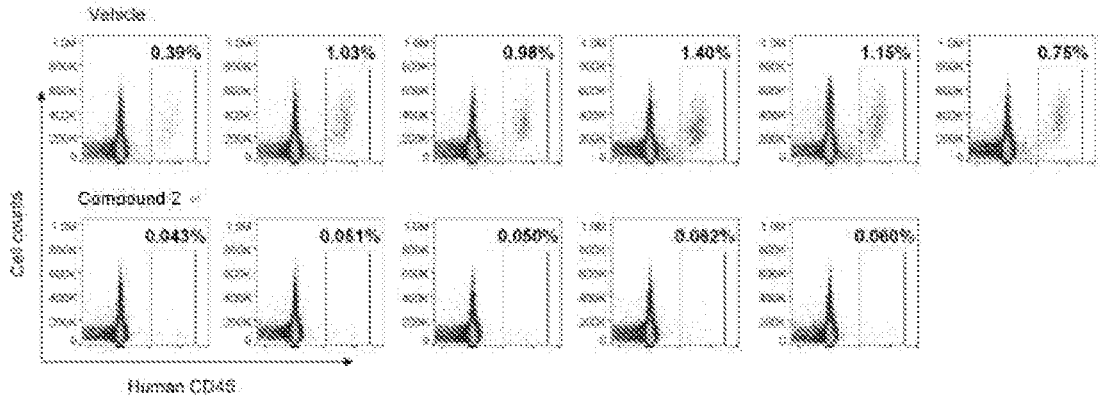
FIG. 9B. Flow analysis chart of human CD45+ AML cells in spleen with compound 2.
Figure 9C:
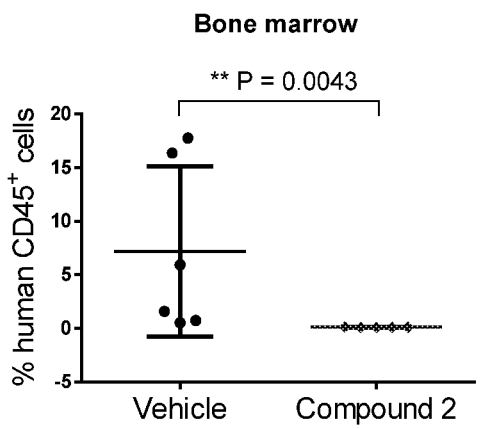
FIG. 9C. Summary analysis chart of the proportion of human CD45+ AML cells in bone marrow with compound 2.

As shown in FIGS. 9A and 9B, compound 2 significantly reduces the proportion of human CD45+ cells in mouse bone marrow and spleen of human-derived MOLM-13 AML mouse xenograft tumor. FIG. 9A is the flow analysis figure of human CD45+ AML cells in bone marrow; FIG. 9B is the flow analysis figure of human CD45+ AML cells in spleen; FIGS. 9C and 9D are summary analysis charts of the proportion of human CD45+ AML cells in bone marrow and spleen; In the figures, the proportion of CD45+ AML cells is the proportion accounting for all living cells, and is statistically analyzed by Mann-Whitney U test method. In the vehicle group, on the day of analyzing the proportion of human CD45+ AML cells, the body weight loss of one mouse for recording the living condition >20% achieves the Humane endpoint, so the animal is euthanized, then bone marrow and spleen for analyzing the proportion of human CD45+ AML cells are collected, as shown, the vehicle group n=6, and the compound 2 group n=5.

The results show that in the vehicle control group, the proportion of human CD45+ AML cells has a relatively large individual difference within the group, wherein the proportion of CD45+ AML cells in bone marrow is between 0.41% and 16.7%, and the proportion in spleen is 0.39% to 1.40%. However, in the compound 2 administration group, all the proportion of human CD45+ AML cells in bone marrow and spleen of experimental animals is less than 0.1%, and comparing the two groups of data, they have a statistically significant difference. Above data show that compound 2 can significantly reduce the leukemia burden of mice.

The survival analysis shows that, as shown in FIG. 10, P<0.0001, the administration of compound 2 or vehicle starts on the third day after the MOLM-13 cell inoculation, n=10. The survival curves of the two animal groups are analyzed and compared using a log-rank method. On the 15th day after starting the administration treatment, animals began to die in the vehicle control group, and on the 21th day, all the animals died. As shown in table 2, the median survival of animals in the vehicle control group is 18.5 days, and compound 2 treatment (80 mg/kg) can prolong the median survival by 18.5 days (prolong 100%), achieving 37.0 days.

Since the established MOLM-13 is a diffuse systemic system tumor, both its degree of malignancy and progression of disease are relatively dangerous. The results show that compound 2 significantly prolongs the survival time of mice bearing human MOLM-13 (AML) xenograft tumors, and compound 2 significantly prolongs the median survival time of mice bearing human MOLM-13 (AML) xenograft tumors, and compound 2 has a significant anti-AML effect as a single drug.

TABLE 2

| Compound 2 significantly prolongs median survival time of mouse bearing human MOLM-13 (AML) xenograft tumor | | |
|---|---|---|
| | Vehicle control group | Compound 2 (80 mg/kg) |
| Median survival | 18.5 days | 37.0 days |
| Prolonged days of survival | — | 18.5 days |
| P value (log-rank) | <0.0001 | |

5.2. Anti-MDS Effect of Compound 2 Alone in Dimethylbenzanthracene Induced Rat Myelodysplastic Syndrome (MDS) Model Myelodysplastic syndromes (MDS) are a group of heterogeneous myeloid clonal diseases derived from hematopoietic stem cells, which are characterized by differentiation and developmental abnormalities of myeloid cells, exhibiting as ineffective hematopoiesis, refractory cytopenia, hematopoietic failure and high Risk of being transformed to acute myeloid leukemia (AML). Multiple human-derived rat MDS model is used for evaluating the in vivo anti-tumor effect of compound 2 alone. Table 3 shows that the anti-tumor effect in dimethylbenzanthracene-induced rat myelodysplastic syndrome (MDS) model, compound 2 is administered following an oral (po) and once every two days (q2d) regimen.

TABLE 3

Anti-tumor effect of compound 2 in dimethylbenzanthracene-induced rat myelodysplastic syndrome (MDS) model

| Model (Indication) | drug | Animal No. | Animal strain | Dosage of compound 2 | Compound 2 Administration route and regimen | Combination administration regimen |
|---|---|---|---|---|---|---|
| Dimethylbenzanthracene-induced rat myelodysplastic syndrome model (MDS) | Alone | 23 | SD rat | 10, 30 mg/kg | p.o., q2d × 3 w | — |

Note:
q2d is once every other day; d is the number of days; w is the number of weeks.

The rat myelodysplastic syndrome (MDS) model is constructed using a chemical mutagenic agent dimethylbenzanthracene (DMBA). in the rat MDS model, the changes of myelogram and hemogram are similar to that of human myelodysplastic syndromes, and it is confirmed that it can be used for the anti-MDS effect study of drugs. DMBA is administered at 50 mg/kg, i.v. Following the once per week regimen for 4 weeks totally to establish the rat MDS model. One week after the end of DMBA administration (day 28), peripheral blood is collected from the caudal vein for routine blood test to determine whether the model is established successfully.

The results of the routine blood test show that all the total platelet count (PLT), erythrocyte count (RBC), number of reticulocytes (RET), hemoglobin (HGB) and total white blood cell count (WBCB) of the rats receiving DMBA treatment are significantly reduced compared with that of normal animals. The animals are randomly divided into groups according to the PLT level on day 28, wherein a vehicle control group (Vehicle), two dosage groups of compound 2 (10 mg/kg) and compound 2 (30 mg/kg) (corresponding to the number 23 regimen in table 3), and healthy control group (naive) are totally set, each group has 5 animals.

Figure 11A:
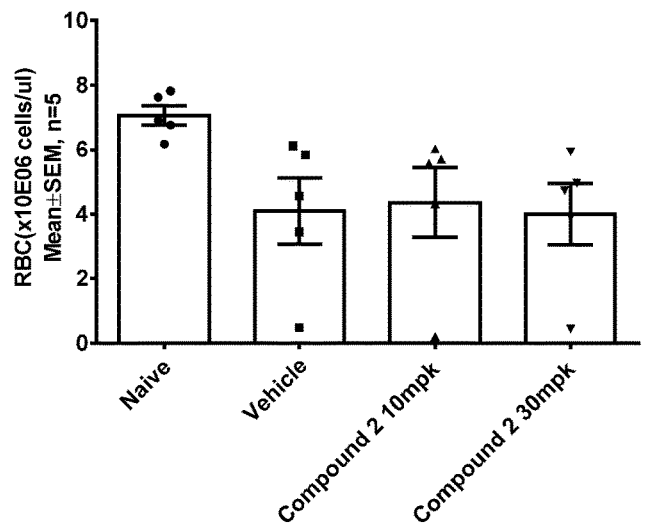
FIG. 11A. Representation diagram of MDS in which peripheral blood PLT and WBC levels are significantly declined in rats induced by DMBA before being grouped and treated.

As shown in FIG. 11A, MDS in which peripheral blood PLT and WBC levels are significantly declined in rats induced by DMBA before being grouped and treated. After DMBA administration, the animals are randomly divided into groups according to the PLT level, the PLT and WBCB levels of the vehicle control group and two dosage groups of compound 2 are comparable, but both are lower than that of the healthy control group ($P<0.0001$). The RBC levels of the vehicle control group and two dosage groups of compound 2 are slightly reduced compared with that of the healthy control group, but they have no statistically significant difference.

Figure 11B:
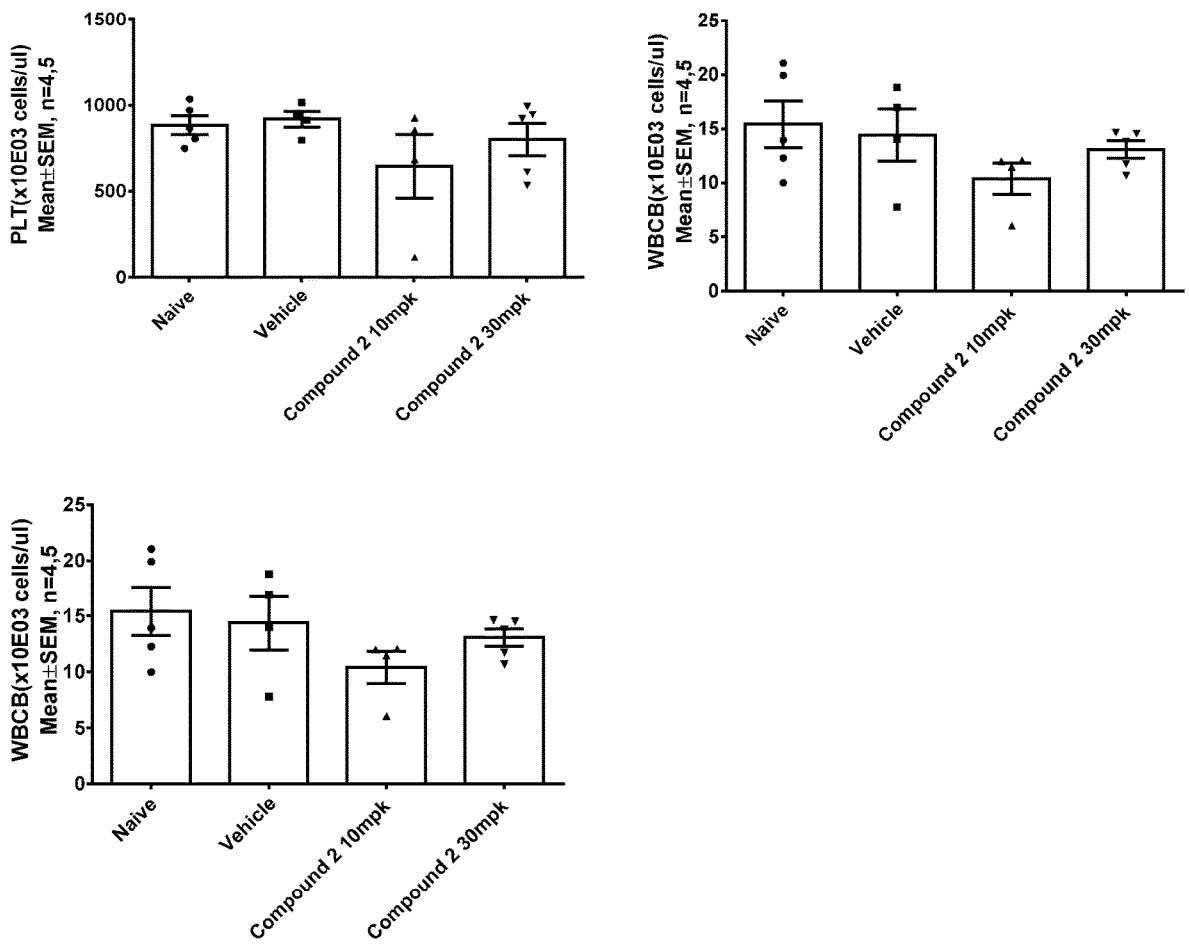
FIG. 11B. Schematic diagram of compound 2 alone having no significant effect on peripheral blood PLT, WBC and RBC levels in MDS rats.

Compound 2 is administered following 10 mg/kg or 30 mg/kg, p.o., q2d×21 d regimens. After the administration, the peripheral blood and bone marrow cells from each group of animals for routine blood analysis. The routine blood analysis of the peripheral blood, the result as shown in FIG. 11B, compound 2 alone has no obvious effect on PLT, WBCB and RBC levels of the peripheral blood of MDS rats.

Figure 11C:
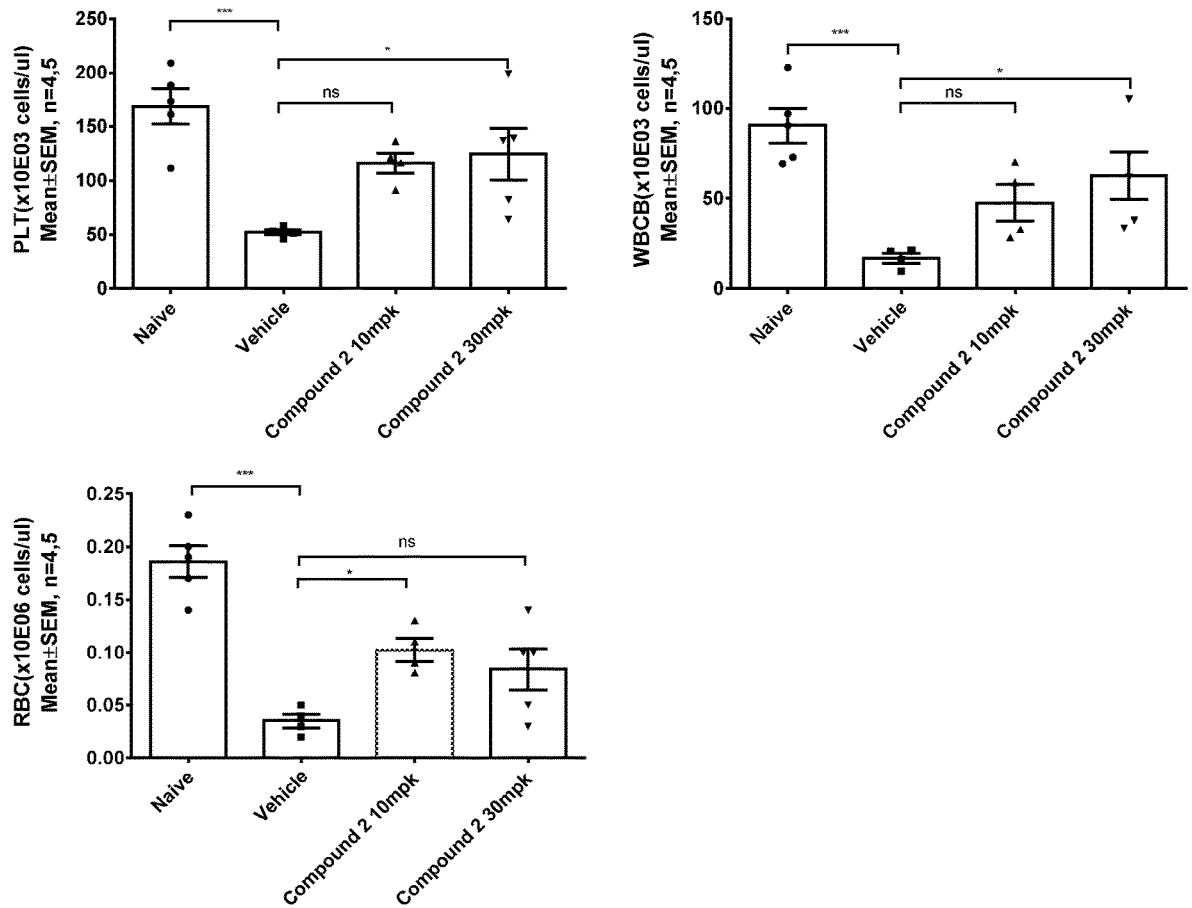
FIG. 11C. Schematic diagram of compound 2 alone being capable of significantly recovering bone marrow PLT, WBCB and RBC levels in MDS rats.

However, the routine bone marrow analysis, the result as shown in FIG. 11C, compound 2 alone can significantly recover the PLT, WBCB and RBC levels of bone marrow of MDS rats. Specifically, the average PLT value of bone marrow of the healthy control rats is 168±16.44 (cells/μl), and the average PLT value of bone marrow of rats in the MDS model group is 52±2.49 (cells/μl), which has a statistically significant difference compared with that of the healthy control group ($P<0.001$). However, the PLT levels of bone marrow of rats receiving treatments with compound 2 (10 mg/kg) and compound 2 (30 mg/kg) all rise, and the average values are 116±9.35 (cells/μl, compared with the MDS model group, $P>0.05$) and 124.2±23.8 (cells/μl, compared with the MDS model group, $P<0.05$).

In another aspect, in the result of the routine bone marrow analysis, average WBCB value of the rats in the control group is 90.42±9.65 (cells/μl), and the average WBCB value of bone marrow of rats in the MDS model group is 16.89±2.75 (cells/μl), which has a statistically significant difference compared with that of the rats in the healthy control group ($P<0.001$). The WBCB levels of bone marrow of rats receiving treatments with compound 2 (10 mg/kg) and compound 2 (30 mg/kg) all rise, and the average values are 47.5±10.13 (cells/μl, compared with the vehicle control group, $P>0.05$) and 62.53±13.08 (cells/μl, compared with the MDS model group, $P<0.05$).

Furthermore, the average RBC value of the rats in the healthy control group is 0.19±0.02 (cells/μl), and the average RBC value of bone marrow of rats in the MDS model group is 0.04±0.01 (cells/μl), which has a statistically significant difference compared with that of the rats in the healthy control group ($P<0.001$). The RBC levels of bone marrow of rats receiving treatments with compound 2 (10 mg/kg) and (30 mg/kg) all rise, and the average values are 0.10±0.01 (cells/μl, compared with the MDS model group, $P<0.05$) and 0.08±0.02 (cells/μl, compared with the vehicle control group, $P>0.05$).

The in vitro MDS results show that after the administration of the animals in the MDS model group, the PLT, WBCB and RBC levels are compared with that of the animals in the healthy control group, all are significantly reduced, also show that at the time points be detected, the experimental animals still have a MDS hematological change. Compound 2 administration can significantly recover the PLT, WBCB and RBC levels of MDS bone marrow.

5.3. Anti-Tumor Effect of Compound 2 in Combination with Azacitidine in Mouse Xenograft Tumor Model of Human MOLM-13 AML In the in vitro experiment, TP53 wild type of MOLM-13 cell line is moderately sensitive to compound 2. Systemic tumor model is established by inoculating MOLM-13 tumor cells through caudal vein, the administration starts on the third day after the cell inoculation, and the day of the administration is defined as the first day. Compound 2 is administered following 30 mg/kg, q2d regimens for 21 days.

Azacitidine is administered following 1.5 mg/kg, qd regimens for seven days (corresponding to the number 81 regimen in table 7).

Figure 12:
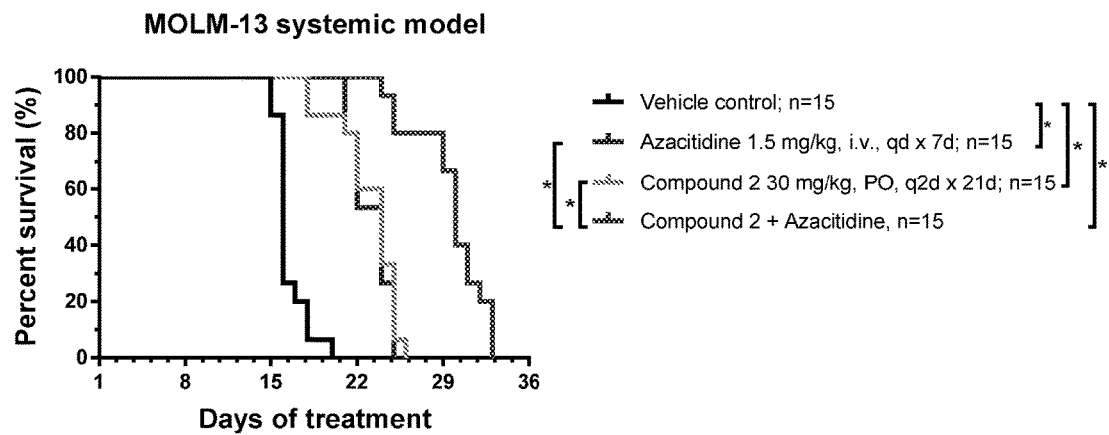
FIG. 12. Analysis comparison chart of survival curve of compound 2 in combination with Azacitidine in two groups of animals.

As shown in FIG. 12, the administration of compound 2 or vehicle starts on the third day after the MOLM-13 cell inoculation, n=15. The survival curves of the two animal groups are analyzed and compared using a log-rank method. The result is corrected by Bonferroni multiple test, P<0.05. See table 4, mice in the vehicle control group began to die on the 15th day (17 days after the cell inoculation), and on the 20th day, all the mice die, the median survival is 16 days. The median survival time of animals in the compound 2 administration group is 24 days (compared with the vehicle control group, P<0.01). Azacitidine alone also can significantly prolong the mouse survival, and the median survival time is 24 days (compared with the vehicle control group, P<0.01). The group of compound 2 in combination with azacitidine can further prolong the mouse survival time, and the median survival time achieves 30 days (compared with the vehicle control group, the group of compound 2 alone and the group of Azacitidine, all P values<0.01).

TABLE 4

Compound 2 in combination with Azacitidine significantly prolongs median survival time of mouse bearing human MOLM-13 (AML) xenograft tumor

| | Vehicle control group | Compound 2 30 mg/kg | Azacitidine 1.5 mg/kg | Compound 2 and Azacitidine |
|---|---|---|---|---|
| Median survival (days) | 16 | 24 | 24 | 30 |
| Prolonged survival (days) | — | 8 | 8 | 14 |

The results show that in the oral administration regimen, the tumor growth inhibition effect of compound 2 alone on mouse xenograft tumor of MOLM-13 human AML cells is significant. At a well-tolerated dosage, the combined treatment of compound 2 and Azacitidine can significantly prolong the survival time of mice bearing human MOLM-13 (AML) xenograft tumors, and in the MOLM-13 systemic tumor model, it significantly prolongs the survival time of mice.

5.4. Anti-Tumor Effect of Compound 2 in Combination with Azacitidine or Decitabine in Mouse Xenograft Tumor Model of Human OCI-AML-3 AML In the in vitro cell experiment, OCI-AML-3 is a human AML cell line which is relatively sensitive to the treatment with compound 2, and the IC50 value is 315.6±97 nM. A mouse xenograft tumor model is established using OCI-AML-3 cells to evaluate the anti-AML effect of compound 2 in combination with Azacitidine or Decitabine.

Figure 13A:
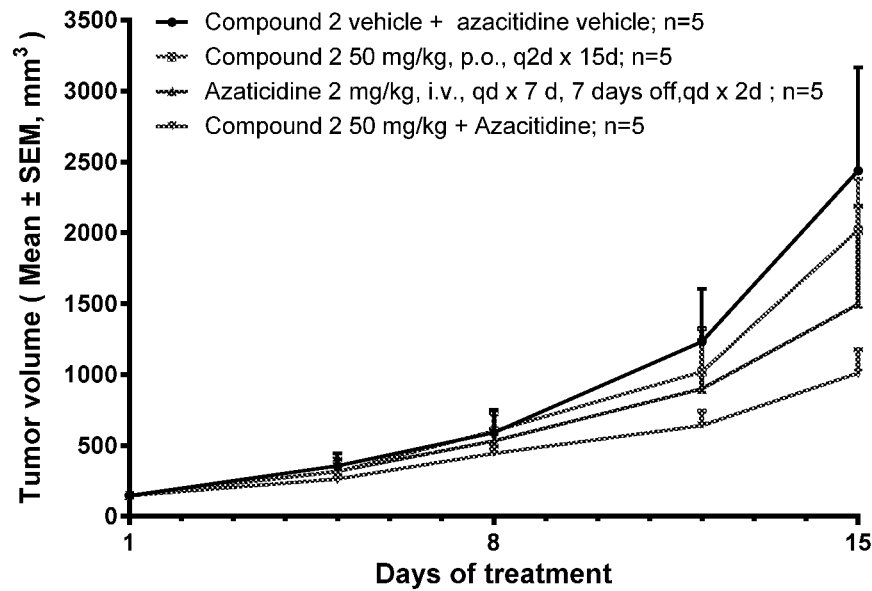
FIG. 13A-B. Tumor growth inhibiting curve chart (A) and body weight change chart in mice (B) of compound 2, Azacitidine and the combination of the two.
Figure 13B:
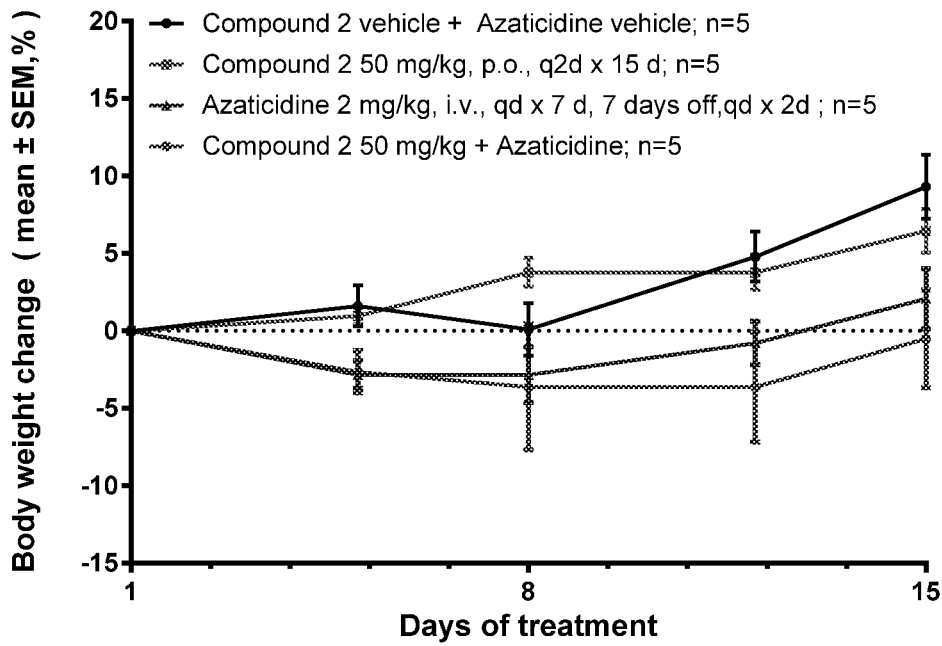

As shown in FIG. 13A and table 5, in the model, compound 2 is administered following 50 mg/kg dosage, orally, q2d×15 day regimen, it cannot inhibit the tumor growth, and the T/C value is 84.8% (P>0.05). Azacitidine is administered following 2 mg/kg, caudal vein injection, qd×7d, drug withdrawal 7 days, then qd×2 day regimens for seven days (corresponding to the number 68 regimen in table 7). At the end of the experiment (d15), they all do not show a significant anti-tumor activity, and the T/C value is 56.6% (P>0.05). Compound 2 (50 mg/kg) in combination with Azacitidine (2 mg/kg) exhibits an obvious enhanced anti-tumor effect, the T/C value is 43.4%, and the synergistic factor is 1.11. The result shows that the combined administration has a synergistic effect.

TABLE 5

Anti-tumor effect of compound 2 in combination with Azacitidine in mouse xenograft tumor model of human OCI-AML-3 AML

| Treatment | Relative tumor volume (RTV, Mean ± SEM) | T/C value (%) (d15) | Synergistic factor [a] |
|---|---|---|---|
| Compound 2 vehicle + normal saline | 16.5 ± 4.1 | — | — |
| Compound 2/50 mg/kg | 14.0 ± 2.7 | 84.8 | — |
| Azacitidine/2 mg/kg | 9.3 ± 3.2 | 56.6 | — |
| Compound 2/50 mg/kg + Azacitidine/2 mg/kg | 7.2 ± 1.3 | 43.4 | 1.11 |

Figure 14A:
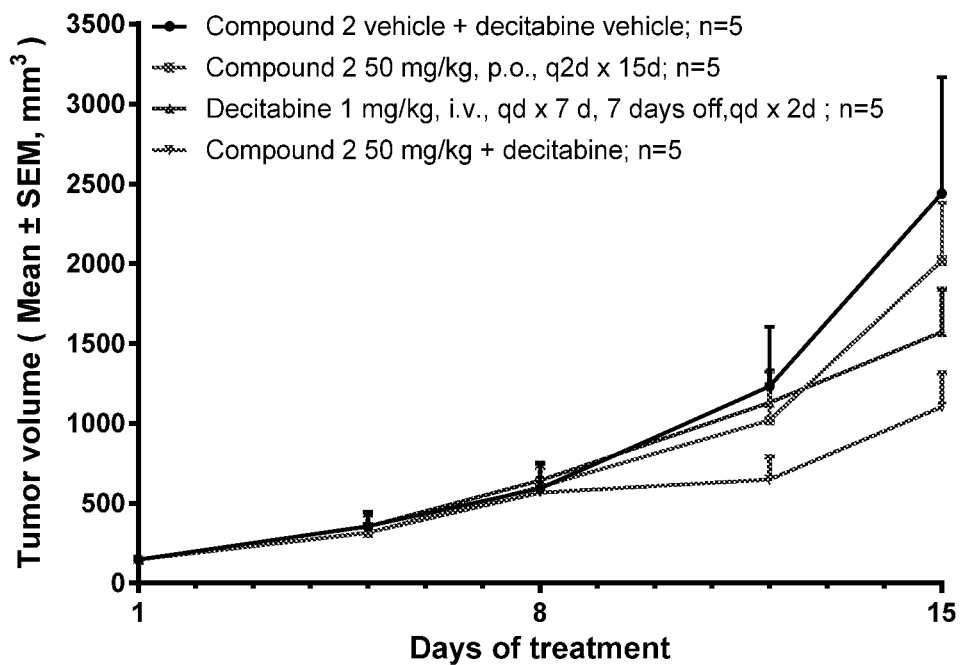
FIG. 14A-B. Tumor growth inhibiting curve chart (A) and body weight change chart in mice (B) of compound 2, Decitabine and the combination of the two.
Figure 14B:
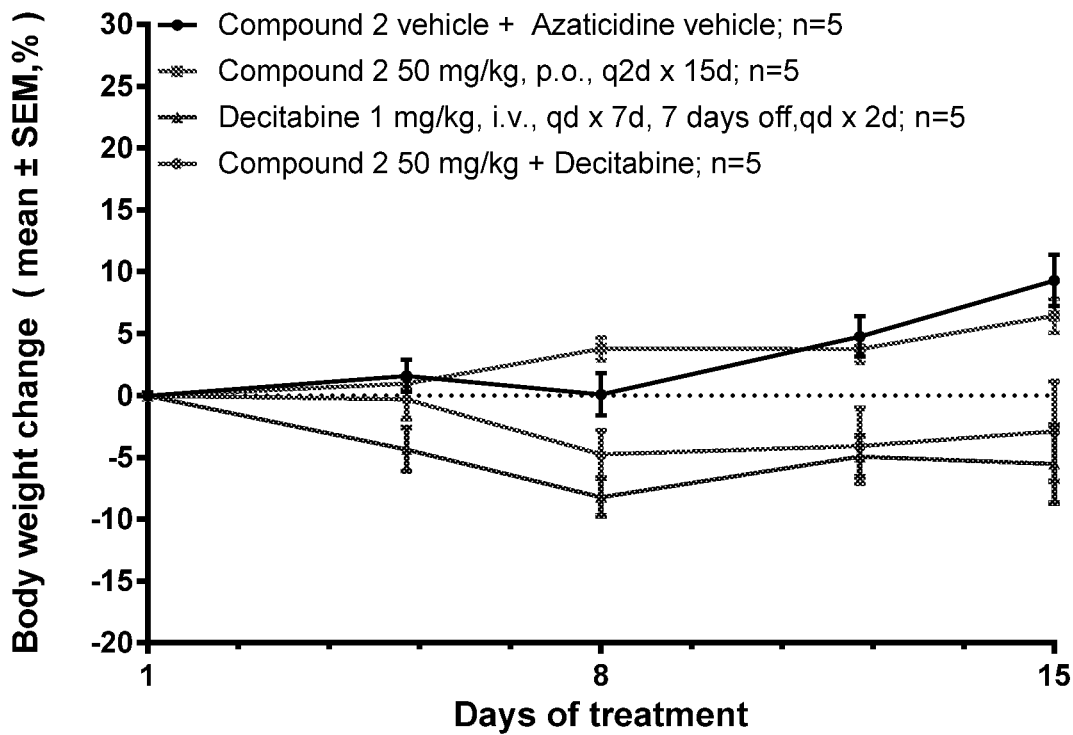

Note:
Normal saline is the vehicle of Azacitidine;
[a] synergistic factor:
>1 synergistic effect,
= 1 additive effect,
and <1 antagonistic effect As shown in FIG. 14A and table 6, Decitabine (1 mg/kg) is administered following caudal vein injection, qd×7d, drug withdrawal 7 days, then qd×2 day regimen. At the end of the experiment (d15), it also does not show an obvious anti-tumor activity, and the T/C value is 64.9% (P>0.05). However, Compound 2 (50 mg/kg) in combination with Decitabine (1 mg/kg) exhibits an obvious enhanced anti-tumor effect, and 15 days after the administration, the T/C value is 44.9%. Synergistic analysis shows that the combined administration of the two drugs has a synergistic effect, and the synergistic factor is 1.22.

The results show that compound 2 in combination with Azacitidine or Decitabine is better than Azacitidineanr and Decitabine which are used alone from the perspective of RTV value, T/C value and synergistic factor. No significant body weight loss is observed in each treatment group.

TABLE 6

Anti-tumor effect of compound 2 in combination with Decitabine in mouse xenograft tumor model of human OCI-AML-3 AML

| Treatment | Relative tumor volume (Mean ± SEM) | T/C value (%) (d15) | Synergistic factor [a] |
|---|---|---|---|
| Compound 2 vehicle + normal saline | 16.5 ± 4.1 | — | — |
| Compound 2/50 mg/kg | 14.0 ± 2.7 | 84.8 | — |
| Decitabine/1 mg/kg | 10.7 ± 1.7 | 64.9 | — |
| Compound 2/50 mg/kg + Decitabine/1 mg/kg | 7.4 ± 1.0 | 44.9 | 1.22 |

Note:
Normal saline is the vehicle of Decitabine;
[a] synergistic factor:
>1 synergistic effect,
= 1 additive effect,
and <1 antagonistic effect

5.5. In Vivo Anti-Tumor Effects of Compound 2 Alone or in Combination in Human-Derived MOLM-13 and OCI-AML-3 AML Mouse Xenograft Tumor Models The response rate of both Azacitidine and Decitabine is relatively low in newly diagnosed and advanced AML patients. The comprehensive response rate of complete remission and complete remission with incomplete count recovery generally is 20% to 30% (Kim et al., 2015). Even if continuously receiving Aza and Dec treatment, all the patients will develop recurrent diseases. The mouse xenograft tumor model of multiple human-derived AML cancer cells is used for evaluating the in vivo anti-tumor effect of compound 2 alone or in combination. Table 7 shows that the anti-tumor effect in the mouse xenograft tumor model of human-derived AML cancer cells, and compound 2 is administered following an oral (po) and once every two days (q2d) regimen.

Figure 15:
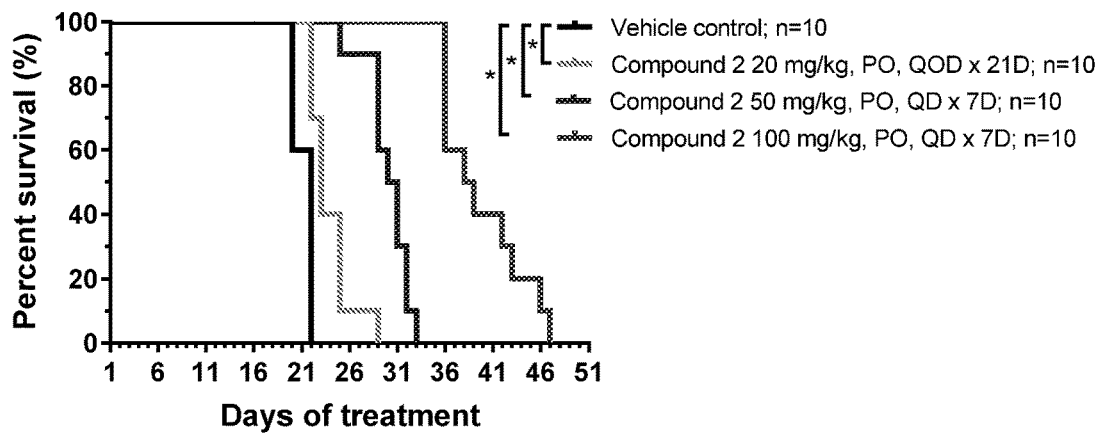
FIG. 15. Compound 2 alone dose-dependent significantly prolongs the survival of xenograft tumor mice with MOLM-13 systemic AML. NOD SCID mice implanted with $1\times10^7$ MOLM-13 cells (n=10/group) three days after cell implantation are treated with a carrier, 20 mg/kg (oral administration, every other day for 21 days), 50 mg/kg (oral administration, once a day for 7 days) or 100 mg/kg (oral administration, once a day for 7 days) of compound 2. The data are shown as the Kaplan-Meier curve depicting mouse survival. Logarithmic rank test using Bonferroni multiple test is used for survival curve comparison, * $P<0.05$.

As shown in FIG. 15, the treatment using 20 mg/kg compound 2 alone significantly prolongs the survival of MOLM-13 systemic AML xenograft expressing wild type TP53. NOD SCID mice implanted with $1\times10^7$ MOLM-13 cells (n=10/group) three days after cell implantation are treated with a carrier, 20 mg/kg (oral administration, every other day for 21 days), 50 mg/kg (oral administration, once a day for 7 days) or 100 mg/kg (oral administration, once a day for 7 days) of compound 2. The data are shown as the Kaplan-Meier curve depicting mouse survival. Logarithmic rank test using Bonferroni multiple test is used for survival curve comparison, * P<0.05.

The above results show that in the mouse systemic xenograft tumor model of human MOLM-13 AML, compound 2 shows a significant tumor growth inhibition effect, and in dimethylbenzanthracene-induced rat myelodysplastic syndrome (MDS) model, it shows a significant anti-MDS effect. In the combined administration, in the mouse systemic xenograft tumor model of human MOLM-13 AML and the mouse subcutaneous xenograft tumor models of human OCI-AML-3 AML, compound 2 in combination with other anti-cancer agents can obtain a better anti-tumor effect than which can be obtained by each of them alone, thus achieving a synergistic effect. In the studies of single drug and combined administration, the tumor bearing animals have a good tolerance to the above-mentioned treatments, and show that compound 2 can be used for the clinic treatments of AML and MDS as a single drug or in combination with other therapeutic agents.

In this study, we test one of the most effective MDM2 inhibitors (compound 2) as a single drug or in combination with other therapeutic agents in AML cell lines and xenograft. The in vitro experiment demonstrates that compound 2 has an effective anti-proliferative activity on TP53 wild type AML cell lines. The anti-proliferative activity is particularly significant in TP53 wild type and FLT3-ITD mutant

TABLE 7

Anti-tumor effect of compound 2 in human-derived AML and ALL cell mouse xenograft tumor model

| Model (Indication) | Drug | Mouse No. | Mouse strain | Dosage (Compound 2) | Administration route and administration regimen (Compound 2) | Combination administration regimen |
|---|---|---|---|---|---|---|
| MOLM-13 (AML) | Alone | 57 | NOD SCID | 80 mg/kg | p.o., q2d × 3 w | — |
|  | Combination | 81 | NOD SCID | 30 mg/kg | P.o., q2d × 3 w | Azacitidine 1.5 mg/kg, i.v., qd × 7 d |
|  | Combination | 15 | NOD SCID | 50 mg/kg | p.o., qd × 7 d | Azacitidine 2 mg/kg, i.v., qd × 7 d |
| OCI-AML-3 (AML) | Combination | 68 | NOD SCID | 20, 50 mg/kg | p.o., q2d × 3 w | Azacitidine 2 mg/kg, i.v, qd × 7 d, 7 days off, qd × 2 d; Decitabine, 1 mg/kg, i.v, qd × 7 d, 7 days off, qd × 2 d; |

Note:
qd is once a day; q2d is once every other day; d is the number of days; w is the number of weeks.

Figure 16:
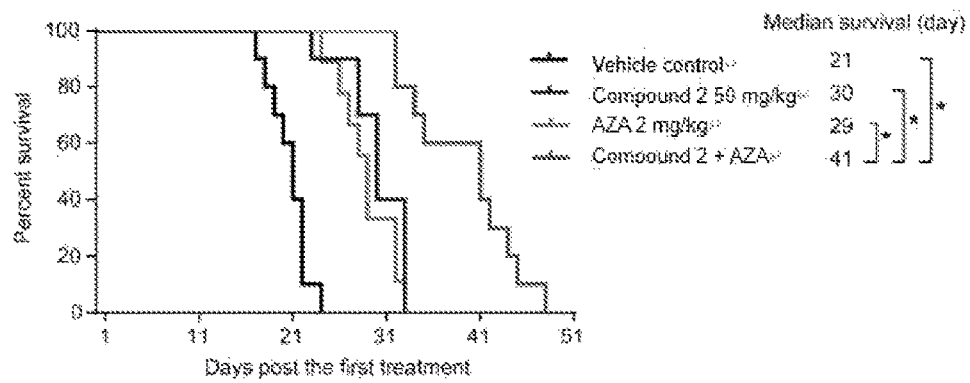
FIG. 16. Compound 2 enhances the in vivo anti-leukemia activity of Aza or Dec in the AML xenograft model.
Figure 16:
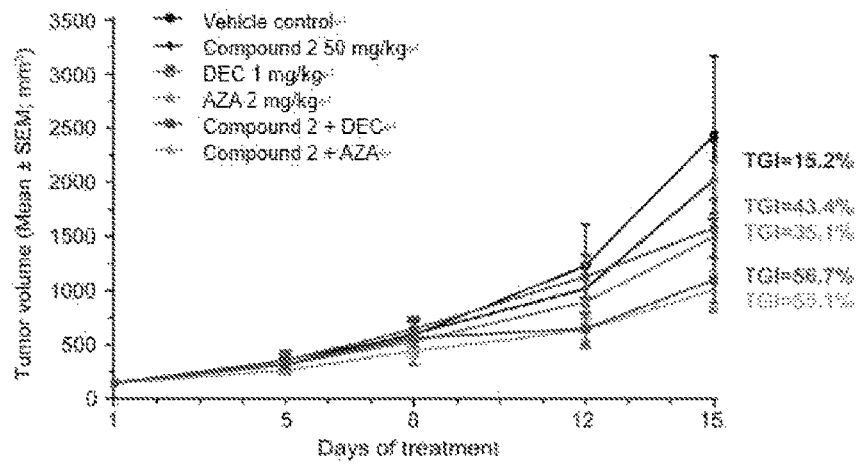

As shown in FIG. 16, compound 2 enhances the in vivo anti-leukemia activity of Aza or Dec in the AML xenograft model.

(A) NOD SCID mice implanted with $1\times10^7$ MOLM-13 cells (n=15/group) three days after cell implantation are treated with a carrier, 50 mg/kg of compound 2 (each day PO for 7 days) and 2 mg/kg Aza (each day for 7 days) alone or in combination. The data are shown as the Kaplan-Meier curve depicting mouse survival. Logarithmic rank using Bonferroni multiple comparisons is used for survival comparison. *P<0.05.

(B) NOD SCID mice carrying a subcutaneous OCI-AML-3 tumor are treated with 50 mg/kg compound 2 (every other day PO for 15 days), 2 mg/kg Aza (each day IV for 7 days) and 1 mg/kg Dec (each day IV for 7 days) alone or in combination, and the tumor growth inhibition (TGI) is determined.

type AML cells. In the combined treatment, compound 2 enhances the anti-proliferative activity of other therapeutic agents (comprising demethylation drugs (Azacitidine and Decitabine) and chemotherapeutic agent Cytarabine). In human MOLM-13 systemic xenograft, treatment with compound 2 alone significantly inhibits the tumor growth, and the minimum effective dosage is 20 mg/kg. Higher dosage of compound 2 (80 mg/kg) achieves a stronger anti-tumor activity. When compound 2 is used in combination with: (1) Azacitidine in subcutaneous OCI-AML-3 and systemic MOLM-13 model; (2) Decitabine in subcutaneous OCI-AML-3 model, the enhanced anti-leukemia activity is recorded.

Notably, AML is a highly heterogeneous disease with a complex karyotype. In the disease, FLT3 and NPM1 are most common mutant genes. In newly emerging AML, the mutation frequencies of FLT3 and NPM1 are up to 28% and 27% respectively. As described above, compound 2 as a single drug has an effective anti-leukemia activity in AML cells carrying FLT3-ITD mutation in vitro and in vivo. In the MOLM-13 AML systemic xenograft model carrying FLT3-ITD mutation, compound 2 alone can significantly alleviate the disease burden and prolong the mouse survival. Compared with single drug, the combined treatment of compound 2 and Azacitidine or an FLT3 inhibitor achieves a stronger anti-AML activity. In the OCI-AML-3 AML xenograft model carrying NPM1 mutation, the combined treatment of compound 2 and demethylation drugs (Azacitidine and Decitabine) and traditional chemotherapeutic drug Cytarabine (Ara) generates a synergetic anti-AML effect. These results show that compound 2 has an extensive application potential in AML showing FLT3 and NPM1 mutations.

Embodiment 6. Phase I Clinical Study of Dose Escalation of Compound 2 Alone and in Combination with Azacitidine or Cytarabine The object of this study is to determine the safety and tolerance of compound 2 alone and in combination with Azacitidine or Cytarabine in patients with hematologic tumors, such as adult relapsed or refractory acute myeloid leukemia (R/R AML) and relapsed or refractory high risk/extremely high risk myelodysplastic syndrome (MDS). Experimental Drugs, Dosages and Administration Method Experimental drugs Compound 2 is in capsules, each capsule contains 2 5 mg or 50 mg compound 2, and the only excipient is microcrystalline cellulose. The experimental drug compound 2 should in a sealed storage away from sunlight at 2° C.-8° C.

The dosage of Compound 2 is escalated following the standard 3+3 regimen, wherein the initial dosage is 150 mg, and is escalated orderly to 200 mg, 250 mg, and 300 mg, is taken orally once a day (QD), is brought into use at the first day in each cycle, is continuously taken for 7 days, then is discontinued for 21 days, and each 28 days is an administration cycle.

When the first stage of dose escalation of compound 2 alone is completed, a second stage, i.e. the combination administration with dose escalation of compound 2, can be entered. In the combination administration regimen, the dosage of compound 2 is started at 100 mg, and is escalated orderly to 150 mg and 200 mg. Azacitidine is at a fixed dosage, 75 mg/m$^2$ subcutaneous injection, once a day, is brought into use at the first day in each cycle, is continuously taken for 7 days, then is discontinued for 21 days, and each 28 days is an administration cycle. Cytarabine is at a fixed dosage, 1 g/m$^2$ subcutaneous injection, and the intravenous infusion time is not less than 4 hours, once a day, is brought into use at the third day in each cycle, is continuously taken for 5 days, then is discontinued for 21 days, and each 28 days is an administration cycle. Azacitidine or Cytarabine is administered 4 hours after the oral administration of compound 2. After the combined treatment of two drugs, a rest period is entered.

Embodiment 7. Treating AML Cells with Compound 2 in Combination with DEC, AZA or Ara-C, Synergistically Activating P53 Pathway, and Down-Regulating Genes Involving Cell Cycle Progression and Mismatch Repair In order to find out the potential action mechanism of compound 2 in combination with AZA or Ara-C, we use MOLM-13 cells treated with compound 2, AZA or Ara-C alone or in combination for 24 hours for RNA-Seq analysis. Differential gene expression analysis shows that the differential gene expression amount of treatment with compound 2 in combination with AZA or Ara-C is the most compared with DMSO control (FIGS. 17A-B). KEGG signaling pathway analysis shows that using compound 2 in combination with AZA results in the up-regulation of related genes in p53 signaling pathway, and the down-regulation of genes related to DNA replication, mismatch repair and cell cycle progression (FIG. 17C). The combination of compound 2 and Ara-C results in the up-regulation of related genes in p53 signaling pathway, and the down-regulation of genes related to the cell cycle (FIG. 17D). In view of compound 2 and AZA or Ara-C synergistically up-regulating p53 related pathway, the differential expression of p53 regulatory genes is further analyzed. Heat map result shows that compound 2 can induce a significant up-regulation of p53 target genes in MOLM-13 cells in vitro. In general, the inductive effect of the two in combination is obviously better than the two drugs alone (FIGS. 17E-F). These comprise P53 activation marker GDF15 (also known as MIC-1), pro-apoptotic genes, BBC3 (encoding PUMA), MDM2, BAX and FAS, and negative regulatory factors related to cell cycle progression, CDKN1A (encoding P21) and GADD45. Similarly, after the treatment of compound 2+AZA or Ara-C in combination, both SESN1 and SESN2 rise, and both the two are negative regulatory factors of MTORC1. After the combined treatment, after comprising CDC20, CCNB1 and PLK1, the oncoprotein encoding genes involving cell cycle progression are significantly down-regulated. In genes involving DNA replication, such as MCM4 and MCM2, similar effect is also observed. In the combined treatment of compound 2+Ara-C, the level of increase of P53 regulatory genes is more significant. These data indicate that treatment with compound 2 in combination with DEC, AZA or Ara-C can synergistically activate P53 pathway, and down-regulate genes involving cell cycle progression and mismatch repair.

As shown in FIG. 17, (A-B) charts show that after being affected by compound 2 and AZA or Ara-c alone or in combination for 24 hours, the number of differentially expressed genes is statistically significant. (C-D) After being treated with compound 2 and AZA or Ara-c in combination, the signaling pathway which is changed most significantly. (E-F) In MOLM-13 cells, with regard to compound 2 and AZA or Ara-C alone or in combination, the change of some p53 regulatory genes.

Embodiment 8. AML Cells are Treated with Compound 2 and DEC, AZA or Ara-C in Combination, DNA Damage can be Induced, and P21 Expression is Up-Regulated Synergistically Therefore, we evaluate the protein changes involving these identified signaling pathways. As shown in FIGS. 18A-C, the combined treatment can significantly increase DNA damage, which is demonstrated by γ-H2AX expression quantity. As described above, after compound 2 activates P53, it further induces the accumulation of P53 and P21. DEC and AZA are low methylation drugs inducing low DNA methylation in cells by inhibiting the function of methyltransferase I (DNMT1). Many studies indicate that DNMT1 forms a complex with UHRF1 and HDAC1 proteins in tumor cells, which binds and inhibits the expression of various oncogene (such as P16INK4A, P14ARF and P21) promoters, and promotes tumor growth. Cytarabine is a pyrimidine nucleoside analogue, which induces DNA damage, further activates ATM/ATR-P53-P21 signal cascades, inhibits DNA synthesis in cells and interferes with cell proliferation.

Based on above evidences, we further detect the regulating effect of treatment with compound 2 in combination with low methylation drugs DEC and AZA or drug Ara-C on P53, demethylation marker protein DNMT1 and common target protein P21, and the expression of apoptosis marker protein, lytic PARP-1. Being consistent with the expectation, cancer cells expressing wild type TP53 are treated with compound 2, P53 is stabilized, P53 pathway is activated, and results in the accumulations of P53 and P21. Treatment with AZA or DEC almost completely eliminates DNMT1. Ara-C alone has a significant up-regulation effect on P21. Most importantly, compared with single drug treatment, treatment with compound 2 and DEC, AZA or Ara-C in combination can synergistically up-regulate P21 protein (FIGS. 16D-F). Additionally, compound 2 synergistically effects with DEC, AZA or Ara-C, induces the generation of apoptosis marker, i.e. PARP-1 lysis (FIGS. 18D-F). RG-7388 is introduced as the comparison of present experiment. Its effect on P53 and P21 is similar to that of compound 2. RG-7388 in combination with DEC, AZA and Ara-C also can significantly up-regulate the expression of P53 and P21, and further induce the generation of PARP-1 lysis (FIGS. 18D-F). The potential action mechanism is as shown in FIG. 18. In short, compound 2 is a small molecule inhibitor interacting with MDM2-P53. It eliminates the inhibiting effect of MDM2 on P53 and recovers the anti-cancer function of P53 by binding to MDM2 protein. Compound 2 can recover the anti-cancer function of P53, and further induce the expression of P21. DEC, AZA and Ara-C induce the increased expression of γ-H2AX, suggesting that the DNA damage is increased. DNA damage further activates P53 and P21. Additionally, treatment with AZA or DEC can prevent the inhibition of DNMT1-UHRF1-HDAC1 complex on P21, and further synergistically induce the expression of P21 with compound 2. Ara-C treatment also activates P53-P21 pathway, and further synergistically induces the expression of P21 protein.

As shown in FIG. 18, (A-B) After being treated with DEC (100 nM) and AZA (0.33 μM) for 24 hours, then treated with new DEC (100 nM), AZA (0.33 μM) and compound 2 (40 nM) alone or in combination for another 24 hours, the expression of proteins in MOLM-13 cells. (C) After being treated with Ara-C (100 nM) or compound 2 (40 nM) alone or in combination for 48 hours, the expression of proteins in the MOLM-13 cells. (D-F) As shown, after being treated with compound 2 (40 nM), RG-7388 (40 nM), DEC (100 nM), AZA (3 μM) and Ara-C alone or in combination for 48 hours, the expression of proteins in the MOLM-13 cells. B-actin is used for confirming that the loaded proteins are the same. (G) The mechanism of action of the proposed compound 2 and DEC, AZA or Ara-C in combination on AML cells. Its results represent three independent results. RG-7388 is used as the control, and B-actin is used for confirming that the loaded proteins are the same.

In conclusion, the data strongly indicate that in the combined treatment, the observed P21 induction is potent, which is at least partly derived from the effect of synergistic anti-proliferative activity, after being treated with compound 2 in combination with AZA, DEC or Ara-C, all can increase the induction of apoptosis.

Embodiment 9. In Vivo Efficacy Study of the Combination of Compound 2 with Dabrafenib and Trametinib in the Subcutaneous A375 Cutaneous Melanoma Xenograft Model of BALB/c Immunodeficiency Mice In vivo studies were conducted to evaluate the therapeutic effect of compound 2 as a single drug and the combination of compound 2 with dabrafenib and trametinib in the subcutaneous A375 cutaneous melanoma xenograft model. The experimental design is shown in Table 8.

TABLE 8

The study design of the combination of compound 2 with dabrafenib and trametinib in the human A375 cutaneous melanoma mouse xenograft tumor model (tumor cell line: A375; 5 × 10$^6$ cells/mouse implanted subcutaneously)

| Group | Animal number | Treatment | Dose (mg/kg) | Route of administration | Schedule |
|---|---|---|---|---|---|
| 1 | 5 | Compound 2 vehicle | — | PO | QD × 7D |
|   |   | Trametinib vehicle | — | PO | QD × 21D |
|   |   | Dabrafenib vehicle | — | PO | QD × 21D |
| 2 | 5 | Compound 2 | 50 | PO | QD × 7D |
| 3 | 5 | Trametinib | 1 | PO | QD × 21D |
|   |   | Dabrafenib | 30 | PO | QD × 21D |
| 4 | 5 | Compound 2 | 50 | PO | QD × 7D |
|   |   | Trametinib | 1 | PO | QD × 21D |
|   |   | Dabrafenib | 30 | PO | QD × 21D |

The human A375 cell line was purchased from Cobioer. The cell line has been genetically authenticated and has no microbial contamination. The A375 cells were cultured in DMEM (Cat. #C11995500BT, GIBCO) supplemented with 10% fetal bovine serum (Cat. #10099-141C, GIBCO), 100 U/mL penicillin G and 100 μg/mL streptomycin (Cat. #15140-122, GIBCO). The cells were incubated at 37° C. in a humidified incubator with 5% $CO_2$.

Compound 2 was made into a homogeneous suspension by suspending Compound 2 in 0.2% HPMC in a mortar. The suspension was prepared once a week and stored at 4° C. The formulation was brought to room temperature and mixed thoroughly before use. Compound 2 was administered by oral gavage (PO) at a dose of 10 mL/kg. Dabrafenib was purchased from Selleck. Dabrafenib was suspended in 0.5% HPMC by using ultrasound to prepare a homogeneous suspension. The suspension was prepared once a week and stored at 4° C. Dabrafenib was administered by oral gavage (PO) at a dose of 10 mL/kg. Trametinib was purchased from Selleck. A clear solution was obtained by suspending in 1% CMC, 0.5% Tween 80 and 0.5% MC, and the trametinib was made into a homogeneous suspension. The solution was prepared every three days and store at 4° C. Trametinib was administered by oral gavage (PO) at a dose of 10 mL/kg.

Six-to-eight week old female BALB/c Nude mice were used in the study. The number of inoculated animals was 55, the certificate number was 202003066, the license number was SCXK (Su) 2018-0008, and the animal supplier was GemPharmatech Co, Ltd.

The results are shown in FIG. 19 and Table 9. Compound 2 as a single agent administered at 50 mg/kg daily for 7 days exerted effective anti-tumor activity with a T/C value of 58.25%. The combination of 30 mg/kg of dabrafenib and 1 mg/kg of trametinib administered daily for 3 weeks showed significant anti-tumor activity with a T/C value of 11.78% ($p<0.001$, vs. vehicle control). Adding compound 2 to the combination of dabrafenib and trametinib showed significantly enhanced anti-tumor activity, reaching a T/C value of 0.75% ($p<0.01$, vs. vehicle control; $p<0.05$, vs. compound 2 group). The corresponding synergy ratio was 9.10, indicating a synergistic anti-tumor effect. Importantly, in the group treated with compound 2 in combination with dabrafenib and trametinib, the animals achieved a 100% objective response rate with 2/5 CR and 3/5 PR during the study period.

The results in FIG. 19 and Table 9 show that the combination of compound 2 and dabrafenib plus trametinib exerts synergistic anti-tumor activity in cutaneous melanoma xenograft model, indicating the potential therapeutic application of the combination in the treatment of cutaneous melanoma.

TABLE 9

Anti-tumor activity of the combination of compound 2 with dabrafenib and trametinib in human A375 cutaneous melanoma mouse xenograft tumor model

| Treatment | RTV @ D18 (Mean ± SEM) | T/C (%) @ D18 | Synergy ratio @ D18 | mRECIST | DCR (%) | ORR (%) |
|---|---|---|---|---|---|---|
| Vehicle control | 17.36 ± 1.33 | — | — | 5/5 PD | 0 | 0 |
| Compound 2 | 10.11 ± 1.83 | 58.25 | — | 5/5 PD | 0 | 0 |
| Dabrafenib + Trametinib | 2.04 ± 0.88*** | 11.78 | — | 1/5 PR, 2/5 SD, 2/5 PD | 60 | 20 |
| Compound 2 + Dabrafenib + Trametinib | 0.13 ± 0.06**† | 0.75 | 9.10 | 2/5 CR, 3/5 PR | 100 | 100 |

**p < 0.01;
***p < 0.001, vs. vehicle control group;
†p < 0.05, vs. "compound 2" group; Synergy: Ratio > 1, synergistic; Ratio = 1, additive; Ratio < 1, antagonistic.
DCR: disease control rate, DCR is calculated based on the proportion of animals showing CR (complete response), PR (partial response) or SD (stable disease) by mRECIST; ORR: objective response rate. ORR is calculated based on mRECIST as the proportion of animals showing CR or PR.

Embodiment 10. The in vivo efficacy study of the combination of compound 2 with fulvestrant and alpelisib in the subcutaneous MCF-7 ER$^+$ breast cancer xenograft model of BALB/c nude mice. In vivo study was carried out to evaluate the therapeutic effect of the combination of compound 2 with fulvestrant and alpelisib in the subcutaneous MCF-7 ER$^+$ breast cancer xenograft model. The experimental design was shown in Table 10.

TABLE 10

The study design of the combination of compound 2 with fulvestrant and alpelisib in mouse subcutaneous MCF-7 ER$^+$ breast cancer xenograft tumor model (tumor cell line: MCF -7; 1 × 10$^7$ cells/mouse implanted subcutaneously)

| Group | Animal number | Treatment | Dose (mg/kg) | Route of administration | Schedule |
|---|---|---|---|---|---|
| 1 | 2 | Compound 2 vehicle | — | PO | QD × 7D |
|   |   | Fulvestrant vehicle | — | SC | BIW × 21D |
|   |   | Alpelisib vehicle | — | PO | QD × 21D |
| 2 | 2 | Compound 2 | 50 | PO | QD × 7D |
|   |   | Alpelisib | 25 | PO | QD × 21D |
| 3 | 2 | Fulvestrant | 20 | SC | BIW × 21D |
|   |   | Alpelisib | 25 | PO | QD × 21D |
| 4 | 2 | Compound 2 | 50 | PO | QD × 7D |
|   |   | Fulvestrant | 20 | SC | BIW × 21D |
|   |   | Alpelisib | 25 | PO | QD × 21D |

The human MCF-7 cell line was purchased from Cobioer. The cell line has been genetically identified and has no microbial contamination. The MCF-7 cells were cultured in MEM (Cat. #C12571500BT, GIBCO) supplemented with 10% fetal bovine serum (Cat. #10099-141C, GIBCO), 100 U/mL penicillin G and 100 μg/mL streptomycin (Cat. #15140-122, GIBCO). The cells were incubated at 37° C. in a humidified incubator with 5% $CO^2$.

Compound 2 was made into a homogeneous suspension by suspending Compound 2 in 0.2% HPMC in a mortar. The suspension is prepared once a week and stored at 4° C. The formulation was brought to room temperature and mixed thoroughly before use. Compound 2 was administered by oral gavage (PO) at a dose of 10 mL/kg. Fulvestrant (batch number: S119117) was purchased from Selleck. Fulvestrant was prepared by dissolving in corn oil, vortexing and sonicating into a clear solution. The solution was freshly prepared before use. Fulvestrant was given by subcutaneous injection (SC) at a dose of 10 mL/kg. Alpelisib (batch number: HY-15244) was purchased from MCE. By suspending in 0.5% CMC-Na, vortexing and sonicating, the alpelisib was made into a homogeneous suspension. The suspension of alpelisib was prepared once a week and stored at 4° C. The formulation was brought to room temperature and mixed thoroughly before use. Alpelisib was administered by oral gavage (PO) at a dose of 10 mL/kg.

Six to eight week old female BALB/c Nude mice were used in the study. The number of inoculated animals was 70, the certificate number was 202001895, the license number was SCXK (Su) 2018-0008, and the animal supplier was GemPharmatech Co, Ltd.

The results are shown in FIG. 20 and Table 11. The combination of Compound 2 at 50 mg/kg and alpelisib at 25 mg/kg exerted effective anti-tumor activity with a T/C value of 38.92%. The combination of fulvestrant at 20 mg/kg and alpelisib at 25 mg/kg daily for 3 weeks showed significant anti-tumor activity with a T/C value of 31.19%. Adding compound 2 to the combination of fulvestrant and alpelisib showed significantly enhanced anti-tumor activity, achieving a T/C value of 0%. In addition, the triple combination of compound 2 and fulvestrant and alpelisib achieve a 100% objective response rate with 2 CRs during the study period.

No significant weight loss was observed during all treatment periods.

FIG. 20 and Table 11 show that the combination of compound 2 with fulvestrant and alpelisib exerts synergistic anti-tumor activity in the ER$^+$ breast cancer xenograft model, indicating the potential therapeutic application of the combination in the treatment of ER$^+$ breast cancer.

TABLE 11

Anti-tumor effect of compound 2 in combination with fulvestrant and alpelisib in mouse subcutaneous MCF-7 ER+ breast cancer xenograft tumor model

| Treatment | RTV @ D33 (Mean ± SEM) | T/C (%) @ D33 | mRECIST | DCR (%) | ORR (%) |
|---|---|---|---|---|---|
| Vehicle control | 1.98 ± 0.56 | — | — | — | — |
| Compound 2 + alpelisib | 0.77 ± 0.02 | 38.92 | 2/2 SD | 100 | 0 |
| Fulvestrant + alpelisib | 0.62 ± 0.23 | 31.19 | 2/2 PR | 100 | 50 |
| Compound 2 + fulvestrant + alpelisib | 0.00 ± 0.00 | 0.00 | 2/2 CR | 100 | 100 |

In addition to those described herein, according to above description, various modifications of the present invention will be apparent to a person skilled in the art. Such modifications are also intended to fall within the scope of the appended claims. Each reference document cited in the present application (comprising all patents, patent applications, journal articles, books and any other publications) is incorporated herein by reference in its entirety.

The invention claimed is:

1. A pharmaceutical composition for preventing and/or treating cancer, comprising an MDM2 inhibitor and an anti-cancer agent and optionally a pharmaceutically acceptable carrier, diluent, or excipient wherein said MDM2 inhibitor is compound 2 or a pharmaceutically acceptable salt or solvate thereof:

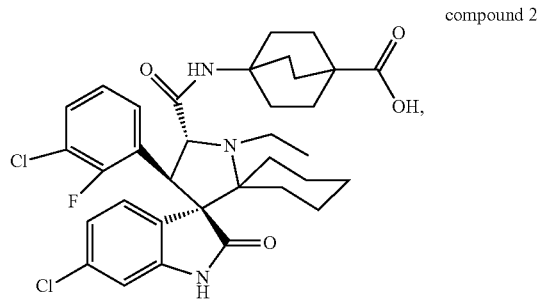 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

compound 2 wherein said anti-cancer agent is a combination of Dabrafenib and Trametinib.

2. The pharmaceutical composition according to claim 1, wherein said pharmaceutical composition or said MDM2 inhibitor or said anti-cancer agent is in the forms of tablet, capsule, granule, syrup, powder, troche, sachet, cachet, elixir, suspension, emulsion, solution, syrup, aerosol, ointment, cream and injection.

3. A kit comprising:
(a) a first component in a first container, wherein said first component comprises the pharmaceutical composition comprising MDM2 inhibitor and optionally a pharmaceutically acceptable carrier, diluent or excipient, wherein said MDM2 inhibitor is compound 2 or a pharmaceutically acceptable salt or solvate thereof:

compound 2 and
(b) a second component in a second container, wherein said second component comprises an anti-cancer agent and optionally a pharmaceutically acceptable carrier, diluent or excipient, wherein said anti-cancer agent is a combination of Dabrafenib and Trametinib.

4. The pharmaceutical composition of claim 1, wherein the weight ratio of compound 2, Dabrafenib, and Trametinib is 50:30:1.

5. The kit of claim 3, wherein the weight ratio of compound 2, Dabrafenib, and Trametinib is 50:30:1.

* * * * *